US009622690B2

(12) United States Patent
Terashima et al.

(10) Patent No.: US 9,622,690 B2
(45) Date of Patent: *Apr. 18, 2017

(54) MEASUREMENT DEVICE

(71) Applicant: PANASONIC CORPORATION, Osaka (JP)

(72) Inventors: Noriyoshi Terashima, Kanagawa (JP); Masataka Nadaoka, Ehime (JP)

(73) Assignee: PANASONIC HEALTHCARE HOLDINGS CO., LTD., Tokyo (JP)

(*) Notice: Subject to any disclaimer, the term of this patent is extended or adjusted under 35 U.S.C. 154(b) by 107 days.

This patent is subject to a terminal disclaimer.

(21) Appl. No.: 14/056,279

(22) Filed: Oct. 17, 2013

(65) Prior Publication Data
US 2014/0046160 A1   Feb. 13, 2014

Related U.S. Application Data

(63) Continuation of application No. 13/127,247, filed as application No. PCT/JP2009/005673 on Oct. 27, 2009, now Pat. No. 8,597,570.

(30) Foreign Application Priority Data

Nov. 4, 2008   (JP) .................. 2008-283784

(51) Int. Cl.
A61B 5/145    (2006.01)
A61B 5/1486   (2006.01)
(Continued)

(52) U.S. Cl.
CPC ........ A61B 5/14532 (2013.01); A61B 5/1486 (2013.01); A61B 5/416 (2013.01);
(Continued)

(58) Field of Classification Search
CPC ................ A61B 5/4866; A61B 5/0205; A61B 2562/0219; A61B 5/0002; A61B 5/11;
(Continued)

(56) References Cited

U.S. PATENT DOCUMENTS 6,004,441 A    12/1999   Fujiwara et al.
6,212,417 B1   4/2001    Ikeda et al.
(Continued)

FOREIGN PATENT DOCUMENTS

DE    2007/010056    9/2007
EP    0816986        1/1998
(Continued)

OTHER PUBLICATIONS

Search report from E.P.O., mail date is Oct. 9, 2013.
(Continued)

Primary Examiner — Sally Merkling
(74) Attorney, Agent, or Firm — Greenblum & Bernstein, P.L.C.

(57) ABSTRACT

A measurement device includes a housing that has an attached biosensor that includes a reagent selectively responding to a specific analyte in a biological fluid, and is configured so as to be carried by a user, an analyte measurer that measures a concentration of the specific analyte with a biosensor, and a motion measurer that measures a motion level of the housing. A living activity level calculator calculates a living activity level of the user based on the motion level measured by the motion measurer, a recorder records the living activity level calculated by the living activity level calculator, and a controller associates the concentration of the specific analyte measured by the analyte measurer with an event of living activity of the user, estimated based on the living activity level recorded in the recorder, and records them in the recorder.

7 Claims, 54 Drawing Sheets

(51) Int. Cl.
*A61B 5/00* (2006.01)
*A61M 5/142* (2006.01)
*A61M 5/172* (2006.01)
*G01N 27/327* (2006.01)
*A61B 5/11* (2006.01)

(52) U.S. Cl.
CPC .......... *A61B 5/4839* (2013.01); *A61B 5/4866* (2013.01); *A61M 5/14244* (2013.01); *A61M 5/1723* (2013.01); *G01N 27/3273* (2013.01); *A61B 5/11* (2013.01); *A61B 2560/0406* (2013.01); *A61B 2562/0219* (2013.01); *A61B 2562/0295* (2013.01); *A61M 2005/1726* (2013.01); *A61M 2205/3368* (2013.01); *A61M 2205/502* (2013.01); *A61M 2230/201* (2013.01); *A61M 2230/50* (2013.01); *A61M 2230/63* (2013.01)

(58) Field of Classification Search
CPC ......... A61B 5/1118; A61B 5/16; A61B 5/681; A61B 5/7264; A61B 5/7275; A61B 5/7282; G06F 19/3437; G06F 19/3456; G06F 19/3487; G06Q 50/24
USPC ...................................................... 604/890.1
See application file for complete search history.

(56) References Cited

U.S. PATENT DOCUMENTS

| | | |
|---|---|---|
| 6,258,229 B1 | 7/2001 | Winarta et al. |
| 6,287,451 B1 | 9/2001 | Winarta et al. |
| 6,299,757 B1 | 10/2001 | Feldman et al. |
| 6,309,526 B1 | 10/2001 | Fujiwara et al. |
| 6,338,790 B1 | 1/2002 | Feldman et al. |
| 6,447,657 B1 | 9/2002 | Bhullar et al. |
| 6,461,496 B1 | 10/2002 | Feldman et al. |
| 6,484,046 B1 | 11/2002 | Say et al. |
| 6,540,890 B1 | 4/2003 | Bhullar et al. |
| 6,571,193 B1 | 5/2003 | Unuma et al. |
| 6,576,101 B1 | 6/2003 | Heller et al. |
| 6,592,745 B1 | 7/2003 | Feldman et al. |
| 6,616,819 B1 | 9/2003 | Liamos et al. |
| 6,618,934 B1 | 9/2003 | Feldman et al. |
| 6,645,359 B1 | 11/2003 | Bhullar et al. |
| 6,755,949 B1 | 6/2004 | Bhullar et al. |
| 6,767,440 B1 | 7/2004 | Bhullar et al. |
| 6,814,843 B1 | 11/2004 | Bhullar et al. |
| 6,814,844 B2 | 11/2004 | Bhullar et al. |
| 6,866,758 B2 | 3/2005 | Bhullar et al. |
| 6,911,621 B2 | 6/2005 | Bhullar et al. |
| 7,003,340 B2 | 2/2006 | Say et al. |
| 7,073,246 B2 | 7/2006 | Bhullar et al. |
| 8,145,431 B2 | 3/2012 | Kloepfer et al. |
| 2003/0153900 A1* | 8/2003 | Aceti et al. ................. 604/890.1 |
| 2004/0152957 A1* | 8/2004 | Stivoric ................... A61B 5/01 600/300 |
| 2006/0195029 A1* | 8/2006 | Shults et al. .................. 600/345 |
| 2007/0033074 A1* | 2/2007 | Nitzan ................ G06F 19/3437 705/3 |
| 2007/0219436 A1 | 9/2007 | Takase et al. |
| 2008/0092638 A1 | 4/2008 | Brenneman et al. |
| 2009/0312615 A1 | 12/2009 | Caduff et al. |
| 2010/0060604 A1 | 3/2010 | Zwart et al. |

FOREIGN PATENT DOCUMENTS

| | | |
|---|---|---|
| JP | 56-7938 | 1/1981 |
| JP | 58-149730 | 9/1983 |
| JP | 58-206723 | 12/1983 |
| JP | 59-109987 | 6/1984 |
| JP | 59-202016 | 11/1984 |
| JP | 5-5628 | 1/1993 |
| JP | 5-25206 | 2/1993 |
| JP | 5-332783 | 12/1993 |
| JP | 6-24591 | 1/1994 |
| JP | 6-300582 | 10/1994 |
| JP | 7-80115 | 3/1995 |
| JP | 7-139964 | 6/1995 |
| JP | 7-181056 | 7/1995 |
| JP | 7-239238 | 9/1995 |
| JP | 8-103568 | 4/1996 |
| JP | 8-117211 | 5/1996 |
| JP | 8-298468 | 11/1996 |
| JP | 09-223214 | 8/1997 |
| JP | 10-113343 | 5/1998 |
| JP | 11-76612 | 3/1999 |
| JP | 11-211502 | 8/1999 |
| JP | 11-342270 | 12/1999 |
| JP | 2000-51528 | 2/2000 |
| JP | 2000-67205 | 3/2000 |
| JP | 2000-148964 | 5/2000 |
| JP | 2000-213954 | 8/2000 |
| JP | 2000-283789 | 10/2000 |
| JP | 2000-312666 | 11/2000 |
| JP | 2000-333918 | 12/2000 |
| JP | 2001-29323 | 2/2001 |
| JP | 2001-61806 | 3/2001 |
| JP | 2001-133284 | 5/2001 |
| JP | 2001-143048 | 5/2001 |
| JP | 2001-184477 | 7/2001 |
| JP | 2001-297155 | 10/2001 |
| JP | 2002-233663 | 8/2002 |
| JP | 2002-238863 | 8/2002 |
| JP | 2003-220039 | 8/2003 |
| JP | 2004-24699 | 1/2004 |
| JP | 2007-54241 | 3/2007 |
| JP | 2007-75586 | 3/2007 |
| JP | 3984253 | 7/2007 |
| JP | 2007-216029 | 8/2007 |
| JP | 2007-236917 | 9/2007 |
| JP | 2007-244736 | 9/2007 |
| JP | 2007-253482 | 10/2007 |
| JP | 2007-323246 | 12/2007 |
| JP | 2008-11865 | 1/2008 |
| WO | 95/02357 | 1/1995 |
| WO | 96/08281 | 3/1996 |
| WO | 96/14096 | 5/1996 |
| WO | 96/27398 | 9/1996 |
| WO | 00/10628 | 3/2000 |
| WO | 00/19887 | 4/2000 |
| WO | 00/64940 | 11/2000 |
| WO | 01/58511 | 8/2001 |
| WO | 01/96986 | 12/2001 |
| WO | 02/00111 | 1/2002 |
| WO | 02/20073 | 3/2002 |
| WO | 02/40083 | 5/2002 |
| WO | 02/078538 | 10/2002 |
| WO | 03/015005 | 2/2003 |
| WO | 03/098165 | 11/2003 |
| WO | 2004/019172 | 3/2004 |
| WO | 2004/032715 | 4/2004 |
| WO | 2004/034221 | 4/2004 |
| WO | 2005/012873 | 2/2005 |
| WO | 2005/023348 | 3/2005 |
| WO | 2005/027720 | 3/2005 |
| WO | 2005/029242 | 3/2005 |
| WO | 2005/065538 | 7/2005 |
| WO | 2005/092177 | 10/2005 |
| WO | 2006-046648 | 5/2006 |
| WO | 2007/053963 | 5/2007 |

OTHER PUBLICATIONS

Massachusetts Medical Society, "The Effect of Intensive Treatment of Diabetes on the Devolpment and Progression of long-Term Complications in Insulin-Dependent Diabetes Mellitus", The New England Journal of Medicine, Sep. 30, 1993, pp. 977-986.

Turner RC. et al., "Risk factors for coronary artery disease in non-insulin dependent diabetes mellitus: United Kingdom prospective diabetes study (UKPDS:23)", BMJ vol. 316, Mar. 14, 1998, pp. 823-828.

(56) References Cited

OTHER PUBLICATIONS

Johnson J.L. et al., "Exercise Training Amount and Intensity effects on Metabolic Syndrome (From Studies of a Targeted Risk Reduction Intervention through Defined Exercise)", America Journal of Cardiology, vol. 100, Dec. 15, 2007, pp. 1759-1766.

Ainsworth, B.E. et al., "Compendium of Physical Activities: Classification of energy costs of human physical activities", Medicine & Science in Sports & Exercise, Jan. 1993, pp. 71-80.

Nelson ME. et al., "Physical Activity and Public Health in Older Adults: Recommendation from the American College of Sports Medicine and the American Heart Association", Med Sci Sports Exerc., Aug. 2007, pp. 1435-45.

Saris W.H.M. et al., "How Much Physical Activity is Enough to Prevent Unhealthy Weight Gain? Outcome of the IASO 1st Stock Conference and Consensus Statement", Obesity Reviews vol. 4 Issue 2:, May 2003, pp. 101-114.

Sallis J. et al., "Environmental Interventions for Eating and Physical Activity a Randomized Controlled Trial in Middle Schools", American Journal of Preventive Medicine vol. 24, Issue 3:, ., pp. 209-217, Apr. 2003.

Lee I-Min et al., "Relative Intensity of Physical Activity and Risk of Coronary Heart Disease", Circulation, 2003, pp. 1110-1116.

"Seven Continuous Glucose Monitoring System User's Guide", Dexcom, 2007, http://www.dexcom.com/html/dexcom_products_user_manuals.html.

Peyrot m. et al., "Psychosocial problems and barriers to improved diabetes management; results of the Cross-National Diabetes Attitudes, Wishes and Needs (DAWN) Study", Diabetic Medicine. vol. 22, No. 10, Oct. 2005, pp. 1379-1385.

Levine, J.A., "Non-Exercise Activity Thermogenesis (NEAT): Environment and Biology", Am. J. Physiol. 286, 2004, pp. E675-685.

Haupt A. et al., "The Effects on Skin Temperature and Testing Site on Blood Glucose Measurements Taken by a Modern Blood Glucose Monitoring Device", Diabetes Technology & Therapeutics., Aug. 1, 2005, pp. 597-601.

Pfutzner A. et al., "Impact of Posture and Fixation Technique on Impedence Spectroscopy Used for Continuous and noninvasive Glucose Monitoring", Diabetes Technology & Therapeutics., Aug. 1, 2004, pp. 435-441.

Khalil Omar S., "Non-Invasive Glucose Measurement Technologies: An Update from 1999 to the Dawn of the New Millenium", Diabetes Technology & Therapeutics., Oct. 1, 2004, pp. 660-697.

Haller Michael J. et al., "Adverse Impact of Temperature and Humidity on Blood Glucose Monitoring Reliability: A Pilot Study", Diabetes Technology & Therapeutics., Feb. 1, 2007, pp. 1-9.

\* cited by examiner

| PREPRANDIAL BLOOD GLUCOSE LEVEL | | | POSTPRANDIAL BLOOD GLUCOSE LEVEL | | |
|---|---|---|---|---|---|
| AVERAGE OVER PRECEDING 2 WEEKS 106mg/dl | | | AVERAGE OVER PRECEDING 2 WEEKS 164mg/dl | | |
| Feb.24 07:25 | 98mg/dl | ♪♪♪♪ | Feb. 24 08:25 | 168mg/dl | ! ! |
| Feb. 24 11:12 | 110mg/dl | ♪♪♪ | Feb. 24 12:39 | 180mg/dl | ! ! |
| Feb. 24 16:36 | 115mg/dl | ♪♪ | Feb. 24 13:33 | 130mg/dl | ! ! |
| Feb. 24 17:44 | 96mg/dl | ♪♪♪♪ | Feb. 24 19:13 | 255mg/dl | ! ! ! |
| Feb. 24 22:09 | 122mg/dl | ♪♪ | Feb. 24 20:09 | 122mg/dl | ! ! |
| Feb. 25 03:02 | 80mg/dl | ♪♪♪♪ | Feb. 25 08:02 | 144mg/dl | ! ! |
| Feb. 25 07:16 | 89mg/dl | ♪♪♪♪ | Feb. 25 09:26 | 125mg/dl | ! ! |
| Feb. 25 11:22 | 89mg/dl | ♪♪♪♪ | Feb. 25 13:22 | 189mg/dl | ! ! |

FIG.18

| PREPRANDIAL BLOOD GLUCOSE LEVEL | | | POSTPRANDIAL BLOOD GLUCOSE LEVEL | | |
|---|---|---|---|---|---|
| AVERAGE OVER PRECEDING 2 WEEKS 106mg/dl | | | AVERAGE OVER PRECEDING 2 WEEKS 164mg/dl | | |
| Feb.24 07:25 | 98mg/dl | ♪♪♪♪ | Feb. 24 20:09 | 122mg/dl | ! ! |
| Feb. 24 08:25 | 168mg/dl | ! ! | Feb. 24 22:09 | 122mg/dl | ♪♪ |
| Feb. 24 11:12 | 110mg/dl | ♪♪♪ | Feb. 25 03:02 | 80mg/dl | ♪♪♪♪ |
| Feb. 24 12:39 | 180mg/dl | ! ! | Feb. 25 07:16 | 89mg/dl | ♪♪♪♪ |
| Feb. 24 13:33 | 130mg/dl | ! ! | Feb. 25 08:02 | 144mg/dl | ! ! |
| Feb. 24 16:36 | 115mg/dl | ♪♪ | Feb. 25 09:26 | 125mg/dl | ! ! |
| Feb. 24 17:44 | 96mg/dl | ♪♪♪♪ | Feb. 25 11:22 | 89mg/dl | ♪♪♪♪ |
| Feb. 24 19:13 | 255mg/dl | ! ! ! | Feb. 25 13:22 | 189mg/dl | ! ! |

FIG.19

MEASUREMENT DEVICE

CROSS-REFERENCE TO RELATED APPLICATIONS

The present application is a continuation application of pending U.S. application Ser. No. 13/127,247, filed on May 3, 2011, which is a National Stage of International Patent Application No. PCT/JP2009/005673, filed Oct. 27, 2009, which claims priority to Japanese Application No. JP 2008-283784, filed on Nov. 4, 2008, the disclosures of which are expressly incorporated by reference herein in their entireties.

TECHNICAL FIELD

The present invention relates to measurement devices, insulin infusion devices, measurement methods, methods of controlling insulin infusion device and programs, e.g., to improvements on blood glucose meters, insulin infusion devices and methods of controlling the same, for diabetic patients.

BACKGROUND ART

People with diabetes need to keep their blood glucose level in the normal range by regularly monitoring it and injecting insulin based on the measured blood glucose level. This requires routine blood glucose measurements: Using a blood tester, the patient pierces the skin (e.g., on the finger tip) to draw blood, allowing a small quantity of blood to be sampled into the device for the analysis of glucose or other blood components.

The present invention particularly relates to compact, battery-driven portable blood glucose meters designed for self-monitoring of blood glucose levels by diabetic patients. Blood glucose meters are well known in the art. The field to which the present invention pertains is often very difficult to understand due to the high rate of technological progress and to the use of different technical terms by different inventors. Some technical terms are consistently used throughout the specification so long as the intended meanings are not lost, in order to distinguish the present invention over prior art as much as possible. The definitions of technical terms given in the specification are clarified as much as possible in the "Description of Embodiments" section described later.

Diabetes is a group of metabolic diseases in which a person chronically shows high blood sugar due to deficient insulin action. There are four main types of diabetes: (1) type 1 diabetes in which beta cells of the pancreas are unable to produce enough insulin due to autoimmune disease or sudden destruction of the cells; (2) type 2 diabetes characterized by relative insulin deficiency due primarily to insulin secretion reduction or insulin resistance; (3) diabetes that results from defects in genes that are responsible for beta cell function or insulin signaling, or from diseases such as exocrine pancreatic insufficiency; and (4) gestational diabetes.

Most patients with type 1 diabetes need insulin therapy, and so too do many of the patients suffering from other forms of diabetes.

Insulin was first discovered by Banting and Best in 1921. Animal-source insulin formulations, (e.g., those purified from the bovine or swine spleen) had been the only insulin formulations available until 1979, when the human insulin gene was identified and characterized. At present, genetically-engineered human insulin formulations as well as insulin analogue formulations are widely used.

Diabetic patients who need insulin therapy use a small (typically pen-shaped) injection syringe to inject an insulin formulation into the arm's, femoral or abdominal subcutaneous adipose tissue. The limited routes of administration stem from the fact that insulin is digested in the stomach and thus cannot be taken orally.

Insulin formulations come in roughly three basic types, each of which has its own onset time and duration time. For example, fast-acting insulin is characterized by the most rapid onset and shorter duration time.

Fast-acting insulin is employed when several injections are needed everyday. It is injected 15 to 20 minutes before meals or immediately after meals. Fast-acting insulin is designed to have a maximum activity 2 to 4 hours after the injection, with a duration of action lasting 6 to 8 hours.

Intermediate-acting insulin is designed to take effect 1 to 3 hours after the injection and achieve a maximum efficacy 6 to 10 hours after the injection, with a duration of action lasting 18 to 26 hours. A typical administration schedule of this type of insulin is to administer in the morning to cover insulin needs for the first half of the day, or to administer in the evening to cover overnight needs.

Slow-acting insulin is designed to hardly take effect during approximately 6 hours after injection and have a duration of action of 28 to 36 hours. Recently, other types of insulin formulations, including ultra-fast-acting insulin formulations and combined insulin formulations, are added to the insulin formulation category in some cases. These many types of insulin formulations, each having many properties, may be used alone as described above, but in many cases are used in combination to provide more efficacy.

For example, a single injection of intermediate-acting insulin per day merely results in minimal control of blood glucose levels; it is highly unlikely that optimal blood glucose control can be realized. However, a combined injection of two different types of insulin formulations—for example, fast-acting type and intermediate-acting type—in the morning can ensure more strict blood glucose control. Moreover, for the second injection, one or both of the fast-acting insulin and intermediate-acting insulin is administered at dinner time or bedtime.

An administration schedule currently adopted to achieve most strict blood glucose control is to inject both of a fast-acting insulin formulation and an intermediate-acting insulin formulation in the morning and evening, with several additional injections of a fast-acting insulin formulation at daytime. It is critical to alter the dosage of administration according to changes in the quantity of insulin required. Such a highly effective administration regime, however, requires that patients themselves have knowledge of diabetes as well as that careful attention be paid during therapy.

Among other factors, required insulin dose is important. Although diabetic patients, particularly elder diabetic patients, may receive the same dose of insulin formulation consistently everyday, the insulin dose needs to be adjusted according to their dietary, activity level or blood glucose level. People with diabetes have high blood glucose levels and thus risks of physiological disorders associated with degradation of microvessels (e.g., renal failure, skin ulcer, or intravitreal hemorrhage).

Meanwhile, hypoglycemia is triggered by accidental administration of excess insulin or in association with excess exercise or insufficient food intake, e.g., after regular administration of insulin or other glucose reducing agent. In extreme cases, hypoglycemia results in the brain's failure to maintain its energy metabolism, leading to psychosis, unconsciousness and, in serious cases, death.

It is therefore critical in diabetes therapy to control blood glucose levels. Proper blood glucose management requires routine confirmation of variations in blood glucose level (see Patent Literatures 1 and 2).

Controlling patient's blood glucose level with a blood glucose measurement system was scientifically proved to be clinically effective by the Diabetes Control and Complications Trial (hereinafter "DCCT"), a large-scale clinical study of diabetes, the findings of which were announced by the Diabetes Control and Complications Trial Research Group in 1993 (see Non-Patent Literature 3).

The DCCT replaced the conventional measurement of blood glucose, which was permitted only in medical facilities, with the now common self-monitoring of blood glucose (SMBG) that enables the patient to measure blood glucose level easily. The blood glucose measurement system is one in which a disposable blood glucose sensor is attached to a blood glucose meter.

The subject pierces the skin (e.g., on the finger or palm) with a puncture needle to draw a trace amount (several µL) of blood, allowing the blood to be loaded in the reagent layer of the blood sensor, where electrochemical reactions, mainly enzyme reactions, of glucose take place for the measurement of the concentration of glucose in blood.

Recent standard blood glucose sensors are capable of more precise measurement with a trace quantity of blood (1 µL or less) even in several seconds (see Patent Literatures 1 to 21, and 23 to 25).

Further, these blood glucose meters are so small as to be portable, enabling diabetic patients to measure, either inside or outside the house, blood glucose levels by themselves easily and precisely for self-monitoring.

In the DCCT, 1,441 diabetic patients, aged 13 to 39, with type 1 diabetes in the United States and Canada, were examined to study whether keeping blood glucose levels as close to normal as possible can slow the onset and progression of vascular complications caused by diabetes. The study showed that controlling blood glucose level plays a pivotal role in slowing the onset and progression of diabetic microvascular complication—one of the three major complications of diabetes. The study also showed that individuals with a history of better control had lesser onset of complications (see Non-Patent Literature 3).

Thus, the user of a self blood glucose meter controls blood glucose levels by determining the diet or insulin dose based on the measured blood glucose readings displayed on the screen. The user monitors changes in blood glucose level to keep it in the normal range.

In the DCCT, HbA1c level was employed as an indicator of blood glucose control. The American Diabetes Association set the HbA1c target to 7.0%, and research was undertaken using various types of insulin formulations and various methods of administration.

However, some clinical research reported that during insulin potentiation therapy for diabetic patients, some showed remarkable body weight increase as HbA1c level dropped to near 7.0%, and others did not show remarkable body weight increase and no reduction in HbA1c level to near 7.0% (see Non-Patent Literatures 4 and 5).

While the DCCT established a clear direction for the treatment of complications of diabetics, it is frequently reported that many diabetic patients cannot achieve target HbA1c levels, and what is even worse, they elevated HbA1c levels year after year.

Macroangiopathy (cardiovascular disease associated with arterial sclerosis), a complication which would not be "peculiar" to diabetes, is seen even in short-term diabetic patients who have well-managed blood glucose levels. This is also demonstrated in clinical trials such as the United Kingdom Prospective Diabetes Study (hereinafter "UKPDS"), in which the onset and progression of arterial sclerosis was not prevented by merely relying on blood glucose control using HBA1c level as a main indicator (see Non-Patent Literature 6).

Insulin resistance, which was found problematic in the above clinical trial, slows carbohydrate metabolism as well as lipid metabolism to trigger diabetes or hyperlipidemia. This leads to insulin resistance and excessive accumulation of abdominal visceral fat that in turn causes insulin resistance, disturbing the blood pressure adjustment mechanism and eventually leading to hyperpiesia. This clinical condition is metabolic syndrome in itself.

Visceral fat obesity accelerates the progress of arterial sclerosis and slows carbohydrate metabolism, which may eventually result in the development of diabetes. If an individual with a short duration of diabetes and a history of better blood glucose control developed cardiovascular disease, this fact is consistent with the conclusion of the UKPDS described above.

To address the problem of high prevalence of diabetes associated with metabolic syndrome due to westernization, it would be increasingly important to actively promote diet therapy and exercise therapy (see Non-Patent Literatures 1 and 2).

Exercise therapy is effective in the treatment of type-2 diabetes, and its effectiveness as a countermeasure against metabolic syndrome as well as against visceral fat obesity underlying metabolic syndrome has been focused. In 2007, Johnson et al reported the effects of exercise therapy in detail.

Johnson et al reported the results of 8-month exercise training programs conducted on 171 overweight subjects, including 41 individuals diagnosed as metabolic syndrome (those who have three or more of the following risk factors: elevated blood glucose, increased waist circumference, elevated blood pressure, and hyperlipidemia), randomly assigned to one of the following 3 exercise training groups.

Group (1): walking for 30 minutes to 1 hour a day for 3 to 5 days (equivalent to walking 19 km/week); Group (2): jogging 19 km/week, or Group (3): running 32 km/week.

Effect of exercise was observed for all 3 exercise groups. At the end of the trial, the number of subjects presented with metabolic syndrome was reduced to 27 (see Non-Patent Literature 7).

Meanwhile, extensive research has been undertaken on exercise itself: As a measure of the metabolic rate during a physical activity (e.g., training), metabolic equivalents (hereinafter "METs") was established, a unit for expressing the intensity of physical activities by the multiplication equivalent to the counterpart during rest. This measure enabled easy conversion of exercise intensity into calories.

One MET is equivalent to the rest metabolic rate, i.e., 3.5 ml $O_2$-$kg^{-1}$-$min^{-1}$. Using METs, the standardized unit of intensity of physical activities, the amount of any exercise can be expressed in terms of METs multiplied by the duration of the exercise (see Non-Patent Literature 8).

The research led to scientific studies of exercise in mathematical and biological aspects. By way of one example, extensive research is being undertaken on exercise, health and disease across a broad set of ages, races and environments, such as relationship between exercise amount and unhealthy weight gain, environmental interventions for eating and physical activity in middle schools, and relative intensity of physical activity and coronary heart disease (see Non-Patent Literatures 9-12).

If the amount of exercise (intensity of physical activities multiplied by time) is not suited to the clinical condition of the diabetic patient, it results in side effects, including risks of elevated blood glucose caused by exercise under high blood glucose level conditions; fundal hemorrhage due to aggravated retinopathy; arrhythmia or cardiac arrest due to autonomic disorder; hypoglycemia unawareness; progression of nephropathia; and, in the case of obesity, articular disorder.

As most diabetic patients are not young, they may suffer from articular disorder and, therefore, it is often the case that they cannot perform exercise. Thus, non-exercise activity thermogenesis (NEAT), the energy expenditure of physical activities other than exercise, became known by the paper published by the research group of the Mayo Clinic (Unites States) in the 1990s (see Non-Patent Literature 13).

In the 2007 report by Johnson et al above, exercise was shown to be effective even with the modest exercise program (walking 19 km/week). It is thus expected that exercise programs will be developed that can improve, even when used by older diabetic patients, metabolic syndrome outcomes and blood glucose levels (see, inter alia, Non-Patent Literature 7).

The Japan Diabetes Society considers blood glucose control by exercise therapy as a first step toward treating diabetes. While paying attention to metabolic syndrome, Treatment Guide for Diabetes 2006-2007 focuses on "sustained well controlled blood glucose level, body weight, blood pressure and serum lipid level", and "prevention of onset and progression of diabetic microvascular complications (retinopathy, nephropathia and nerve disorder) and arteriosclerotic diseases (ischemic cardiac disease, cerebrovascular disease, and arteriosclerosis obliterans)".

The ultimate objective of diabetes treatment is to: attain quality of life (QOL) comparable to those of healthy individuals as well as to ensure lifespan expectancy comparable to those of healthy individuals (see Non-Patent Literature 2). It is, however, difficult to achieve this objective only with a blood glucose meter and medications like insulin, thus prompting research and development of various devices, drugs and treatment methods (see Non-Patent Literature 2).

One recent example of the result of the research and development is a glucose measurement method that is capable of continuous measurement of the glucose level in the interstitial fluid.

For example, Glucowatch (Cygnas Inc. U.S), a device used in the U.S. and other countries, is capable of continuous measurement of glucose level in interstitial fluid by reverse iontophoresis. This device is a noninvasive glucose monitoring device which can collect glucose from interstitial fluid across the patient's skin without relying on heat, electricity or chemicals. More specifically, the device monitors blood glucose in real time, i.e., in a time period short enough to enable a diabetic patient to take appropriate action to correct blood glucose levels.

In a preferred embodiment, the glucose collecting device includes a reservoir containing a glucose collection medium (e.g., water), which reservoir is placed in the stratum corneum of the patient's skin for a predetermined period of time. After the passage of a predetermined time period, at least a portion of the glucose collection medium is taken out of the reservoir for subsequent analysis to measure the quantity of glucose present. The commercial product distributed in the market is, as its name indicates, a wristwatch-type glucose monitoring device (see Patent Literature 26).

As a method and system for continuous glucose monitoring configured by a glucose sensor and measurement, a convenient method and system for monitoring physiological characteristic values (characteristic value monitoring system) are disclosed. The glucose sensor is primarily adapted for use in subcutaneous human tissue.

The system is disclosed as being placed in a variety of other types of physiological milieus, such as muscle, lymph, organ tissue, veins, arteries or the like, as well as being used in related environments such as animal tissue, providing sensor readings on an intermittent, near-continuous or continuous basis.

A signal from the sensor set is transmitted to the characteristic monitor. The sensor set and monitor are disclosed as being for determining glucose levels in the body fluids of the user without the use of, or necessity of, a wire of cable connection between the transmitter and the monitor (see Patent Literature 27).

A telemetered characteristic monitor system for remotely monitoring user's characteristic is disclosed that includes a remotely located data receiving device, a sensor for producing signal indicative of a characteristic of a user, and a transmitter device.

The transmitter device includes a housing and a sensor connector coupled to the housing. The sensor connector can be coupled to the sensor for receiving a signal therefrom.

The transmitter device further includes a processor and a transmitter. The processor is disposed in the housing coupled to the sensor connector and processes the signals from the sensor for delivery to the remotely located data receiving device. The transmitter is coupled to the processor for wirelessly transmitting the processed signals to the remotely located data receiving device.

The sensor set is disclosed as being able to be implanted in and/or through subcutaneous, demal, sub-dermal, inter-peritoneal or peritoneal tissue. The transmitter is disclosed as transmitting data from the sensor set to the characteristic monitor for determining body characteristics. The sensor and monitor are for determining glucose levels in the blood and/or body fluids of the user without the use of, or necessity of, a wire or cable connection between the transmitter and the monitor.

However, it is disclosed that it will be recognized that further embodiments of the sensor and monitor may be used to determine the levels of other agents, characteristics or compositions, such as hormones, cholesterol, medication concentrations, pH, oxygen saturation, viral loads (e.g., HIV), or the like. Moreover, it is disclosed that further embodiments may provide sensor readings on an intermittent or continuous basis (see Patent Literature 28).

An electrochemical sensor for determining the presence or concentration of an analyte in a fluid is disclosed, the sensor including (1) a membrane system containing an enzyme, wherein the enzyme reacts with the analyte; (2) an electroactive surface including a working electrode, the working electrode including a conductive material and configured to measure a product of the reaction of the enzyme with the analyte; and (3) an auxiliary electrode including a conductive material and configured to generate oxygen, wherein the auxiliary electrode is situated such that the oxygen generated diffuses to the enzyme or to the electroactive surface.

The sensor is disclosed as being a continuous device, for example a subcutaneous, transdermal, or intravascular device. In some embodiments, the device is disclosed as being capable of analyzing a plurality of intermittent blood samples.

The sensor may use any known method, including invasive, minimally invasive, and noninvasive sensing techniques, to provide an output signal indicative of the concentration of the analyte of interest.

The sensor is of the type that senses a product or reactant of an enzymatic reaction between an analyte and an enzyme in the presence of oxygen as a measure of the analyte in vivo or in vitro. Such a sensor typically includes a membrane surrounding the enzyme through which a bodily fluid passes and in which an analyte within the bodily fluid reacts with an enzyme in the presence of oxygen to generate a product.

The product is then measured using electrochemical methods and thus the output of an electrode system functions as a measure of the analyte.

It is also disclosed in some embodiments that the electrode system can be used with any of a variety of known in vivo or in vitro analyte sensors or monitors. In some embodiments, the analyte for measurement by the sensing regions, devices, and methods is glucose (see Patent Literature 29).

Various types of sensors that are capable of measuring the flow rate of a fluid that passes over the electrodes of the sensor are disclosed. In any of the sensors, an electrode, designated as the flow rate-determining electrode, is used in conjunction with the conventional electrodes such as a working electrode, a reference electrode, and a counter electrode, to determine the flow rate of the fluid.

In another aspect a sensor is disclosed that measures the concentration of an analyte in a sample of fluid when the sample flows continuously over the electrodes of the sensor, especially when the flow rate of the biological sample is relatively low.

It is disclosed in Patent Literature 30 that the sensor and method disclosed are particularly applicable to continuous monitoring sensors that involve the measurement of a reaction product or a reactant as a means for determining the concentration of an analyte in a biological sample. With reference to the drawings, the sensor can be placed in an insulating attachment (not shown) having two openings. The sample inlet and sample outlet are aligned with these openings in the attachment, and the sensor can be secured to the device with the aid of alignment rings.

One of the openings in the attachment serve as the inlet, and the other opening serves as the outlet. This outlet is also connected to a reservoir, where the used sample is stored. The outlet is also connected to a vacuum generator that creates a necessary pressure difference for the sample to flow out of the artificial opening in the skin of the body part. The attachment can be fastened to the body part by means of a pressure-sensitive adhesive, such as a double-sided adhesive tape (see Patent Literature 30).

As described above, CGM system (hereinafter "CGMS") glucose sensors need to be kept attached to the body during monitoring on their sensor section. Glucose sensors that can be worn during sleeping and, more recently, glucose sensors that can be worn for a straight week are emerging on the market (see Non-Patent Literature 14).

Nevertheless, blood glucose control is impossible only with the CGMS due to the time lag between the measurement and the arrival of glucose from the vascular blood to the interstitial fluid or due to the time lag between measurements which is inherent in the CGMS.

It is said that the required insulin dose varies depending on the body weight, emotional stress or disease, especially types of infectious diseases. Failure to appropriately adjust the insulin dose or timing of the injection results in either insulin overdose that triggers hypoglycemia or in insulin shortage that triggers hyperglycemia, both of which is fatal to the body.

As a measure of reducing such risks, continuous subcutaneous insulin infusion (hereinafter "CSII") is increasingly spreading throughout the U.S. and many other countries (see, inter alia, Non-Patent Literature 1).

As such a device, Flaherty J Christopher et al discloses devices, systems and methods for patient infusion, specifically a system including a separate, remote control device including a fluid delivery device.

The disclosed fluids to be delivered include insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The disclosed medical conditions to be treated include diabetes, cardiovascular disease, pain, chronic pain, cancer, AIDS, neurological diseases, Alzheimer's disease, ALS, hepatitis, Parkinson's disease and spasticity. Thus, Flaherty J Christopher et al discloses a system that may function as an insulin pump (see Patent Literature 31).

Further, Flaherty J Christopher et al discloses a fluid delivery device designed to deliver insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics, for the treatment of diabetes, cardiovascular disease, pain, chronic pain, cancer, AIDS, neurological diseases, Alzheimer's Disease, ALS, hepatitis, Parkinson's disease or spasticity. The device includes a housing that surrounds a reservoir chamber.

In fluid communication with the reservoir chamber is a dispenser for dispensing the fluid from the reservoir in finite amounts. The dispenser is controlled by an electronic microcontroller (referred to as a "local processor") of the fluid delivery device. The fluid delivery device further includes a communication element that receives information from a remote control device not mechanically attached to the fluid delivery device (see Patent Literature 32).

Ahead of the above-described inventions, Funderburk Jeffery V et al disclosed, as an infusion pump of the type used for controlled delivery of medication to a patient, an improved infusion pump and related medication-containing syringe that include matingly interfitting components to ensure pump use with a syringe that is used to administer insulin and other medications (see Patent Literature 33).

In Patent Literature 34, Funderburk Jeffery V et al discloses improvements in medical fluid infusion systems and devices for delivering a selected infusion fluid, stating that patients are required to exercise at least some degree of caution in order to protect against accidental damage to the infusion pump and/or accidental removal of the transcutaneous infusion cannula.

By way of example, Funderburk Jeffery V et al maintains that it is necessary to temporarily disconnect the pump from the patient whenever the patient is involved in an activity which may subject the pump to potential damage, and discloses a quick-connect coupling that permits temporary disconnection and subsequent re-connection of an infusion fluid source to a patient, without requiring removal of a transcutaneous infusion cannula from the patient, during bathing, showering, swimming or similar activities which may expose the pump to water damage (see Patent Literature 34).

In Patent Literature 35, Feldmann William G et al discloses an improved occlusion detector in an medication infusion pump to monitor medication delivery to a patient and to provide an early alarm in the event of medication nondelivery.

The occlusion detector includes a force sensor and a related control circuit for reading and comparing the pressure applied to the medication at a time corresponding with medication delivery to the patient and at a later time shortly preceding the next dosage. If the difference between the two pressure readings is less than a predetermined value, an occlusion is indicated and an alarm is activated (see Patent Literature 35).

In Patent Literature 36, Mann Alfred E et al discloses an infusion system for infusing a liquid such as insulin into the body. The infusion system includes an external infusion device and a remote commander. The external infusion device includes a housing, a receiver, a processor, and an indication device. The receiver is coupled to the housing and receives remotely generated commands.

The processor is coupled to the housing and the receiver to control the external infusion device in accordance with the remotely generated commands received. The indication device indicates when a command has been received and indicates when the command is being utilized to control the external infusion device.

With this configuration, the external infusion device can be concealed from view when being remotely commanded. The remote commander includes a commander housing, a keypad for transmitting commands, and a transmitter for transmitting commands to the receiver of the external infusion device (see Patent Literature 36).

In Patent Literature 37, Mann Alfred E et al further discloses a telemetered characteristic monitor system that includes a remotely located data receiving device, a sensor for producing signal indicative of a characteristic of a user, and a transmitter device.

The transmitter device includes a housing, a sensor connector, a processor, and a transmitter. The transmitter receives the signals from the sensor and wirelessly transmits the processed signals to the remotely located data receiving device.

The processor coupled to the sensor processes the signals from the sensor for transmission to the remotely located data receiving device. The data receiving device may be a characteristic monitor, a data receiver that provides data to another device, an RF programmer for a medical device, a medication delivery device (e.g., infusion pump) or the like (see Patent Literature 37).

In Patent Literature 38, Steven E. Wojcik discloses a low-profile infusion set for frequent or continuous subcutaneous injection of medication, which may remain in place for several days.

The infusion set includes a cannula housing adapted for mounting onto a person's skin and a needle housing adapted to for connection to the cannula housing. The cannula housing has a locking element positioned thereon. A cannula is connected to the cannula housing and extends therefrom. The needle housing has at least a first flexible sidewall and a resilient band connected to the sidewall for deformation upon deflection of the sidewall (see Patent Literature 38).

As described above, CSII is an injection method that involves sustained subcutaneous delivery of fast-acting insulin through the use of an insulin pump such as that disclosed by any of the above patent literatures, which insulin pump may be coupled to a tube.

The insulin pump is a cellular phone-sized automatic insulin infusion device, and an insulin formulation is injected through a catheter (a thin tube) subcutaneously inserted into the femoral or abdominal region. An example of another type of an insulin pump product is a small, insulin medication-containing pump that can be directly attached to the skin, where release of medication is wirelessly controlled.

In contrast to injection syringes that inject all of the medication at a time, insulin pumps are capable of automatic, sustained administration of low doses of insulin over 24 hours. This is believed to be equivalent to the basic insulin secretion in a healthy person.

The insulin pump system can be carried around all day in a clothe pocket or on the waist belt, and one may administer additional insulin e.g., before meals by turning on the switch of the main body. This is also believed to be equivalent to the basic insulin secretion in a healthy person.

Thus, the most significant advantage of CSII is its stable delivery of insulin. With typical insulin injection, sufficient insulin may not be supplied at a time immediately after injection or when the last medication is becoming ineffective thus leading to hyperglycemia. Conversely, when insulin is injected at peak efficacy, it may trigger hypoglycemia. CSII, by contrast, can relatively stablize blood glucose levels as it can deliver a controlled dose of insulin in a sustained manner.

In general, insulin secretion rate slightly changes during night sleep, and the dawn phenomenon—an abnormal early-morning increase in blood glucose level—has been the major challenge to be addressed in the treatment of diabetes, especially type-1 diabetes.

With CSII, insulin doses can be finely adjusted; a basic infusion dose can also be programmed before injection. This enables delivery of finely-controlled doses of insulin during night sleep, thereby solving the above issue.

There might be no problems if people with diabetics can spend life repeating the same pattern every day, e.g., eating meals of defined calories at defined times and receiving defined doses of insulin. In a real society, however, it is often difficult to spend such ideal life repeating the defined pattern over and over again.

Meanwhile, since CSII mechanically delivers insulin, failure to deliver insulin due to malfunction or clogging of the tubes immediately induces hyperglycemia, which may lead to life-threatening problems. This is the most serious concern with CSII.

It is therefore critical with CSII to self-monitor blood glucose levels by frequent blood glucose measurements along with checking of the CSII instrument. Moreover, patients receiving CSII therapy are required to acquire enough knowledge to deal with unexpected hyperglycemia, as well as to carry a normal insulin syringe and an insulin formulation all the time for possible insulin delivery failure due to pump trouble (see Non-Patent Literature 1).

Meanwhile, several companies are conducting research and development of inhalable insulin formulations and insulin inhalers, which are noninvasive (see Patent Literatures 39 and 40). More recently, orally absorbable insulin formations have been developed.

Further disclosed is an invention concerning an artificial pancreas in which (1) the CGMS that allows for continuous measurement of the glucose level in the interstitial fluid, (2) the insulin pump that can deliver controlled doses of insulin in a sustained manner to relatively stabilize the blood glucose level, and (3) algorithms for controlling the CGMS and insulin pumps are combined.

Wittman Uwe et al discloses an array and a method for dosing a hormone suitable for regulating the blood glucose, especially insulin, of a diabetic patient.

With reference to the representative relationship diagram, Wittman Uwe et al discloses an array for dosing a hormone suitable for regulating blood glucose of a patient, the array including (A) a measuring device for detecting measured values correlatable with blood glucose; (B) a controlling section which comprises a controller to process the measured values according to a control algorithm and a hormone dosing unit to administer a hormone dose, and (C) a pilot control device acting on the controlling section to reduce the dead time of the control.

According to a particularly preferred embodiment of the Wittman invention, the degree of physical activity of the diabetic is taken into consideration by the pilot control device having an activity measuring unit for the sensory detection of the degree of physical activity of the patient. In order to detect resting states of the patient such as lying, sitting or standing, an advantageous embodiment provides the pilot control device with a position sensor, in particular a mercury switch or spirit level.

In order to detect states of exercise, it is advantageous that the pilot control device has a motion sensor, in particular a pedometer. Also with regard to an indirect detection of physical strain it is advantageous that the pilot control device has a sensor for detecting body parameters of the patient such as heart rate, body temperature or skin conductivity.

Furthermore, Wittman Uwe discloses that the array illustrated in the drawing enables an automatic regulation of the blood glucose of a diabetic patient. The array is disclosed as being essentially composed of a controlling section for the fine adjustment of insulin administration, a pilot control device for the coarse pre-control of the controlling section in accordance with at least one influencing or disturbing variable which influences the blood glucose level of the patient, and a measuring device for the sequential detection of measured values correlated with the blood glucose level.

The array is additionally provided with a motion sensor. A pedometer can be employed as such a motion sensor to quantify physical activity levels during walking or running. A further additional sensor is used to detect body parameters of the patient which at least indirectly allow conclusions about physical activity, i.e., in particular heat beat frequency, body or skin temperature and skin conductivity.

According to a further advantageous embodiment, the measuring device has a glucose sensor which preferably utilizes microdialysis technology to detect tissue glucose values as measured values.

This allows a continuous detection of the regulating variable without having to maintain a direct access to the blood circulation. Wittman Uwe discloses that the pre-control is particularly advantageous in this regard since the glucose transfer between blood and tissue occurs with a certain delay.

The blood glucose level is not measured directly due to the difficulties of a permanent intravenous access, but rather the correlatable tissue glucose level in the subcutaneous fatty tissue of the patient is measured. For this purpose the measuring device has a glucose sensor which utilizes microdialysis technology in a known manner. For this a microdialysis probe implanted in the tissue is supplied with a perfusion liquid and the glucose content is detected sequentially by an electrochemical-enzymatic electrosensor connected downstream. The measured values can be derived quasi-continuously or at intervals.

Wittman's glucose sensor may correspond to the above-described CGMS, although not clearly indicated. The dosing unit may be formed as an insulin pump which enables an automatic subcutaneous insulin application via an infusion cannula for example in the stomach region. The microdialysis probe as well as infusion cannula can be implanted by the patient himself without medical supervision.

The time delays occurring in the control due to transfer from blood to subcutaneous tissue can be managed without problems by the proposed control strategy. The entire control array can be accommodated in a portable instrument carried on the body of the patient which thus undertakes the function of the pancreas for normoglycaemic metabolic control. The dosing unit may be formed as an insulin pump (see Patent Literature 41).

However, using any control algorithm, the Wittman's measuring device for detecting measured values correlatable with blood glucose inevitably entails time delays associated with glucose transfer from blood to the interstitial fluid.

Moreover, the Wittman invention employs a configuration wherein "a microdialysis probe implanted in the tissue is supplied with a perfusion liquid and the glucose content is detected sequentially by an electrochemical-enzymatic electrosensor connected downstream," which configuration further increases time delays. It remains skeptical that measured values follow blood glucose rise after a meal, which should be strictly controlled particularly during the treatment of diabetes.

Control algorithms based on measured values measured in the presence of time delays are not practical for insulin dosing. Further, the Wittman invention fails to describe the following points.

Specifically, the Wittman invention remains silent with respect to how the control algorithms specifically control insulin dosing while considering the required insulin dose that changes from moment to moment depending on the onset time lag, body weight, emotional stress or disease (especially infectious disease).

However, the Wittman's attitude toward solving the foregoing problems as much as possible with the "pilot control device" that measures "the degree of physical activity of the diabetic" is commendable. It still remains skeptical whether many of the foregoing problems can be resolved with a "position sensor, in particular a mercury switch or spirit level," "motion sensor, in particular a pedometer" or "a sensor to detect body parameters of the patient which at least indirectly allow conclusions about physical activity, i.e., in particular heart beat frequency, body or skin temperature and skin conductivity."

Wittman's efforts to improve control accuracy as much as possible by employing a "position sensor, in particular a mercury switch or spirit level," and a "sensor to detect body parameters of the patient which at least indirectly allow conclusions about physical activity, i.e., in particular heart beat frequency, body or skin temperature and skin conductivity" in a multi-sensor device (later described) can be understood.

However, the sensors for detecting body parameters need to be closely attached to the body all the time and therefore are awkward to use. Moreover, these sensors increase the product price. Considering burgeoning medical costs facing the governments around the world, high-price products are not ideal.

It should be concluded from the description "it is advantageous that the pilot control device has a motion sensor, in particular a pedometer for the detection of exercise" that the Wittman invention underestimates the side effects of physical activities as will be described later; it cannot be said "advantageous" in view of the fact that diabetic patients entrust their life to the artificial pancreas. From these points of view, there is no choice but to conclude that the Wittman invention is nothing more than words on paper.

Finally, the difference between "living activity" as used in the present invention and "physical activity" as used in the Wittman invention will be clarified below.

The Wittman invention employs "a motion sensor, in particular a pedometer" for the detection of states of exercise. "Living activity" according to the present invention are activities whose energy expenditure is defined by the so-called non-exercise activity thermogenesis or NEAT—energy expended in daily activities not designated as exercise. More specifically, daily living activities include activities such as sleeping and eating, other than exercise. It is particularly emphasized that "living activity" as used in the sense of the present invention and "physical activity" as used in the Wittman invention are totally different. It should be noted that daily living activities cannot be detected with a pedometer.

About a year and a half after the application of the Wittman invention, Kitaguchi filed an application concerning an invention relating to artificial pancreas, which is substantially the same as the Wittman's invention (see Patent Literature 93).

Herein, the Kitaguchi's invention will not be described in detail as it is identical to the Wittman invention. The Kitaguchi invention is novel over the Wittman invention in that a medical practitioner can wirelessly monitor the control state of the patient's blood glucose level.

The DAWN Study in 2001, a comprehensive survey of stakeholders in diabetes, reported that the average consultation time per day in Japan is the shortest among the countries surveyed; the current situation in Japan is that each diabetic patient cannot be adequately consulted.

In 2005, according to the Ministry of Health, Labor and Welfare of Japan, 7 million Japanese people are presumed to suffer from diabetes, causing a severe squeeze on the Japan's medical insurance system. In view of this circumstance, it is not feasible for medical practitioners to determine the dose of insulin with reference to the patient's blood glucose level or history of blood glucose control (see Non-Patent Literatures 15 and 16).

It is also disclosed that instruments can be interconnected by near-field wireless communication, eliminating the need to install them in one device (housing). Based on the inventions described above, Insulet Corporation and Medtronic Inc. have already developed and commercialized a small-sized insulin pump that performs near-field wireless communication and a small-sized CGMS transmitter, respectively, in the U.S. and other countries (see Patent Literatures 27, 28 and 31-37).

The CGMS and insulin pumps described above have not yet been frequently used in clinical sites; these devices are used by only a fraction of diabetic patients, which is too far from the objective of the Japan Diabetes Society.

One possible reason for this is that since diabetes is chronic disease that entails no pain, diabetic patients find monitoring of blood glucose level burdensome and thus are reluctant to go to hospital or receive insulin therapy, even when their medical conditions are getting worse. Moreover, the fact that many of the diabetic patients are older and HBA1c level increase due to aging should be taken into account. However, diabetic patients are less willing to receive such a therapy that entails changes in living environments e.g., dietary pattern or exercise pattern. Due to recent trends toward nuclear families, it would be difficult for family members to encourage a diabetic family member to receive insulin therapy.

Failure to support diabetes treatment in light of the life pattern or detailed record of daily changes in blood glucose level in the Japan's medical insurance system may be responsible for the elevated HBA1c levels in diabetic patients.

At present, no instruments are available that enable medical practitioners to record daily living activities of diabetic patients to monitor their life patterns. As general instruments that record physical activities, Manpo-Kei® (pedometer), accelerometer, heart rate monitor, GPS monitor, multi-location device, multi-sensor device and the like are commercially available, each of which will be described below.

A pedometer is a non-expensive device that can readily record daily living activities. It generally counts footfalls, and therefore, cannot detect physical activities that entail no foot motions, e.g., anaerobics such as weight lifting, bicycle exercise and daily activities (see Non-Patent Literatures 17 and 18).

It is also reported that pedometers cannot measure step counts and traveled distance accurately even during walking (see Non-Patent Literatures 17).

Even expensive pedometers have an error of 30% in terms of energy consumed by walking (see Non-Patent Literatures 19).

In Japan, it has been reported that a pedometer or step counter was developed by Hiraga Gennai around 1775. A pedometer is designed to detect oscillations transmitted to the device with an oscillation sensor and, based on the detection outputs, to count the number of frequency, or steps.

Pedometers are disclosed in which, in the sensor section, a pendulum is biased upwardly by a spring so that the pendulum swings vertically along with vertical walking motion, that a conduction signal is generated at the time when the pendulum contacts the contact point in the down motion, and that the signal is electrically processed in an electric circuit to count a step (see Patent Literatures 42-44).

As pedometers that process step count data, for example, pedometers that record step count trend-waves are available.

Patent Literature 45 discloses a pedometer that displays not only step counts, but a graph that shows daily changes in step count on the screen.

Patent Literature 46 discloses a pedometer that includes a step counter section and a main body, wherein the step counter section has step counting means having a function of storing step count data, and attachment means, and wherein the main body has calculation means and display means. The step counter section and the main body are so configured that when they are detachably coupled together, the data stored in the step counting means is transferred to the calculation means of the main body.

Other examples include exercise amount display systems that visually notify the user of traveled distance and calorie consumption for increasing motivation toward walking exercise (see Patent Literature 47).

Further, pedometers are disclosed that include an input device, a storage/calculation device and a display device for body parameters (e.g., age, gender, height and weight), and a step count detection device, for measuring step counts and then calculating and displaying the amount of energy consumed in terms of amount (e.g., grams, bowls, cups, etc.) of food such as rice, liquor or noodle (see Patent Literature 48).

Examples of pedometers that can count an additional parameter are those capable of measurement of pulse waves.

Examples thereof include pedo-pulse meters and pedometers that can detect pulse waves and steps with the same sensor (see Patent Literatures 49 and 50).

A device is also disclosed in which a pedometer function and a radio receiving function using a compact frequency synthesizer are realized as a single device (see Patent Literature 51).

Patent Literature 52 discloses a portal wireless transmitter including communication means. The portable wireless transmitter disclosed by Patent Literature 52 includes time calculation means for calculating lapse time, wireless signal transmitting means for transmitting a wireless signal, control means for controlling these means, and step counting means of counting the steps of the user who carries the portable wireless transmitter.

The control means regularly transmits the step count, which has been counted for a predetermined time period based on the output of the time counting means by the step counting means, to the wireless signal transmitting means.

In addition, Patent Literatures 53 and 54 disclose vital data collection/display devices that collect vital data from externally mounted vital sensors such as a manometer, a thermometer, an electrocardiographic monitor, a weight scale, a pedometer, and/or a body fat scale, for displaying on the display.

The devices disclosed by Patent Literatures 53 and 54 has a vital sensor collection table and a display layout changing function. The vital sensor collection table is used for the selection of a vital sensor from which vital data is to be retrieved and displayed on the display, among the vital sensors externally mounted. The display layout changing function optimizes the display layout, which is displayed on the display in accordance with the content of the vital sensor collection table, so that the display area becomes large enough to allow for easily recognition of the displayed data.

When using a portable a manometer with a pedometer, changes in patient's blood pressure are measured around the clock using a function of a cellular phone.

In this continuous blood pressure measuring method, a patient carries a manometer all the day, so that the measured value is regularly transmitted to the information management server with a data communication function of the cellular phone, whereby the patient's health condition is monitored by checking blood pressure changes along with the step count displayed on the pedometer (see Patent Literatures 53 and 54).

Patent Literature 55 also discloses an instrument in which a pedometer and a body fat scale are integrated. The instrument disclosed by Patent Literature 55 has a function of displaying step counts and calorie consumption, and a function of displaying a measured body fat percentage and a body fat mass. The pedometer counts steps and measures calorie consumption based on the step counts, step pitch (time per step) and body weight. The instrument judges the user's degree of obesity based on the body fat percentage, age, and sex, and calculates and displays a daily calorie target based on the obesity judgment in consideration of the user's age.

Patent Literature 56 also discloses a health/step count management instrument in which step counting means is incorporated. The instrument disclosed by Patent Literature 56 includes a portable housing having a display section; a pair of body impedance measuring electrodes disposed on the surface of the housing; data input means for receiving input of personal data selected from sex, age, body height and body weight; and body fat percentage calculating means of calculating an actual body fat percentage based on a body impedance generated when a small current is sent through the body with the electrodes and on the personal data input via the data input means. In addition to step counts, body fat percentage is displayed on the display section.

More recently, Manpo-Kei® (pedometer)-incorporated writing materials for detecting rotary motions, and pedometers for water walking are disclosed (see Patent Literatures 57 and 58). It can be therefore concluded that pedometers are devices designed for healthy people, which can measure exercise amount and step counts at low costs.

An accelerometer is a device that can measure daily living activities more accurately and readily than pedometers. It measures the acceleration relative to a certain axis. It is reported that accelerators use piezoelectric elements, micromechanical springs, capacitance changes or the like (see Non-Patent Literature 20).

Patent Literature 59 discloses a portable exercise amount measuring device as an accelerometer for walking. The device is carried by a subject and calculates and displays an exercise amount. With reference to the drawing, the user's motion is detected by a 3-axis acceleration sensor.

Patent Literature 60 discloses a pedometer that converts oscillations during walking or running into voltage with piezoelectric elements, and counts through a counter circuit the number of times that the voltage exceeded a set value within a predetermined time period.

Patent Literature 61 discloses an electronic device having an accelerometer. The electronic device disclosed by Patent Literature 61 pre-sets a target travel amount by target value setting means and, after the user has started to move, compares the travel amount being measured by measuring means with the target travel amount. For example, different image data are displayed at different measured travel amounts, e.g., the measured value is far below, below, or over the target value.

Patent Literature 62 discloses a sensor structure of a pedometer that enables accurate step counting. In the sensor structure of the pedometer disclosed by Patent Literature 62, a pair of vertically opposing magnets is provided, with the lower magnet being immobilized and the upper magnet being movably retained, and magnetic force detecting means is provided that detects magnetic force generated by the vertical movements of the movable magnet.

Patent Literature 63 discloses a pedometer capable of step counting without having to be worn on the waist belt. The pedometer disclosed by Patent Literature 63 includes two perpendicularly crossing acceleration sensors in the main body which are supported swingably in vertical direction and horizontal direction, respectively, and an angle detection sensor for detecting the tilt angle of the main body with respect to the ground. The pedometer counts steps by selecting one of output signals respectively of the two acceleration sensors based on the angle signal detected by the angle detection sensor.

The pedometer is disclosed as being capable of counting steps regardless of the orientation of the device or user's posture, so that the user can carry the device in any way, e.g., in a pocket or bag, in addition to slacks/skirt belt.

Patent Literature 64 discloses a pedometer that includes in a case a vertically movable piezoelectric sensor provided so that the sensing surface thereof collides against a collision surface of the case for each step by the vertical acceleration. The pedometer includes in the case an operational amplifier that amplifies output voltage of the piezoelectric sensor, and a calculator that calculates the collision count of the piezoelectric sensor by superimposing output voltage prior to collision with output voltage at collision. The pedometer further includes a display device on a side wall of the case, for displaying thereon a collision count determined by the calculator.

As a pedometer which can count steps reliably, Patent Literature 65 discloses a pedometer in which the reliability of an electric contact between a sensor contact and a contact section is improved.

Additionally, Patent Literature 66 discloses a pedometer that includes an acceleration sensor, information input means, calculation means for calculating step counts or calorie consumption, and a display. The pedometer disclosed by Patent Literature 66 sets multiple step count threshold values for each of the frequency component respectively of X-, Y- and Z-acceleration direction output signals from the acceleration sensor.

Patent Literatures 67 and 68 disclose a pedometer that includes a counter module composed of a magnetism sensing element section and a movable magnetic section. The movable magnetic section is composed of a magnetic held by an elastic member, and a guide member that allows the magnetic to move in a predetermined direction.

The pedometers disclosed by Patent Literatures 67 and 68 include at least two pendulums and count oscillations of the pendulums as step counts, wherein different pendulums have different thresholds for sensing oscillation. The pedometers not only count steps (e.g., walking steps) but measure intensity of exercise.

Commercial accelerometers currently available in the market rely on MEMS to convert mechanical energy into electrical signals to calculate living activity levels, and come in various forms, including those incorporated into wristwatche-type, pedometer-type, music player-type or sports shoes with a built in accelerometer. However, the accelerometers often simply display a figure calculated by multiplying the number of accelerations by a certain coefficient value—a calculation formula focused on the measurement of physical activities (e.g., walking or running) rather than on accurate recording of daily living activities. Thus these devices are not suitable for recording of general daily living activities (see Non-Patent Literature 21).

As part of exercise prescription, heart rate monitors are commercially available that can record physical activities based on vital signs (see Non-Patent Literature 21).

The technology that enables easy heart rate measurement comes in two types: electrocardiography using electrodes to put on the breast, and infrared-based blood stream measurement. The former method measures heartbeats by detecting cardiac potential, and the latter method measures heartbeats by detecting blood stream changes. Each method measures heart rate based on beat-to-beat intervals.

For example, the following literatures concern a heart rate measuring instrument, more particularly to a small portable heart rate measuring instrument that can measure and store heart rate as well as can store measurement times. Patent Literature 69 discloses cardiac potential leading electrodes as well as the principle underlying heart rate measurement.

Patent Literature 70 discloses cardiac potential leading electrodes, one for attachment to facial skin and the other for attachment to part of the right or left hand. The cardiac potential leading electrodes disclosed by Patent Literature 70 are used in electrocardiographic heart rate meters that use the electrode of two different points put on the body surface to detect cardiac potential, to measure beat-to-beat intervals and display the number of heartbeats per minute on the display.

Patent Literature 71 discloses a simple wristwatch-type electrode heart rate meter that includes a main body; securing means for securing the main body to the user's arm with its back surface facing the body; a 3-axis acceleration sensor for detecting accelerations as vector quantities in the directions of x, y and z axes; a first electrode provided at the back surface of the main body and contacts the body surface; and a second electrode provided on the main body and can be touched with a finger.

The electrode heart rate meter includes means of detecting cardiac potential and means of calculating exercise amount by converting accelerations in the directions of x, y and z axes into scholar quantities as well as calculating heart rate based on the cardiac potential. The electrode heart rate meter further includes means of storing the calculation result by the calculating means, and a display section which is provided at the surface of the main body and on which the calculation result is displayed. The user can readily confirm the intensity of exercise.

In particular, the 3-axis acceleration sensor enables the electrode heart rate meter to detect motions performed in every directions without having to provide additional sensors. Thus, the sensor space can be minimized compared to traditional devices that use two or more acceleration sensors for exercise intensity measurement. Thus, one can carry the device as a small wristwatch without feeling any discomfort. The device is illustrated in the drawing as being capable of continuous monitoring without providing any discomfort or feeling of restriction even when the user carries the device for a long time (e.g., all the day).

By employing a vital sign-based recording method for physical activities, it is possible to measure the amount of bicycle exercise, which cannot be measured with a pedometer or accelerometer. Moreover, with this recording method, false counting due to shaking, riding in a car or train, etc., can be avoided. When measuring heart rate, however, false counting occurs as it varies depending on stress, mood swing, coffee intake, environmental temperature, medical condition, etc (see Non-Patent Literatures 22 and 23).

Moreover, since heart rate increases in proportional to the degree of load on the body in moderate and vigorous exercises (see Non-Patent Literature 24), it is not suitable as a measure of general living activity.

GPS monitors that can calculate energy consumed during walking, running, cycling, etc., based on the moving speed and distance are commercially available. These devices, of course, are not suitable for recording of general living activity.

A multi-location device means a system composed of multiple accelerometers to be attached at different points of the body. The multi-location device allows for use of accelerometers not only for the measurement of a specific physical activity (e.g., walking or running), but also in a cycling machine.

A multi-sensor device means a system that accurately records living activity using combinations of the above instruments. Commercially available multi-sensor devices come in a variety of combinations, including an accelerometer and a heart rate meter, and a heart rate meter and a GPS.

For example, the multi-sensor device is a portable terminal that includes a physical condition measuring section for measuring the user's physical condition; a GPS receiving section for receiving the positional data of the user; a transmitting/receiving section for communication by accessing wireless connections; a memory section for storing pre-set reference physical information data; and a control section for controlling the above sections.

The portable terminal stores in the memory section destination information; message data to be sent to the destination; and a monitoring program that receives data of physical information of the user from the physical condition measuring section and causes the control section to compare the reference data stored in the memory section and the received data.

The control section executes the monitoring program. More specifically, when a predetermined result is obtained as a result of the comparison between the reference data and measured value data, the control section executes processing of extracting message data stored in the memory section, generating a sending message based on the extracted message data and the positional data detected by the GPS receiving section, and automatically sending the generated message to the destination previously stored in the memory section via the wireless transmitting/receiving section.

The physical condition measuring section of the portable terminal includes a pulse measuring section for measuring pulse of the user, and a heartbeat measuring section for measuring heartbeat of the user, wherein the control section calculates blood pressure based on the measured values respectively of the pulse measuring section and heartbeat measuring section (see Patent Literature 72). This device, however, is not suitable for recording of general daily activities as it costs over 100,000 yen.

Patent Literature 73 discloses a plurality of accelerometers as well as a system for detecting, monitoring, and reporting human physiological information, such as body temperature changes, skin voltage, skin temperature, environmental temperature and pulse rate. The following describes the system disclosed by Patent Literature 73.

The system includes at least one of an accelerometer, a GSR sensor, and a heat flux sensor. The system further includes a sensor device adapted to be placed in contact with an individual's upper arm and is adapted to generate data indicative of at least one of activity, galvanic skin response and heat flow of the individual. The sensor device may also be adapted to generate derived data from at least a portion of the data indicative of activity, galvanic skin response and heat flow. The system generates analytical status data from at least one of the data indicative of at least one of activity, galvanic skin response and heat flow and the derived data, remote from the sensor system.

The system includes a central monitoring unit that includes a data storage device for retrievably storing at least one of data indicative of at least one of activity, galvanic skin response and heat flow, derived data, and analytical status data. The system further includes data transfer means that establishes electronic communication between the sensor device and the central monitoring unit, and means for transmitting the data indicative of at least one of activity, galvanic skin response and heat flow, the derived data, and the analytical status data to a recipient.

Referring to FIG. 1 of the literature, located at the user location is a sensor device adapted to be placed in proximity with at least a portion of the human body. The sensor device is preferably worn by an individual user on his or her body, for example as part of a garment such as a form fitting shirt, or as part of an arm band or the like. The sensor device includes one or more sensors, which are adapted to generate signals in response to physiological characteristics of an individual, and a microprocessor.

Proximity as used herein means that the sensors of the sensor device are separated from the individual's body by a material or the like, or a distance such that the capabilities of the sensors are not impeded.

The sensor device generates data indicative of various physiological parameters of an individual, such as the individual's heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and UV radiation exposure and absorption.

In certain cases, the data indicative of the various physiological parameters is the signal or signals themselves generated by the one or more sensors and in certain other cases the data is calculated by the microprocessor based on the signal or signals generated by the one or more sensors. Methods for generating data indicative of various physiological parameters and sensors to be used therefor are well known.

Table 1 of Patent Literature 73 provides several examples of such well known methods and shows the parameter in question, the method used, the sensor device used, and the signal that is generated. Table 1 also provides an indication as to whether further processing based on the generated signal is required to generate the data.

Similar inventions are also disclosed by the same Applicant (see Patent Literatures 74-82). As with the above multi-location device, the devices disclosed in these literatures are not suitable for recording of general daily activities at they cost over 100,000 yen.

One problem common to all of the above-described devices is that users do not continue exercise using the device. While it is important to continue exercise at intensity suitable for each individual, it cannot be said that the above devices have succeeded in solving this problem.

As a technology aiming to increase motivation toward continued use of an exercise recordable device, Patent Literature 83 discloses an exercise amount display system that visually notifies the user of traveled distance and calorie consumption during walking to increase motivation toward walking exercise.

Patent Literature 84 discloses a pedometer that counts steps based on oscillations or other parameters during walking and then calculates and displays the traveled distance based on the step counts and the pre-set stride length value. The pedometer offers a virtual trails system so that the user can exercise as if he/she walked in an actual area. The pedometer thus can encourage users to continue walking.

Patent Literature 85 discloses a system for controlling exercise amount. The system pre-sets a target travel amount by target value setting means and, after the user has started to move, compares the travel amount being measured by the measuring means with the target travel amount. For example, different image data are displayed at different measured travel amounts, e.g., the measured value is far below, below, or over the target value. The literature discloses that when the system is used in an electronic pedometer, users can enjoy controlling their exercise amount because total step count is displayed in connection with image data.

Patent Literature 86 discloses a game device having an exercise amount receiving function. The game device disclosed by Patent Literature 86 includes an exercise amount measuring device such as a pedometer which calculates and displays the travel amount and walking speed; transmitting/receiving means which is provided to the exercise amount measuring device and transmits exercise amount data measured by the exercise amount measuring device; and receiving means for receiving the data sent from the transmitting/receiving means.

The game device includes control means of controlling the level of a game character by searching for a character having a level corresponding to the exercise amount data sent from transmitting/receiving means among programmed characters; and transmitting means of transmitting, upon completion of transmitting of the exercise amount data measured by the transmitting/receiving means, reception completion signals to the transmitting/receiving means.

The game device can control levels of game characters using data sent from the exercise amount measuring device such as a pedometer which calculates and display the travel distance and walking speed.

In order for a user to select a high level character, a certain amount of exercise should be performed in advance. This encourages children and adults in today, who tend to lack exercise, to exercise more frequently. It is also disclosed that the game device can improve reflexes and thus the ability of the player, enabling the player to enjoy the game device in many different ways.

Patent Literature 87 discloses a portable toy which uses a pedometer. The portable toy disclosed by Patent Literature 87 made it possible to convert step counts into a graphical depiction by using switching signals generated by walking. The device is an intellectual toy that allows a user, even when reached only midway to the destination, to imagine or learn landscapes, customs, feelings, etc., of a specific region or era by observing a graphic created based on the travel distance.

The portable toy measures travel distance by multiplying switching counts by stride length. The device stores virtual trails, such as "Oku-no-Hosomichi Tour", "Major City Tour, from Hokkaido to Okinawa", "The 88 Temple Pilgrimage Tour" or "53 Stations of the Tokaido Tour." These trails help users to set their respective goals, encouraging them to continue health management with a fun.

Similarly, Patent Literature 88 discloses a game device which has a game function and a pedometer function. The game device disclosed by Patent Literature 88 changes the form of a character, displayed on the display section, over time and in association with the user's performance, i.e., step counts measured by counting means. For example, a user can make virtual friends with the displayed character. It is disclosed that, whether inside or outside the house, player's healthy activities may be actively reflected on the form of the character displayed on the display section.

Patent Literature 89 discloses a portable game device equipped with a pedometer. The portable game device disclosed by Patent Literature 89 displays steps counts on a daily, weekly or monthly basis. With the game device, a user can gain a sense of achievement e.g., daily, weekly or monthly. In this game various landmark objects are placed on a walking trail, so that the player can be notified that he/she has reached a particular point via a message or action of a game character displayed. This allows the player to attain a sense of achievement for the landmark objects he/she reached, i.e., the distance the player has walked on the day.

Patent Literature 90 discloses improvements on amusement-oriented pedometers in attempts to remove boringness of conventional pedometers as well as possible health harms from amusement-oriented pedometers due to faster paced walks. The device disclosed by Patent Literature 90 judges and displays pace appropriateness. When the step count has reached a certain number, the user plays a game that determines pace appropriateness, the result of which is reflected in the score. With this configuration, it is possible to encourage users to continue waking exercise without entailing boringness or excess exercise.

Patent Literature 91 discloses a game device which can be enjoyed also by older people. As one possible application, the game device also allows older people to enjoy training for health management or rehabilitation.

The motivation-related inventions currently disclosed all end up describing simple calorie calculations, games or step count goals, rather than describing how continuous device use can be utilized for the maintenance of good health. Accordingly, these devices ignore essential issues and thus would not be used in a continuous manner.

For continuous device use, it is critical to facilitate continuous use by mounting the device in question on a device worn by a user all the time, e.g., cellular phone, as well as to make users realize that exercise and health go hand in hand. The above literatures describe in detail only exercise of healthy people, and thus the inventions therein are different from the present invention directed to a device for recording daily living activities of diabetic patients.

One example of a system in which the above prior art technologies are combined may be the following system directed to people who wish to maintain good health, which system reliably records energy consumption during exercise, physical information, etc., while controlling energy intake, and medications and doses.

This system is directed to at least adult disease patients, people who wish to maintain good health, and people who wish to lose weight, and helps them self-monitor daily life, dietary and exercise. The system includes a portable reader which reads information designated at least by a design or number and sends the information to another device; and display means of energy consumption measured by sensing motions of the human body and measuring energy consumed during exercise.

The system includes a portable exercise amount measuring device; a storage device which can be attached to and detached from another device and which can read or write information from or to the attached device; a radio communication device which can be attached to and detached from another device and which can wirelessly transmit or receive information to or from the attached device; and means of connecting the above devices together.

The system further includes a plurality of portable computers, each including information processing means, information storing means, manual information input means, and information display means; a database which stores therein food information, personal information, medical information such as medication history in medical institutions or prescription, and general information, the database adapted to be placed in a management facility of this system.

The system further includes a main server including information processing means, information display means, manual information input means and communication means; and a plurality of network computers, each capable of transmitting or receiving information to or from the main server and including information processing means, information storing means, manual information input means and communication means, the networks adapted to be placed in a plurality of medical institutions for treating the users or prescribing or instructing health management.

The system further includes a database adapted to be placed in a plurality food supply facilities such as restaurants or drug stores, the database storing therein information indicating the amount of calories of each nutrient contained in food provided by food supply facilities; and radio communication means that can transmit or receive information to or from the radio communication device of each portable computer.

The system further includes a plurality of personal servers, each including information processing means, information display means, communication means and manual information input means; a cellular phone that enables transmission or receipt of information at least between the main server and each portable computer; and a cellular phone communication network.

The system further includes a communication network such as a digital communication network or the Internet used for communication among the main server, network computers and personal servers, and provides a design- or number-based search code unique to each database of the personal servers placed in the food supply facilities.

The system further includes a menu of items; and a plurality of physical condition measuring devices such as manometers, blood glucose meters and/or body fat scales, wherein the devices are adapted to be placed in the medical institutions and user houses, include connection means of the storage device, employ the storage device as information transmission media, and can transmit or receive information to or from the network computers and portable computers.

The system further includes a plurality of exercise assist instruments such as room runners, wherein the instruments are placed in user houses, include connection means of the storage device, employ the storage device as information transmission media, and can transmit or receive information to or from the portable computers.

The management facility stores, in the database of the main server, fundamental information unique to each user, such as daily exercise amount prescribed or instructed by a medical institution, the amount of calories of each nutrient at breakfast, lunch and dinner, medications and doses, and physical condition measurement times.

The management facility constructs a personal information database, and sends personal information stored therein to the plurality of portable computers which the users carry and for which the portable storage media is used as a transmission media.

The management facility stores at least history of medical treatment, prescriptions and examination information in medical institutions, to construct a medical information database. The management facility provides network computers placed in medical institutions with either or both of stored information and a program for displaying the information.

The management facility further construct an ingredient information database by storing at least information indicative of the amount of calories of each nutrient (e.g., sugar, protein, lipid, mineral and vitamin) per unit weight of each of ingredients.

The management facility then causes the processing means of the main server to process information regarding cooked foods, cooking methods of processed foods, types and weights of ingredients, with reference to ingredient information stored in the ingredient information database (i.e., information indicative of the amount of calories of each nutrient per unit weight of each ingredient) to calculate the amount of calories of each nutrient contained in cooked food or processed food, and sends calculations to the personal servers placed in the food supply facilities.

The user carries the exercise amount measuring device to measure the amount of energy consumed during daily life. The user then inputs the measured value to the portable computer as needed.

The portable computer determines whether or not the input amount of energy consumption exceeds the target amount prescribed at least by a medical institution, and displays the result on display means as well as stores the same in the information storage means.

When the user eats a home-made meal to obtain energy of nutrients in accordance with the calories displayed on the display means of the portable computer, the user makes reference to a food menu provided at least by the medical institution.

The user then inputs the amount of calories intake to the portable computer with the manual information input means, whereby the amount of calories of each nutrient intake is displayed on the display means and is stored in the information storage means.

The user also obtains the above energy from cooked food provided at food supply facilities.

In this case, the user uses a reader of the portable computer to read a search code, which is designated at least by a design or number in a menu of the facility and is unique to each food name. This causes the search information to be transmitted to the personal server placed in the food supply facility via the wireless communication device of the portable computer. With this search information, the personal database is searched for appropriate information, which is transmitted to the portable computer.

When the user obtains the above energy from processed food purchased from the food supply facility, the user uses the reader of the portable computer to read a barcode on the processed food. This causes search information to be transmitted to the personal server placed in the food supply facility via the wireless communication device of the portable computer.

The personal server searches its database for appropriate information, and corresponding information is transmitted to the portable computer.

The portable computer compares the information transmitted from the personal server, i.e., the amount of calories of each of nutrients contained in cooked food or processed food with those prescribed by a medical institution, and stores in the storage means information indicative of excess or deficiency of calories from the cooked food or processed food. The portable computer also displays the information on the display means.

This encourages the user to determine whether or not to eat the cooked food or processed food, or to determine the amount of acceptable calories. The portable computer notifies the user of a body parameter to be measured and measurement time via the display means based on the prescription of a medical institution or the like.

As described above, the daily life/health management system and method of operating the same disclosed by Patent Literature 92 allow a user to easily and reliably monitor and record the amount of energy consumption, measured physical condition values, amounts of calories of nutrients intake, and medications and doses, as prescribed or instructed by a medical institution.

Patent Literature 92 discloses that the system is targeted to would-be adult disease patients who need daily life monitoring, as well as to those who wish to maintain good health or lose weight in a healthy manner, and that the system helps those people to easily and reliably monitor or record the amount of energy consumption, measured physical condition values, amounts of calories of nutrients intake, and medications and doses, as prescribed or instructed by a medical institution, while controlling the operations.

The Isomura invention is directed to a system that allows a plurality of devices to communicate with one another, which is extremely fascinating in that information is automatically managed. However, it costs too much for individuals to buy devices supported by this system one by one. Moreover, it is likely that huge efforts will be needed from both public and private sectors before establishing an information infrastructure. There is also concern over the handling of personal information by this system, for example. Furthermore, a major drawback of the Isomura invention is that the inventor focused on acquisition, provision, utilization, etc., of information so much that they totally failed to describe human connections among users—which is important in health management or blood glucose control.

Beginning fiscal year 2008, with the ever-increasing prevalence of metabolic syndrome, the Ministry of Health, Labor and Welfare of Japan has started to require insured persons to receive special health checkups and health care guidance. Under this circumstance, companies from various fields, including health care, exercise machine and amusement, are developing various metabolic syndrome-related services.

The most difficult challenge was that how we can keep the user's motivation high. Many of the services conclude that the key is human connection (e.g., connections among users, or connections between the service provider and user). Isomura fails to discuss the most important points—why users can use the system continuously, and how the system keeps the motivation high.

Moreover, the Isomura invention differs from the present invention in the following points: All devices are set apart from one another; medical practitioners confirms the collected information using a different device than the one used for measuring; exercise is measured rather than daily living activities; and forth. Moreover, Isomura provides no detailed description of system units (e.g., instruments or devices) required; therefore, with the Isomura invention, the essential user needs have not yet been met. Accordingly, it can be concluded that the Isomura's system, where information is merely transmitted from one device to another, is nothing more than words on paper.

Additionally, a biological signal measuring device is disclosed that includes a main body having a palm support formed on an upper surface; a sensor section formed on the palm support for measuring biological signals of a subject, the sensor section including an electrode that is adapted to electrically contacts the palm of the subject; and a calculation section which is formed in the main body and receives signals from the sensor section to perform predetermined calculations. The sensor section may include a blood pressure cuff for measuring blood pressure at a finger.

Patent Literature 94 discloses an exercise plan proposing device for supporting users to improve body parameters by exercise. The exercise plan proposing device disclosed by Patent Literature 94 includes exercise plan generating means for calculating the intensity of exercise and exercise time that are needed to achieve a set target body parameter within a set exercise period; and exercise plan output means for displaying the calculated intensity of exercise and calculated exercise time to the user.

Patent Literature 95 discloses a user's health management method in a health management system. The method used in the health management system disclosed by Patent Literature 95 includes a step of maintaining a first database storing therein medical interview questions as well as a second database storing therein average physical condition information; a step of presuming the current physical condition of the user; and a step of comparing the current physical condition and average physical condition information with reference to the second database, to detect any changes in the body parameters of the user.

The user's health management method further includes a step of referencing the first database to output lifestyle question information associated with changes in the body parameters; a step of receiving, from the user, input of information regarding an answer to the lifestyle question; a step of analyzing user's physical condition based on the measured current physical condition and the information regarding an answer to the lifestyle question; and a step of reporting information regarding user's physical condition in accordance with the analysis result.

By presenting information of the user's health condition analyzed by the health management system by means of diagrams or graphs, the user can visually manage his health condition. Moreover, the literature discloses that, by presenting specific countermeasures in relation to exercise, diet, etc., or presenting them on a weekly basis, the user can more easily manage his health condition.

Referring to FIG. 6 of this literature, which illustrates the configuration of the health management system, first database 110 stores health management feedback information for different types of user's health condition information. The health management feedback information includes user's health conditions based on answers to questions, as well as health management measures for different health conditions.

The health management feedback information contains one or more of diet regimen, exercise regimen and movement regimen for maintaining good health condition. The second database includes user's average physical condition information, which is reference information used to determine whether the user is in normal condition or abnormal condition. The user's average physical condition information is an average of measured values of a body parameter of a user when he/she is healthy, normal condition.

The measuring section measures user's current physical condition. The measuring section measures a variety of parameters, including blood pressure, ECG, pulse rate, respiration rate, and galvanic skin response (GSR), by rapid analysis of biological signals from both hands of the user.

The measuring device uses one sensor for the measurement of user's body fat content and electrocardiogram (ECG). The literature discloses that the measuring device may also measure body weight, blood glucose, body temperature and skin condition. Further, the detection section compares the measured current physical condition with average physical condition information with reference to the second database, to detect any changes in the body parameters.

For example, in the case where blood pressure is measured as current physical condition information, the detection section compares the measured blood pressure level with an average blood pressure level stored in the database. When the measured blood pressure is found to be greater or less than the average value, it is determined that, among many body parameters, blood pressure has changed.

Referring to FIG. 7 which shows a flowchart of the health management method, in step 220, the health management system measures current physical condition of a user, including at last one of blood pressure, blood glucose level, body weight, body temperature, skin condition, and activity level.

In step 240 the health management system references the first database to output lifestyle question information associated with the change thus detected. When the change is detected for blood glucose level, for example, lifestyle question information associated with blood glucose is output. This information may be a question to determine whether or not intake of sugar-containing food can be permitted, a question to determine whether or not administration of a diabetic medication can be permitted, and so forth.

In the case of blood glucose, lifestyle question information is output in association with a changed body parameter, and other types of question information are output over different time spans of medical interview.

Analyzed lifestyle information includes analysis of lifestyle correlated with user's health, such as dietary habit, activity level, and dosage of medication. Health condition information includes warning messages for different risky health conditions, as well as causes of the risky health conditions.

Referring to FIG. 10, when the user is, for example, a diabetic patient, the health management system outputs in step S70 eleventh question information associated with diabetes as additional diabetes question information. Eleventh question information includes, for example, a question that requests the user to confirm whether or not he/she has taken a diabetic medication. The question may read "Have you taken a diabetic medication?"

In response to the eleventh question information, the health management system receives an input from the user as to whether or not he/she has taken a diabetic medication. If the health management system receives an answer to the effect that the user has not yet taken a diabetic medication, the health management system outputs a warning message in step S75.

The warning message is presented to the user as a specific measure to diabetes, which may read as follows: "You are suffering from diabetes, but are receiving no diabetes treatment. Diabetes will develop serious complications such as cancers, kidney diseases or physiological disorders. Immediate blood glucose control and examinations for possible diabetes-associated complications are required. You should consult a diabetes specialist to receive appropriate treatment."

In Patent Literature 59, the following health management for diabetic patients is disclosed by way of example: In step S80, the health management system acquires user's health condition based on the measured physical condition and on the answer input by the user in response to the medical question, and then outputs a daily health report according to the health condition.

The Kim et al. invention is directed to a health management system which basically relies on a manometer and databases coupled thereto. Thus, Kim et al describes in detail blood pressure measurement, but provides little descriptions of other body parameters such as ECG, pulse rate, respiration rate, GSR, body fat, body weight, blood glucose level, body temperature, skin condition, and activity level. In particular, it is totally unclear how activity level or blood glucose level can be measured with the simply named "system."

As to blood glucose measurement, TAIDOC (Taiwan) and GENEXEL-SEIN (Korea) release blood glucose meters in which a manometer and a blood glucose measuring device are combined. These devices employ a biosensor attachable to and detachable from the measuring device.

In the Kim invention, a unspecified "measuring section" measures blood glucose level. It should be noted, however, a technology that enables blood glucose measurement without using any biosensor is a unknown and non-existing technology. Such a unknown technology definitely possesses novelty and inventiveness over any state-of-the-art technology, and therefore, Kim et al should specifically discloses it in the specification or claims of their application for which patent protection is sought.

Suppose a biosensor is integrated with a manometer in the Kim's "measuring section", the biosensor must include a reagent containing enzyme or the like at the measuring part, which reagent needs to be stored in a container until use. For this reason, it is noted that the Kim's system cannot provide a satisfactory measurement result.

It is generally known that in any method, whether invasive or noninvasive, biochemical analysis largely depends on the surrounding temperature (see Non-Patent Literatures 25-28). Particularly in the case of the Kim invention, as the "measuring section" is integrated with the system, the influence of heat transfer from the system cannot be avoided. Therefore, it is noted that the Kim's system cannot provide a satisfactory measurement result also in this aspect.

Patent Literature 22 discloses a health management device for predicting the motion pattern of the user who carries this device using user's physical motion data. The health management device disclosed by Patent Literature 22 includes a motion sensor which detects as physical motion data acceleration (G) and angular speed ($\Omega$) of part of the user's body along at least one of the directions of x, y and z axes; and identifying means for generating step count data by extracting the periodicity of either of both of the acceleration (G) and angular speed ($\Omega$). The health management device further includes mapping data to be compared with the detected physical motion data, the mapping data consisting of [acceleration (G)/angular speed ($\Omega$)] and [step count data] which are previously prepared.

By comparing the measured physical motion data with the mapping data consisting of [acceleration (G)/angular speed ($\Omega$)] and [step count data], the health management device can precisely predict the motion pattern of the user and thus can reduce the frequency and time that physical motion data is measured.

It is disclosed that this also reduces the number of data to be processed and therefore the clock frequency of a control circuit, resulting in reduced power consumption. Regarding the necessity to cut power consumption, the literature discloses that measurement of angular speed ($\Omega$) requires approximately 100 times as large electric power as measurement of acceleration (G).

It is also disclosed that the health management device preferably includes additional sensors for measuring at least one of heart rate, beat-to-beat intervals, blood pressure, blood flow rate, oxygen consumption, blood glucose level and body temperature, for the purpose of supporting health management more efficiently. However, such additional sensors are not illustrated in the drawings.

Referring the description of the drawings, it is disclosed that, although not illustrated, it is preferable to provide additional sensors for measuring at least one of heart rate (pulse rate), beat-to-beat intervals, blood pressure, blood flow rate, oxygen consumption, blood glucose level and body temperature, as a measuring device other than the motion sensor for detecting acceleration (G) and angular speed ($\Omega$) of part of the user's body in at least one of the directions of x, y and Z axes. Namely, it is disclosed that it is possible to more precisely predict the motion pattern as well as to more efficiently support health management, by measuring, with dedicated sensors, physical motion data other than acceleration (G), angular speed ($\Omega$) and step counts.

It is presumed that the health management sensor includes sensors adapted to measure at least one of heart rate (pulse rate), beat-to-beat intervals, blood pressure, blood flow rate, oxygen consumption, blood glucose level and body temperature (see Patent Literature 22).

The Shiratori et al. invention is directed to an exercise meter which relies on acceleration and angular speed. Only passing reference is made in the last claim 14 to the device that includes "sensors which measure at least one of heart rate (pulse rate), beat-to-beat intervals, blood pressure, blood flow rate, oxygen consumption, blood glucose level and body temperature." As with the Kim invention, no description is provided for such sensors. In particular, it is totally unclear how blood glucose level can be measured with the simply named "health management system."

Suppose a biosensor is integrated with the exercise meter in these additional "sensors", the biosensor must include a reagent containing enzyme or the like at the measuring part, which reagent needs to be stored in a container until use. Thus, as with the Kim invention, it is noted that the Shiratori's device cannot provide a satisfactory measurement result.

Moreover, as in the case of the Kim invention, since the "sensors" should be integrated with the device, the influence of heat transfer from the device cannot be avoided. Therefore, it is noted that, as long as a biochemical parameter like blood glucose level is measured, the Shiratori's device cannot provide a satisfactory measurement result.

CITATION LIST

Patent Literature

PTL 1 U.S. Pat. No. 6,258,229
PTL 2 U.S. Pat. No. 6,287,451
PTL 3 U.S. Pat. No. 6,299,757
PTL 4 U.S. Pat. No. 6,309,526
PTL 5 U.S. Pat. No. 6,338,790
PTL 6 U.S. Pat. No. 6,447,657
PTL 7 U.S. Pat. No. 6,461,496
PTL 8 U.S. Pat. No. 6,484,046
PTL 9 U.S. Pat. No. 6,540,890
PTL 10 U.S. Pat. No. 6,576,101
PTL 11 U.S. Pat. No. 6,592,745
PTL 12 U.S. Pat. No. 6,616,819
PTL 13 U.S. Pat. No. 6,618,934
PTL 14 U.S. Pat. No. 6,645,359
PTL 15 U.S. Pat. No. 6,755,949
PTL 16 U.S. Pat. No. 6,767,440
PTL 17 U.S. Pat. No. 6,814,843
PTL 18 U.S. Pat. No. 6,814,844
PTL 19 U.S. Pat. No. 6,866,758
PTL 20 U.S. Pat. No. 6,911,621
PTL 21 U.S. Pat. No. 7,003,340
PTL 22 Japanese Patent (JP-B) No. 3,984,253
PTL 23 U.S. Pat. No. 7,073,246
PTL 24 U.S. Pat. No. 6,004,441
PTL 25 U.S. Pat. No. 6,212,417
PTL 26 WO/95/02357
PTL 27 WO/2005/065538
PTL 28 WO/00/19887
PTL 29 WO/2005/012873
PTL 30 WO/2003/098165
PTL 31 WO/2002/020073
PTL 32 WO/2002/040083
PTL 33 WO/96/08281
PTL 34 WO/96/14096
PTL 35 WO/96/27398
PTL 36 WO/2000/10628
PTL 37 WO/00/19887
PTL 38 Japanese Patent Application Laid-Open (JP-A) No. 2007-216029
PTL 39 WO/00/64940
PTL 40 WO/2005/023348
PTL 41 WO/2001/058511
PTL 42 JP-A No. S59-109987
PTL 43 JP-A No. S59-202016
PTL 44 JP-A No. 2001-133284
PTL 45 JP-A No. H05-332783
PTL 46 JP-A No. H06-300582
PTL 47 JP-A No. H07-080115
PTL 48 JP-A No. H08-117211
PTL 49 JP-A No. S56-07938
PTL 50 JP-A No. H06-24591
PTL 51 JP-A No. H05-25206
PTL 52 JP-A No. H08-298468
PTL 53 JP-A No. 2000-312666
PTL 54 JP-A No. 2000-333918
PTL 55 JP-A No. 2001-029323
PTL 56 JP-A No. 2001-061806
PTL 57 JP-A No. 2007-253482
PTL 58 JP-A No. 2000-148964
PTL 59 Japanese Utility Model Application Laid-Open No. S63-71009
PTL 60 JP-A No. H05-005628
PTL 61 JP-A No. H07-181056
PTL 62 JP-A No. H07-239238
PTL 63 JP-A No. H09-223214
PTL 64 JP-A No. 2000-213954
PTL 65 JP-A No. 2000-283789
PTL 66 JP-A No. 2001-143048
PTL 67 JP-A No. 2001-184477
PTL 68 JP-A No. H11-211502
PTL 69 JP-A No. S58-149730
PTL 70 JP-A No. S58-206723
PTL 71 JP-A No. 2007-236917
PTL 72 JP-A No. 2007-54241
PTL 73 WO/2002/000111
PTL 74 WO/2005/092177
PTL 75 WO/2005/029242
PTL 76 WO/2005/027720
PTL 77 WO/2004/034221
PTL 78 WO/2004/032715
PTL 79 WO/2004/019172
PTL 80 WO/2003/015005
PTL 81 WO/2002/078538
PTL 82 WO/2001/096986
PTL 83 JP-A No. H07-080115
PTL 84 JP-A No. H07-139964
PTL 85 JP-A No. H07-181056
PTL 86 JP-A No. H08-103568
PTL 87 JP-A No. H11-076612
PTL 88 JP-A No. H11-342270
PTL 89 JP-A No. 2000-051528
PTL 90 JP-A No. 2000-067205
PTL 91 JP-A No. 2002-233663
PTL 92 JP-A No. 2001-297155
PTL 93 JP-A No. 2004-24699
PTL 94 JP-A No. 2007-323246
PTL 95 JP-A No. 2007-75586

Non-Patent Literature

[NPL 1] JOSLIN'S DIABETES MELLITUS, 14TH EDITION

[NPL 2] DIABETES TREATMENT GUIDE <2006-2007> (ed. by Japan Diabetes Society)

[NPL 3] THE NEW ENGLAND JOURNAL OF MEDICINE, 329(14), Sep. 30, 1993

[NPL 4] H. YKI-JARVINEN "COMPARISON OF BEDTIME INSULIN REGIMENS IN PATIENTS WITH TYPE 2 DIABETES MELLITUS" ANNALS OF INTERNAL MEDICINE, 1999.

[NPL 5] HENRY R R. "INTENSIVE CONVENTIONAL INSULIN THERAPY FOR TYPE II DIABETES: METABOLIC EFFECTS DURING A 6-MO OUTPATIENT TRIAL" DIABETES CARE 1993; 16(1):21-31.

[NPL 6] TURNER R C. "RISK FACTORS FOR CORONARY ARTERY DISEASE IN NON-INSULIN DEPENDENT DIABETES MELLITUS: UNITED KINGDOM PROSPECTIVE DIABETES STUDY (UKPDS: 23)" BMJ. 1998 Mar. 14; 316(7134):823-8.

[NPL 7] J. L. JOHNSON "EXERCISE TRAINING AMOUNT AND INTENSITY EFFECTS ON METABOLIC SYNDROME (FROM STUDIES OF A TARGETED RISK REDUCTION INTERVENTION THROUGH DEFINED EXERCISE)" AMERICAN JOURNAL OF CARDIOLOGY, VOL. 100(12), 2007, 1759-1766.

[NPL 8] AINSWORTH, B. E. "COMPENDIUM OF PHYSICAL ACTIVITIES: CLASSIFICATION OF ENERGY COSTS OF HUMAN PHYSICAL ACTIVITIES" MEDICINE & SCIENCE IN SPORTS & EXERCISE. 25(1):71-80, January 1993.

[NPL 9] NELSON M E. "PHYSICAL ACTIVITY AND PUBLIC HEALTH IN OLDER ADULTS: RECOMMENDATION FROM THE AMERICAN COLLEGE OF SPORTS MEDICINE AND THE AMERICAN HEART ASSOCIATION" MED SCI SPORTS EXERC. 2007 August; 39(8):1435-45.

[NPL 10] W. H. M. SARIS "HOW MUCH PHYSICAL ACTIVITY IS ENOUGH TO PREVENT UNHEALTHY WEIGHT GAIN? OUTCOME OF THE IASO 1ST STOCK CONFERENCE AND CONSENSUS STATEMENT" OBESITY REVIEWS VOLUME 4 ISSUE 2: 101-114, May 2003.

[NPL 11] J. SALLIS "ENVIRONMENTAL INTERVENTIONS FOR EATING AND PHYSICAL ACTIVITY A RANDOMIZED CONTROLLED TRIAL IN MIDDLE SCHOOLS" AMERICAN JOURNAL OF PREVENTIVE MEDICINE, VOLUME 24, ISSUE 3: 209-217.

[NPL 12] I-MIN LEE. "RELATIVE INTENSITY OF PHYSICAL ACTIVITY AND RISK OF CORONARY HEART DISEASE" CIRCULATION. 2003; 107:1110-1116.

[NPL 13] LEVINE J A. "NONEXERCISE ACTIVITY THERMOGENESIS (NEAT): ENVIRONMENT AND BIOLOGY" AM. J. PHYSIOL. 286:E675-E685, 2004.

[NPL 14] DEXCOM "SEVEN CONTINUOUS GLUCOSE MONITORING SYSTEM USER'S GUIDE" 2007 (Reference URLs: Http://www.dexcom.com/; Http://www.dexcom.com/html/dexcom_products_user_manuals.html)

[NPL 15] RIERS TO IMPROVED DIABETES MANAGEMENT: RESULTS OF THE CROSS-NATIONAL DIABETES ATTITUDES, WISHES AND NEEDS (DAWN) STUDY" DIABETIC MEDICINE. VOLUME 22, NUMBER 10, October 2005:1379-1385(7)

[NPL 16] "Diabetes mellitus Field Study" Ministry of Health, Labor and Welfare, Health Service Bureau S (2004) Reference URL: Http://www.mhlw.go.jp.shingi/2004/03/s0318-15.html

[NPL 17] BASSETT DR. "VALIDITY AND RELIABILITY ISSUES IN OBJECTIVE MONITORING OF PHYSICAL ACTIVITY" RES Q EXERC SPORT. 2000 June; 71(2 SUPPL):S30-6.

[NPL 18] BEIGHLE A. "PEDOMETERS, PHYSICAL ACTIVITY, AND ACCOUNTABILITY" JOPERD 2001; 72(9):16-9.

[NPL 19] CROUTER S E. "VALIDITY OF 10 ELECTRONIC PEDOMETERS FOR MEASURING STEPS, DISTANCE, AND ENERGY COST" MED SCI SPORTS EXERC. 2003; 35 (8):1455-60.

[NPL 20] WELK G L, EDITOR. "PHYSICAL ACTIVITY ASSESSMENTS FOR HEALTH-RESEARCH" CHAMPAIGN (IL): HUMAN KINETICS; 2002.

[NPL 21] MATTHEWS C E. "DEVELOPMENT AND TESTING OF A SHORT PHYSICAL ACTIVITY RECALL QUESTIONNAIRE" MED SCI SPORTS EXERC. 2005 June; 37(6):986-94.

[NPL 22] MONTOYE H. "MEASURING PHYSICAL ACTIVITY AND ENERGY EXPENDITURE" CHAMPAIGN (IL): HUMAN KINETICS; 1996.

[NPL 23] CROUTER SE. "ACCURACY OF POLAR S410 HEART RATE MONITOR TO ESTIMATE ENERGY COST OF EXERCISE" MED SCI SPORTS EXERC. 2004; 36(8):1433-9.

[NPL 24] FREEDSON P S. "OBJECTIVE MONITORING OF PHYSICAL ACTIVITY USING MOTION SENSORS AND HEART RATE" RES Q EXERC SPORT. 2000 June; 71(2 SUPPL):S21-9.

[NPL 25] MICHAEL J. HALLER "ADVERSE IMPACT OF TEMPERATURE AND HUMIDITY ON BLOOD GLUCOSE MONITORING RELIABILITY: A PILOT STUDY" DIABETES TECHNOLOGY & THERAPEUTICS. Feb. 1, 2007: 1-9.

[NPL 26] A. HAUPT. "THE EFFECTS OF SKIN TEMPERATURE AND TESTING SITE ON BLOOD GLUCOSE MEASUREMENTS TAKEN BY A MODERN BLOOD GLUCOSE MONITORING DEVICE" DIABETES TECHNOLOGY & THERAPEUTICS. Aug. 1, 2005: 597-601.

[NPL 27] ANDREAS PFUTZNER. "IMPACT OF POSTURE AND FIXATION TECHNIQUE ON IMPEDANCE SPECTROSCOPY USED FOR CONTINUOUS AND NONINVASIVE GLUCOSE MONITORING" DIABETES TECHNOLOGY & THERAPEUTICS. Aug. 1, 2004:435-441.

[NPL 28] OMAR S. KHALIL "NON-INVASIVE GLUCOSE MEASUREMENT TECHNOLOGIES: AN UPDATE FROM 1999 TO THE DAWN OF THE NEW MILLENNIUM" DIABETES TECHNOLOGY & THERAPEUTICS. Oct. 1, 2004: 660-697.

SUMMARY OF INVENTION

Technical Problem

However, until now there is no invention directed to a blood glucose meter in which measurement of blood glucose level and measurement living activity are combined. For example, pedometers measure only step counts for the amount of exercise, and blood glucose meters measure only blood glucose level.

Exercise monitoring devices are mainly used by healthy people to measure the energy consumption during exercise and are specialized in the measurement of physical activity, oxygen consumption, etc, during specific exercise. Thus, medical practitioners generally cannot have easy access to the history of living activity from diabetic patients. History of living activity can be used in diagnosis or treatment to help reduce the HBA1c level or prevent the progression of kidney disease.

The present invention has been accomplished in order to solve the foregoing problems pertinent in the art. An object of the present invention is to provide measurement devices by which the blood glucose level or other parameter of a diabetic patient can be measured easily and precisely, wherein the measured value can be clinically applied easily; insulin infusion devices; measurement methods; methods of controlling insulin infusion devices; and programs.

Solution to Problem

An embodiment of the measurement device of the present invention includes:

a biosensor which includes a reagent surface on which a reagent is placed, the reagent selectively responding to a specific analyte in a biological fluid to detect the presence or concentration of the analyte in the biological fluid;

an analyte measurement section that measures a characteristic amount of the analyte with a biosensor;

a motion measurement section that measures the tilt angle or rotation angle of the reagent surface from a neutral position thereof, or vibration applied to the reagent surface, to output a measured value as motion information of living activity;

a recording section that records therein the characteristic amount of the analyte and the motion information; and a controlling section that controls the analyte measurement section and the recording section based on the motion information.

An embodiment of the measurement device of the present invention includes:

a biosensor which selectively responds to a specific analyte in a biological fluid for detecting the presence or concentration of the analyte in the biological fluid; and a housing to be attached to a living body, wherein the housing includes: an analyte measurement section that measures a characteristic amount of the analyte with the biosensor; a motion measurement section that measures motion information of living activity of the living body; and a recording section that records therein the motion information and the characteristic amount with the motion information and the characteristic amount associated with each other.

An embodiment of the insulin infusion device of the present invention includes:

a cannula for infusing insulin under the skin;

an insulin infusion section for storing therein insulin to be delivered to the cannula;

a motion measurement section that measures the tilt angle or rotation angle of a center axis of the insulin infusion section from a neutral position thereof, or vibration applied to the insulin infusion section, to output a measured value as motion information of living activity; and a controlling section that controls, based on the motion information, a process of notifying a user of the timing or recommended direction of priming of the insulin infusion section.

An embodiment of the measurement method of the present invention includes:

a first measurement step of measuring a characteristic amount of a specific analyte in a biological fluid with a biosensor having a reagent surface;

a second measurement step of measuring the tilt angle or rotation angle of the reagent surface from a neutral position thereof, or vibration applied to the reagent surface, as motion information of living activity;

a recording step of recording the motion information; and a controlling step of controlling, based on the motion information, a measurement operation of the first measurement step and a recording operation of the recording step.

An embodiment of the measurement method of the present invention includes:

a first measurement step of measuring a characteristic amount of a specific analyte in a biological fluid with a biosensor;

a second measurement step of measuring motion information of living activity; and recording the motion information and the characteristic amount measured in the first measurement step with the motion information and characteristic amount associated with each other.

An embodiment of the method of the present invention for controlling an insulin infusion device is a method for controlling an insulin infusion device which includes a cannula for infusing insulin under the skin, and an insulin infusion section for storing therein insulin to be delivered to the cannula, the method including:

measuring the tilt angle or rotation angle of a center axis of the insulin infusion section from a neutral position thereof, or vibration applied to the insulin infusion section, as motion information of living activity; and notifying, based on the motion information measured, a user of the timing or recommended direction of priming of the insulin infusion section.

Another aspect of the present invention is programs for causing a computer to execute the above steps.

Advantageous Effects of Invention

According to the present invention, it is possible to easily and precisely measure diabetic patient's blood glucose levels and the like associated with daily living activities, as well as to clinically apply the measured values easily.

For example, by measuring blood glucose level or the like in association with living activity, it is possible to improve measurement accuracy. When appropriate measurement is not possible, it is possible to notify the user to that effect.

It is also possible to provide novel information by recording and displaying measured blood glucose levels and living activity levels, with living activity level and the blood glucose level associated with each other.

BRIEF DESCRIPTION OF DRAWINGS

FIG. 18 shows a list of preprandial and postprandial blood glucose levels as measured with a blood glucose measuring device according to Embodiment 2;

FIG. 19 shows a list of preprandial and postprandial blood glucose levels as measured with a blood glucose measuring device according to Embodiment 2;

DESCRIPTION OF EMBODIMENTS

Figure 1:
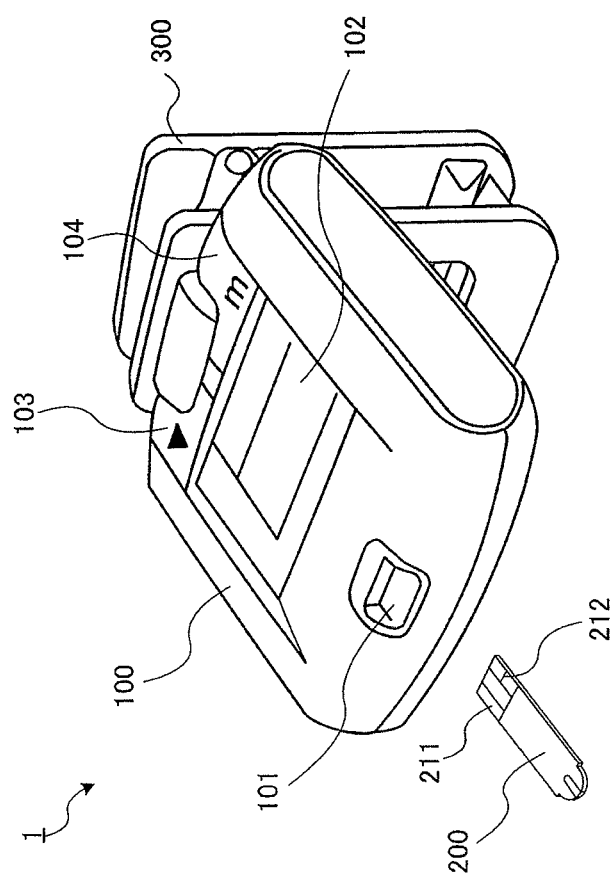
FIG. 1 is an overview illustration of a blood glucose measuring system according to Embodiment 1.

Now, embodiments of the present invention will be described in detail with reference to the accompanying drawings. In the description of the present invention, human body is exemplified as a living body; living activity as used herein thus means living activity of human body. It should be noted, however, that the present invention should not be construed as being limited to human. Indeed, the present invention can be applied to animals other than human. As used herein, "characteristic amount of a specific analyte in a biological fluid" means, but not limited to, blood glucose level or glucose level in the subcutaneous interstitial fluid; it may also mean lactic acid level or cholesterol level.

(Principles)

As described above, the measured blood glucose levels and daily living activities are not combined in the conventional blood glucose meters.

Thus, with the conventional blood glucose meters, diabetic patients cannot monitor their blood glucose level or other parameter in real time. Moreover, the conventional glucose meters may suffer from the drawback of reduced measurement accuracy due to changes in the measurement environment during daily activities. Further, medical practitioners including doctors cannot clinically apply the records of patient's daily living activities and blood glucose levels easily.

The inventors established that novel information can be obtained if a subject carries a blood glucose meter capable of detection of motions of daily living activities at appropriate times. Namely, measurement data of blood glucose level associated with motion information of daily living activities substantially differs from simple blood glucose data in that the former is a measured value with motion information—real-time living activity level. This also applies to CGM systems and insulin pumps. If conventional blood glucose readings are deemed as scalar quantities, measurement data associated with motion information according to the present invention can be deemed as vector quantities correspondingly.

In the present invention measurement data having motion information or real-time activity level is recorded together with time information, providing novel information on the display using the measurement data having real-time activity level and time information. This allows subjects, including diabetic patients, to take proper actions in real time, as well as allows medical practitioners to have easy access to the records of patient's daily living activities for diagnosis or treatment.

A method and system according to the present invention roughly consists of real-time acquisition of measurement data, and reference of past measurement data.

Real-time acquisition of measurement data realizes: [A. high-precision measurement control] and [B. living activity measurement control], and reference of past measurement data realizes [C. detailed analysis control].

[A. High-precision measurement control] employs body motions of human activities as a condition to trigger sensor detection. Since the biosensor uses blood as a liquid sample, measurement accuracy is affected when the device is attached to the system of the present invention, which is carried by a user and thus subject to tilting due to body motion. Thus, [A. high-precision measurement control] is indispensable in improving the measurement accuracy of the system of the present invention which is carried during use.

[B. Living activity measurement control] correlates activities such as eating meals or sleeping with measurement data such as blood glucose level in real time, and thereby displays or records novel information.

[C. Detailed analysis control] analyzes in detail the measurement data of living activity and blood glucose level or other body parameter, with reference to the past information stored in the system. More specifically, the system is changed from [B. living activity measurement control] mode to [C. Detailed analysis control] mode, and executes [C. Detailed analysis control]. It is preferable that analysis is done from the viewpoint of experts, e.g., by medical practitioners such as doctors. The system may be wired or wirelessly connected to a terminal device for detailed analysis by use of the history information stored in the system.

Regarding Embodiments 1 to 13 below, Embodiment 1 describes [A. high-precision measurement control] and [B. living activity measurement control]; Embodiments 2 to 10 mainly describe [B. living activity measurement control]; Embodiment 11 describes [B. living activity measurement control]; Embodiment 12 describes [C. detailed analysis control]; and Embodiment 13 describes impact detection that ensures reliability of [A. high-precision measurement control], [B. living activity measurement control], and [C. detailed analysis control].

Embodiment 1

FIG. 1 is an overview illustration of a blood glucose measuring system according to Embodiment 1 based on the above fundamental concept. This embodiment is an example in which a blood glucose measuring system of the present invention is applied to a self-monitoring system for diabetic patients.

As illustrated in FIG. 1, blood glucose measuring system 1 includes blood glucose measuring device 100, blood glucose sensor 200, and attachment unit 300.

Blood glucose measuring device 100 (housing) includes sensor attachment section 101, display section 102 (one example of display means or notifying means), operation key 103, and memory & decision key 104.

To sensor attachment section 101 is attached blood glucose sensor 200, an attachable/detachable biosensor.

Figure 2:
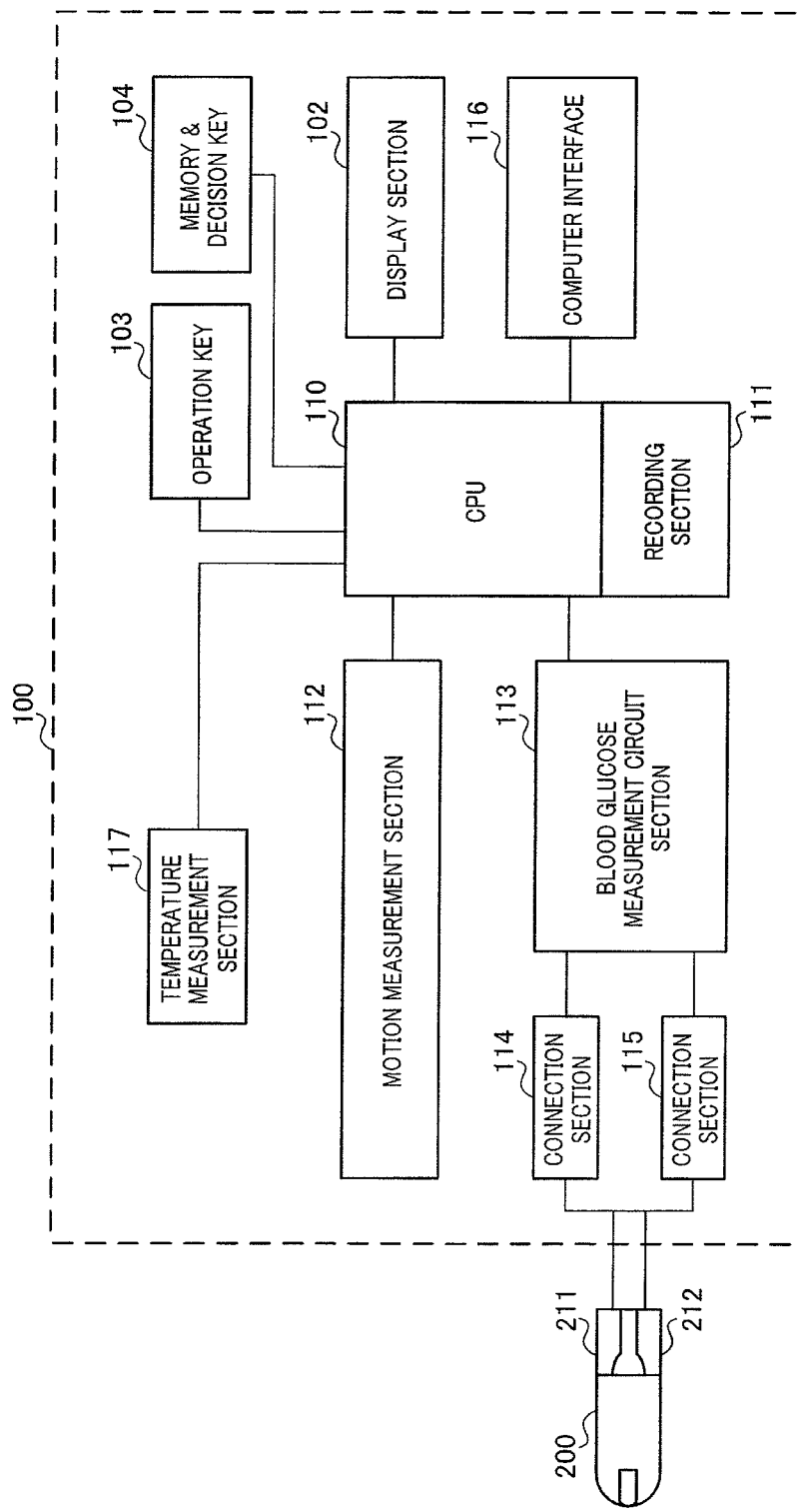
FIG. 2 is a block diagram of the configuration of a blood glucose measuring device according to Embodiment 1.

Display section 102 is composed of a liquid crystal display (LCD) capable of dot-matrix color display, electroluminescence (EL), white LED backlight, and various drivers, and display thereon information in response to instruction signals from CPU 110 (FIG. 2). Display section 102 displays, for example, blood glucose level and/or measurement history.

Operation key 103 is a push bottom provided on the housing of blood glucose measuring device 100, and when pushed by a user it generates an operation signal indicating to that effect and outputs the signal to CPU 110 (FIG. 2).

Memory & decision key 104 causes display section 102 to display history of various measurements, and a user inputs a command of display for confirmation. With memory & decision key 104 and operation key 13, a user inputs a command to a software program.

Blood glucose sensor 200 is a biosensor, especially a biosensor which specifically measures blood glucose level. A biosensor means an analytical element, device or instrument that specifically responds to a specific analyte in a liquid sample and measures the concentration or presence of the analyte by measuring the electrical, optical or other signal produced. It is essential that a biosensor have an enzyme-containing reagent in the measurement part, that the reagent be stored until use, and that the biosensor be attachable to or detachable from the measuring device.

The biosensor is not limited to a blood glucose biosensor and may be an electrochemical biosensor having electrodes. Examples include lactic acid sensors for measuring lactic acid levels and cholesterol sensors for measuring cholesterol levels, in addition to blood glucose sensors.

Blood glucose sensor 200 have electrodes formed on an insulating base plate made of polyethylene terephthalate or the like, wherein a sample supply channel is formed at the edge, and a reagent layer containing enzyme or mediator is formed in the sample flow channel.

Blood glucose sensor 200 includes lead electrodes 211 and 212, and is attachable to and detachable from sensor attachment section 101 of blood glucose measuring device 100. The detail structure of blood glucose sensor 200 will be described later with reference to FIG. 3.

Attachment unit 300 is a hook member used to attach blood glucose measuring device 100 to a clothes or the like. Attachment unit 300 is a clip in FIG. 1.

Preferably, since the living activity meter is carried by a user for a long period of time, blood glucose measuring device 100 is so designed as to be attachable to or detachable from attachment unit 300. For example, upon blood glucose measurement, blood glucose measuring device 100 is detached, with attachment unit 300 remaining attached to the clothes.

Although blood glucose measuring device 100 and attachment unit 300 are shown as being attachable to and detachable from each other, they may be combined in one unit, i.e., the blood glucose measuring device itself may have attachment unit structure.

[Blood Glucose Measuring Device 100]

FIG. 2 is a block diagram of the configuration of blood glucose measuring device 100.

As illustrated in FIG. 2, blood glucose measuring device 100 includes CPU 110 (controlling means), recording section 111, motion measurement section 112 (motion measurement means), blood glucose measurement circuit section 113 (analyte measurement means), connection sections 114 and 115, computer interface 116, temperature measurement section 117 (temperature measurement means), display section 102, operation key 103, and memory & decision key 104.

CPU 110 controls the overall operation of blood glucose measuring device 100, as well as the process of correlating blood glucose levels measured in "living activity measurement mode", "blood glucose measurement mode" and "sensor insertion mode" with the motion information measured by the motion measurement section. CPU 110 also has a time counting function like a timer.

Recording section 111 is composed of semiconductor memories and the like such as ROM, RAM and electrically erasable and programmable read only memory (EEPROM), records measurement data such as blood glucose levels. ROM stores software programs to be executed by CPU 110 as well as fixed data. RAM is used as a so-called working memory that temporally stores blood glucose measurement data, data for calculation, and calculation results. Some data in the RAM are duplicated in the backup or the RAM is composed of EEPROM, whereby blood glucose measurement data can be stored even after the power switch (not shown) is turned off.

Motion measurement section 112 is a sensor for measuring motion information described above, particularly detects motions of blood glucose measuring device 100 caused by human activities (second measurement step). In this embodiment, motion measurement section 112 is composed of an acceleration sensor (hereinafter motion measurement section 112 will also be referred to as "acceleration sensor 112").

"Living activity" means an activity like sleeping or eating a meal, which cannot be designated as exercise (sports). Energy expended during such a living activity is called non-exercise activity thermogenesis (NEAT). Daily living activities also include other types of physical activities other than exercise (body energy metabolism) which have been identified by the research of NEAT. Living activity level is measured in terms of intensity of motion. The measurement result of living activity, or living activity level, is recorded in recording section 111.

Acceleration sensor 112 is a 3-axis acceleration sensor for detecting accelerations in the directions of x, y and z axes, i.e., vertically, horizontally and back and forth. Acceleration sensor 112 detects motion of living activity of a diabetic patient equipped with the device, and outputs the measurement result to CPU 110.

Specifically, acceleration sensor 112 measures, as motions of physical activity, any of the tilting of the plate-shaped base of blood glucose sensor (biosensor) 200 relative to the horizontal; the rotation of the base; and the vibration applied to the base. In this embodiment, while acceleration sensor 112 measures motions of the base, the motion information of 112 the base measures motions of daily living activities of a diabetic patient, which are detected via motions of the housing.

Namely, acceleration sensor 112 measures motions of two different targets: motions of the base of blood glucose sensor (biosensor) 200 attached to the blood glucose measuring device 100 (housing); and motions of living activity of a diabetic patient who carries blood glucose measuring device 100. Information of motions of blood glucose sensor 200 and information of motions of blood glucose measuring device 100 can both be referred to as motion information based on living activity, because their motions are derived from the motions of living activity of the diabetic patient which act on blood glucose measuring device 100.

Acceleration sensor 112 has been described by way of example, but any sensor can be employed as long as living activity can be detected; for example, a vibration sensor or other sensor may be employed. It should be noted, however, that by using acceleration sensor 112 it is possible to provide a novel function of correlating measured blood glucose level (described later) with motion information. Blood glucose measuring device 100 may include an angular speed sensor for detecting rotational motions, in addition to or in place of acceleration sensor 112. With this configuration, it is possible to measure living activity more precisely.

CPU 110 performs filtering process to remove frequency components greater than the maximum frequency of human action, from the motion information. Acceleration sensor 112 and CPU 110 constitute measurement means of blood glucose level or the like.

CPU 110 controls a step of recording in recording section 111 the measured motion information and blood glucose level measured by blood glucose sensor 200 while associating them with each other. CPU 110 also controls a step of displaying on display section 102 the measured motion information and blood glucose level which have been associated with each other.

CPU 110 also functions as means of calculating living activity levels based on the motion information. Living activity level will be described in detail later. Motion information is associated with blood glucose level in this embodiment. The motion information should be broadly interpreted encompassing living activity level. Namely, CPU 110 records and displays measured living activity levels and blood glucose levels while associating them with each other.

CPU 110 preferably displays on display section 102 the calculated living activity level as an average value measured during a predetermined period. For example, CPU 110 is caused to reset data every midnight at 0:00 am, so that all data is stored on a day-to-day basis. It is preferable to store data in units of 24 hours with a timer incorporated in CPU 110. The timer is reset every 24 hours and displayed on display section 102.

However, since blood glucose level may be measured at different time points (e.g., before meal, after meal), it is preferable not to employ an averaged value for blood glucose level when displaying it on a day-to-day basis.

Blood glucose measurement circuit section 113 is an electric circuit which measures blood glucose level (first measurement step) using blood glucose sensor 200 attached to connection sections 114 and 115.

Blood glucose measurement circuit section 113 detects the introduction of sample solution into blood glucose sensor 200 as well as controls the measurement result display process in accordance with measurement algorithm, to measure blood glucose level.

Connection sections 114 and 115 are incorporated into sensor attachment section 101 (FIG. 1) and connect blood glucose sensor 200 to blood glucose measuring device 100. When blood glucose sensor 200 is attached to sensor attachment section 101 of blood glucose measuring device 100, lead electrodes 211 and 212 of blood glucose sensor 200 are electrically connected to connection sections 114 and 115 respectively of blood glucose measuring device 100.

Computer interface 116 is an interface that can be wired or wirelessly connected to a computer. Examples include universal serial bus (USB), Bluetooth®, wired or wireless LAN, and radio frequency (RF) communication.

Temperature measurement section 117 measures and outputs body temperature. CPU 110 associates the body temperature measured by temperature measurement section 117 with blood glucose level and living activity level, and displays and records them on display section 102 and in recording section 111, respectively.

[Blood Glucose Sensor 200]

The following describes the definitions of the terms used in the specification.

As used herein, "base" means an element which is made of insulating material and provides a liquid sample chamber, electrodes and other structural components of a biosensor.

As used herein, "electrode" means an element which is prepared on an electrochemical biosensor, for creating an electric field in the reaction system to detect reactions occurred therein as electrochemical signals and for receiving the electrochemical signals.

As used herein, "reaction reagent" means a group of substances that chemically reacts with the target substance in a liquid sample. The group of substances consists of one or more enzymes, one or more electron transport substances, and one or more buffers, for example.

As used herein, "spacer" means an element placed on the base to provide walls of a capillary, defining the length (along sample intake direction), width and height of the capillary.

As used herein, "upper cover" means an element placed on the spacer to provide the ceiling of the liquid sample chamber.

As used herein, "inlet" means a gap through which a liquid sample is introduced into the liquid sample chamber.

As used herein, "air vent" means an exhaustion hole from which a gas in the liquid sample chamber is discharged to the outside upon intake of a liquid sample into the liquid sample chamber.

As used herein, "enzyme" means a biological substance that catalyzes chemical reactions occurring in living organism.

As used herein, "electron transport substance", also referred to as "mediator", means a substance that mediates transport of electrons of a reduced form of a certain chemical species to an oxidized form of another chemical species or transport of free electrons of a metal to another metal, either alone or in cooperation with another electron transport substance.

As used herein, "substrate" means a substance targeted by enzyme for reaction.

As used herein, "product" means a substrate-derived substance that yields as a result of enzyme-substrate chemical reaction.

As used herein, "drift" means discontinuity in a continuous plot of measured values in CGMS, e.g., a portion where a measured value decreases by 10% or more compared to the immediately preceding measured value and the next measured value changes by 10% or less.

Figure 3:
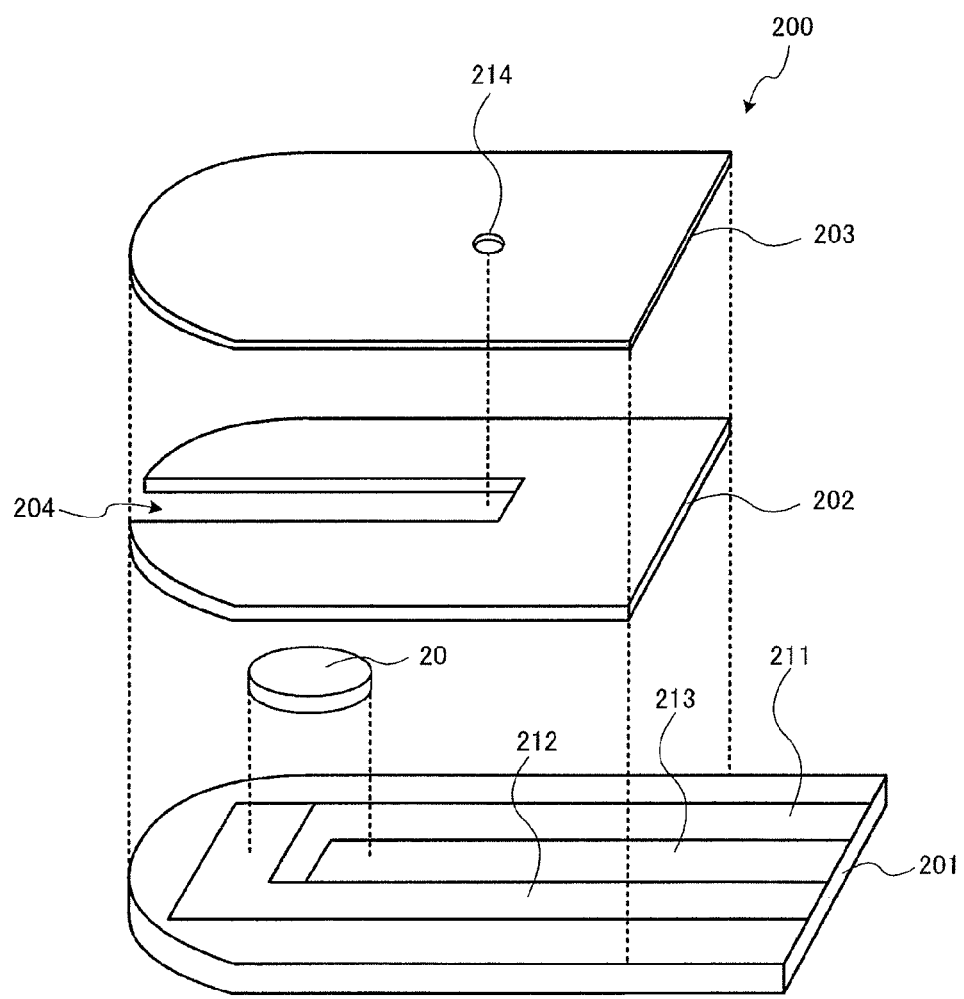
FIG. 3 is an exploded perspective view of a blood glucose sensor of a blood glucose measuring device according to Embodiment 1.

FIG. 3 is an exploded perspective view of blood glucose sensor 200. FIGS. 3 to 7 correspond to the description for performing [A. high-precision measurement control] described above.

As illustrated in FIG. 3, in blood glucose sensor 200, upper cover 203 is placed over base 201, with spacer 202 having a rectangular notch interposed between therebetween and leaving one end of base 201 (right side end in FIG. 2) uncovered.

Upper cover 203 is placed over spacer 202 so that reaction reagent 20 placed in such a way as to partially cover lead electrodes 211 and 212 and electrode 213 is exposed. Base 201 and spacer 202 are preferably bonded together. Also, spacer 202 and upper cover 203 are preferably bonded together. Bonding methods include, but not limited to, the use of a commercially available adhesive, ultrasonic bonding, and heat bonding.

When these components are assembled, the notch of spacer 202 serves as a capillary that holds a blood sample. The capillary extends along the length of blood glucose sensor 200 and communicates with the outside at one end of spacer 202 (left side end in FIG. 2).

In other words, the capillary communicates with the opening of notch 204, which is the inlet from which a blood sample is introduced from the outside of blood glucose sensor 200. Upper cover 203 includes air vent 214 at one end of the capillary opposite to the other communicating with the outside. This configuration causes a capillary action that allows a blood sample to be easily introduced into the capillary through the opening of notch 204, a blood sample inlet.

Lead electrodes 211 and 211 and electrode 213 are disclosed on base 201 so as to be partially exposed to the capillary. Reaction reagent 200 is formed on base 201 so as to partially cover lead electrodes 211 and 212 and electrode 213. Reaction reagent 20 contains a redox enzyme that recognize a blood sample's analyte as a substrate, and an electron mediator.

Lead electrodes 211 and 211, electrode 213 and reaction reagent 20 acquire data concerning the concentration of a blood sample's analyte based on the amount of current flowing between the electrodes. Mainly, the substance that undergoes electrochemical reactions on the electrodes is an electron mediator which receives and transports electrodes from and to the redox enzyme.

One end of each electrode is exposed at one end of base 201 not covered with spacer 202 and upper cover 203, so that voltage can be applied between the electrodes.

Examples of analytes in a blood sample include substances except for hemocyte, such as glucose, albumin, lactic acid, bilirubin, and cholesterol. For the redox enzyme, an enzyme that recognizes the target analyte as a substrate is employed. Examples thereof include glucose oxidase, glucose dehydrogenase, lactate oxidase, lactate dehydrogenase, bilirubin oxidase, and cholesterol oxidase.

The amount of a redox enzyme in the reaction reagent layer is 0.01 to 100 units (U), preferably 0.05 to 10 U, more preferably 0.1 to 5 U.

Reaction reagent 20 preferably contains an electron mediator that has a function of transporting electrons generated in enzymatic reactions to the electrodes; examples include potassium ferricyanide, p-benzoquinone, p-benzoquinone derivatives, oxidized phenazine methosulfate, methylene blue, ferricinium, and ferricinium derivatives.

The electron mediator is required to be capable of smooth electron transport between the enzyme and electrode, can exist as an oxidized form in the reaction reagent for a long time, have high solubility, and is inexpensive, for example. Reaction reagent 20 may contain a water-soluble polymer compound for the purpose of increasing the formability of the reaction reagent layer.

The water-soluble polymer compound is at least one compound selected from the group consisting of carboxymethyl cellulose and salts thereof, hydroxyethyl cellulose, hydroxypropyl cellulose, methyl cellulose, ethyl cellulose, ethyl hydroxyethyl cellulose, carboxyethyl cellulose and salts thereof, polyvinyl alcohol, polyvinylpyrrolidone, polyamino acids such as polylysine, polystyrene sulfonate and salts thereof, gelatin and derivatives thereof, polyacrylic acid and salts thereof, polymethacrylic acid and salts thereof, starch and derivatives thereof, maleic anhydride polymer and salts thereof, and agarose gel and derivatives thereof.

In this embodiment, reaction reagent 20 is provided by applying a liquid reaction reagent over base 201 in such a way as to cover at least a portion of the bottom of lead electrodes 211 and 212 and electrode 213, followed by drying. Preferable methods of providing a reaction reagent other than coating include printing and dipping.

Materials of insulating base 201, spacer 202 and upper cover 203 include polyethylene terephthalate, polycarbonate, polyimides, polyethylene, polypropylene, polystyrene, polyvinyl chloride, polyoxymethylene, monomer cast nylon, polybutylene terephthalate, methacrylate resin, ABS resin, and glass.

Lead electrodes 211 and 212 and electrode 213 may be made of any known conductive material, such as palladium, platinum, gold, silver, titanium, copper, nickel, and carbon. Non-limiting examples of methods of providing conductive materials on the base include sputtering, printing, and dipping. Lead electrodes 211 and 212 and electrode 213 are then formed by forming non-conductive tracks on the conductive layer with a laser irradiation device, which conductive layer formed on base 201 by vapor deposition of palladium.

Next, the mechanism by which the re-dissolved reagent and device tilting reduces measurement accuracy will be described In the case of a biosensor, such as one used as blood glucose sensor 200, the user pierces the skin (e.g., on the finger, palm or arm) and squeezes a drop of blood, allowing the liquid blood sample to be introduced into the capillary of the device for measurement.

In particular, where the squeezed blood sample is liquid, blood viscosity varies from one individual to another depending on the hematocrit level, total cholesterol level, total protein level, and so forth. The blood viscosity difference leads to poor measurement accuracy due to different dissolution rates of reagent among different individuals.

Recently, biosensors, particularly those employed as blood glucose sensor 200, are increasingly becoming smaller in size with shorter measurement time. To achieve rapid measurement, reaction reagents with high re-solubility have become used in biosensors so that the reaction reagent can be dissolved in the liquid sample as soon as it contacts the liquid sample. This, however, triggers a phenomenon in which the reaction reagent dissolved in the liquid sample flows towards the direction in which device is tilted.

Specifically, when the flow direction of a highly fluid reaction reagent becomes non-uniform, it results in a large non-uniformity in the concentration of the reagent across the reaction region, leading to poor measurement accuracy as well as poor system reliability.

In order to improve measurement accuracy for high system reliability, the blood glucose measuring system according to this embodiment employs the following measuring method in the biosensor.

When employing the dual electrode amperometry, the voltage applied between the electrodes during measurement may be constant or changed stepwise, or may be swept or applied intermittently. A voltage that is high enough to cause electrochemical reactions of interest should be applied between the electrodes, which is determined according to the nature of the chemical species and electrodes employed.

In general, a voltage is applied that is high enough to make the electrochemical reaction rates in the system become diffusion rate controlled, rather than voltage controlled. However, it is often the case that various interfering substances are present in the analyte solution. In this case, when the electrode potential is excessively increased by application of high voltage between the electrodes, unwanted reactions of such interfering substances also take place. For this reason, the level of voltage to be applied between the electrodes should be determined carefully.

In this embodiment, the concentration of glucose in a liquid sample was quantified by measuring the current value obtained by applying a potential difference of 250 mV voltage between the electrodes.

Figure 4:
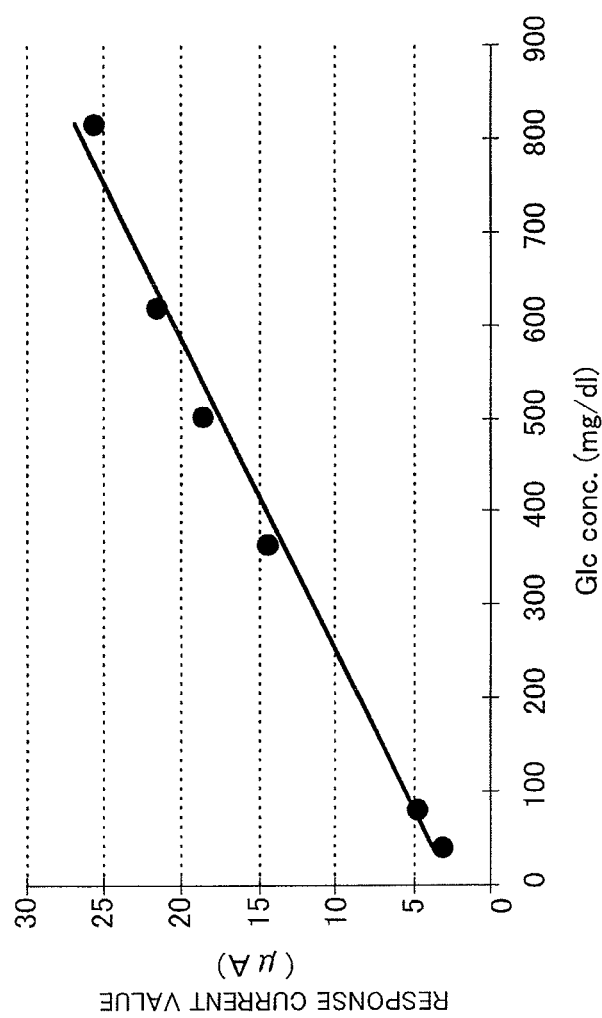
FIG. 4 is a plot of response current vs. blood glucose level as measured with a blood glucose sensor of a blood glucose measuring device according to Embodiment 1.

FIG. 4 is a plot of response current vs. blood glucose level as measured with blood glucose sensor 200.

As shown in FIG. 4, blood glucose sensor 200 according to this embodiment offers a good linear relationship between response current and blood glucose level over a measured concentration range. Thus, it can be judged that blood glucose sensor 200 can satisfactorily function as a blood glucose biosensor.

As described above, excellent measurements can be made where the blood glucose measuring system is held horizontally (neutral position). When using such a blood glucose measuring system, however, it is typical that the user holds the biosensor-equipped measuring device with one hand, and holds a lancet with the other hand to puncture the skin and squeezes out a drop of blood, which is introduced into the biosensor for measurement. In such a situation, measurements are not necessarily made in a state where the sensor is held horizontally. Rather, measurements are often made with the device held at angles to the horizontal. The following describes how measurement angle influences sensor performance.

While the neutral position of the biosensor illustrated in FIG. 3 (blood glucose sensor 200) is such that the device is held horizontally, some biosensors have a vertically oriented reagent surface, that is, the neutral position is vertical. Motion measurement section 112 measures, among various motions parameters, tilt angle or rotation angle of the device from the neutral position.

Figure 5:
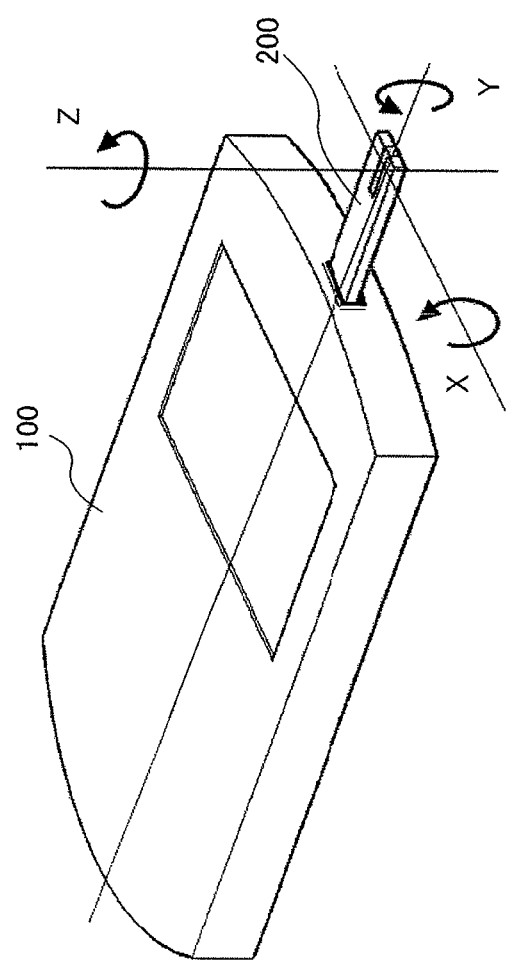
FIG. 5 explains that the blood glucose measuring device according to Embodiment 1 is rotated about the biosensor's reaction site around X, Y and Z axes.

FIG. 5 explains how the biosensor's reaction site of the blood glucose measuring device according to Embodiment 1 is rotated about the X, Y and Z axes. For the convenience of explanation, blood glucose measuring device 100 and blood glucose sensor 200 are schematically drawn in FIG. 5 and therefore are not identical in shape to their counterparts in FIG. 1.

In the following description, rotation about x axis, rotation about y axis, and rotation about z axis are referred to as x axis rotation, y axis rotation, and z axis rotation, respectively.

Figure 6:
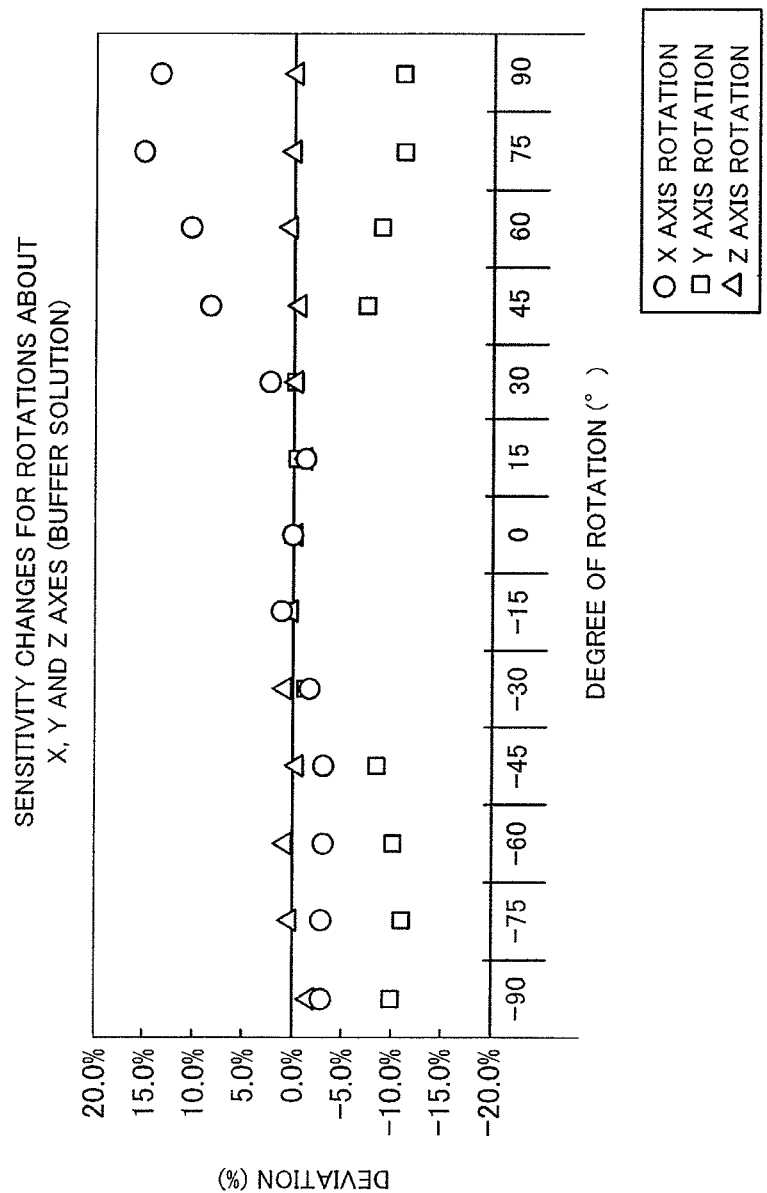
FIG. 6 shows experimental results of sensitivity change of a blood glucose measuring device according to Embodiment 1 with respect to degree of rotation about each axis.
Figure 7:
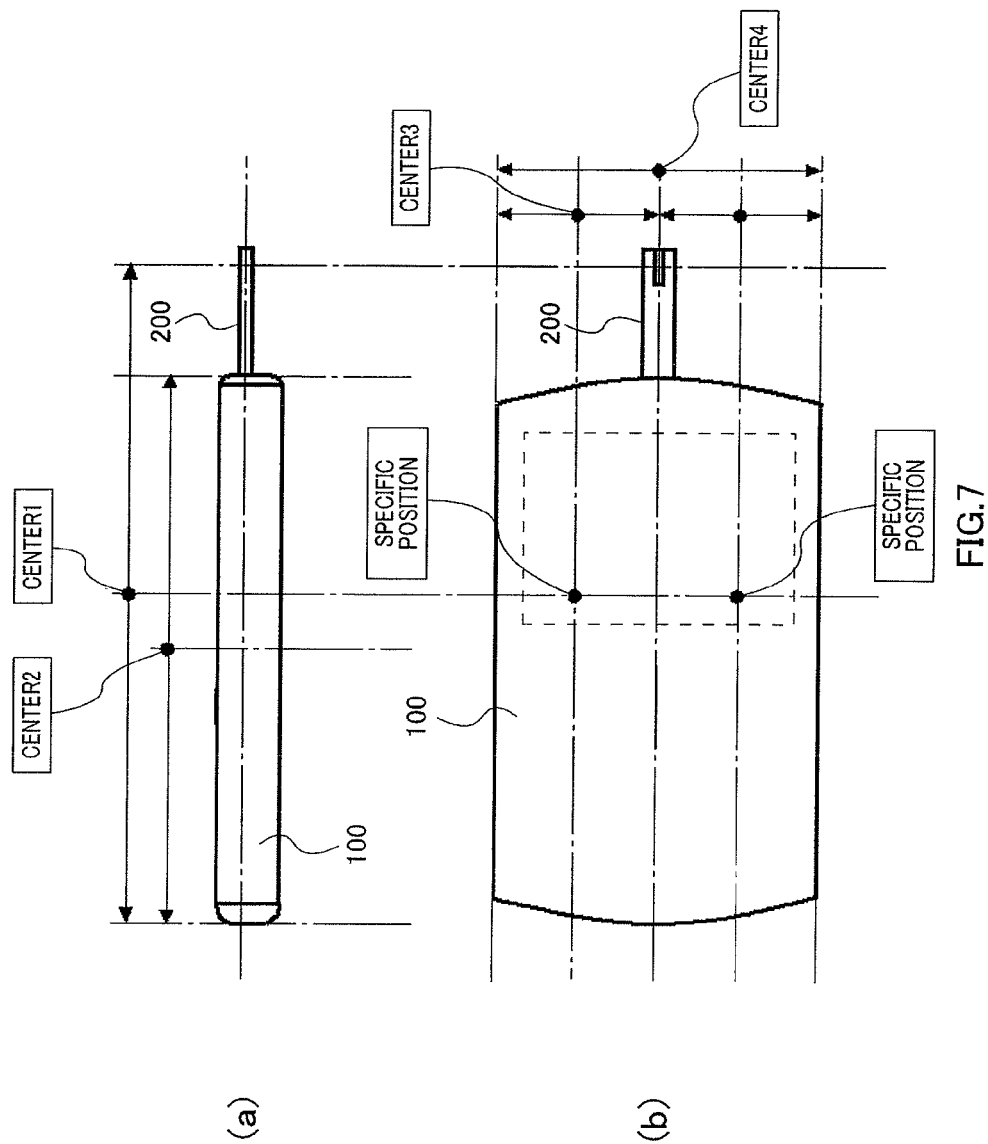
FIGS. 7a and 7b explain the position where an acceleration sensor is attached to a blood glucose measuring device according to Embodiment 1.

FIG. 6 shows how sensitivity changed with changes in the degree of rotation about each axis, wherein the horizontal axis is degree of rotation, and the vertical axis is deviation (%) of concentration. In the graph, ○ denotes sensitivity change for x axis rotation, □ denotes sensitivity change for y axis rotation, and Δ denotes sensitivity change for z axis rotation.

Measurements were made at every 15° of rotation about each axis. As a sample, 450 mg/dl glucose in PBS (phosphate buffered solution) was used. Each point on the plot is an average of 10 measurements.

As shown in FIG. 6, in the case of x axis rotation, the angle dependency of sensitivity was large for positive angle rotation, especially when the device was rotated by 45° or more, showing 8.5% sensitivity increase at a rotation of 45°. Over 13% sensitivity increase was observed at a rotation of 90°. For negative angle rotation, on the other hand, no angle dependency was observed when the device was rotated by 45° or more, showing only approximately 3% sensitivity reduction.

In the case of y axis rotation, large sensitivity reductions were observed for rotation through positive and negative angles when the device was rotated by 45° or more, with sensitivity reduction of as large as approximately 10% at a rotation of 75° or more.

In the case of z axis rotation, sensitivity change was within ±2% of the value of the neutral position over the entire angle range. No sensitivity change attributable to angle changes was confirmed.

It was thus demonstrated that little sensitivity change occurs during measurement when the tilt angle is within ±15°, especially for rotations about the x axis and y axis, and that the biosensor can offer highly reliable, high-precision measurements where the tilt angle is, in view of clinical application, preferably within ±30%.

Although not indicated in the data of FIG. 6, rapid or continuous movements about z axis during measurement results in the generation of a centrifugal force that acts on the liquid reagent in the capillary, making non-uniform the reagent concentration across the reaction region. This leads to poor measurement accuracy and as well as poor system reliability as in the case of where the sensor is tilted about x axis or y axis.

In the blood glucose measuring system according to this embodiment, blood glucose measuring device 100 has acceleration sensor 112. A feature of the present invention is that blood glucose measuring device 100 measures the tilt angle of by means of acceleration sensor 112 and employs the measured angle as a measurement control parameter for improved measurement accuracy.

Next will describe a particular position to which acceleration sensor 112 is attached to the blood glucose measuring system.

With the blood glucose measuring system according to this embodiment, the user holds the biosensor-equipped measuring device with one hand, and holds a lancet with the other hand to puncture the skin and squeezes out a drop of blood, allowing the blood to be introduced into the biosensor from the inlet for blood glucose measurement.

As described above, in the blood glucose measuring system in which a biosensor (blood glucose sensor 200) is attached to a measuring device (blood glucose measuring device 100), the tilt angle of the biosensor's reaction site (i.e., reagent surface) influences the sensor performance. It is therefore necessary to detect the tilt angle of the biosensor with higher precision.

FIGS. 7a and 7b are a side view and a top view, respectively, for explaining the position where acceleration sensor 112 is attached to the measuring device illustrated in FIG. 5.

Referring to FIG. 7a, which illustrates a biosensor (blood glucose sensor 200) attached to a measuring device (blood glucose measuring device 100), center 1 denotes the center between the biosensor's reaction site and the left end of the measuring device, and center 2 denotes the center of the lengthwise side of the measuring device.

Referring to FIG. 7b, center 3 denotes the center between the biosensor's reaction site and the lengthwise side of the measuring device, and center 4 denotes the widthwise center of the measuring device, which corresponds to the widthwise center of the biosensor's reaction site.

The most preferable attachment positions of acceleration sensor 112 are the intersections between the vertical straight line passing through center 1 and the horizontal straight lines respectively passing through centers 3. Hereinafter, the two most preferable attachment positions are called "specific positions."

The reason why the particular position is the most preferable attachment position is as follows. First, acceleration sensor 112 should be deviated from the center axis of the biosensor's reaction site. This is because the amount of detected motion is small if acceleration sensor 112 is coaxial with the reaction site. Second, acceleration sensor 112 should be located on the biosensor attachment side with respect to the device center (center 2). This is because in order allow a user to load a blood sample from the tip of the biosensor while holing the measuring device with one hand, the biosensor attachment side should always come on the outward side of the device, where the amount of movement is large.

Next will describe the operation of the blood glucose measuring system configured as described above.

The blood glucose measuring system includes blood glucose measuring device 100, blood glucose sensor 200, and attachment unit 300, wherein blood glucose measuring device 100 includes sensor attachment part 101 to which an attachable/detachable biosensor (blood glucose sensor 200) is attached. Blood glucose measuring device 100 further includes a motion measurement section (acceleration sensor) 112 for detecting motions of blood glucose measuring device 100 during physical activity.

CPU 110 combines the blood glucose data measured by blood glucose sensor 200 with the data detected by acceleration sensor 112, and executes the following processes, whereby it is made possible to display novel information on display section 102 as well as to accumulate in the recording section data extremely useful of self-monitoring of diabetes.

By way of example, combining the data detected by acceleration sensor 112 with blood glucose data allows for not only precise, automatic detection of exercise or the like, but also accurate blood glucose management based on daily living activities such as eating and sleeping. This is expected to be highly meaningful for improving clinical outcomes by means of blood glucose monitoring.

As described above, the blood glucose measuring system includes blood glucose sensor 200 and blood glucose measuring device 100, as well as includes a motion measurement section (acceleration sensor) 112. CPU 110 combines the data from acceleration sensor 112 with blood glucose data and executes the processes below.

This embodiment describes fundamental operations of living activity measurement and blood glucose measurement as well as new findings obtained by combining living activity data with blood glucose data. Among daily living activities, Embodiment 2 focuses on eating, and Embodiment 3 focuses on sleeping.

Blood glucose measuring device 100 has [living activity measurement mode] as a fundamental operation of living activity measurement, and [blood glucose measurement mode] and [sensor insertion mode] as fundamental operations of blood glucose measurement. Sensor insertion mode detects, prior to blood glucose measurement mode, the proper attachment of blood glucose sensor 200 to sensor attachment part 101 of blood glucose measuring device 100. The respective modes are realized by causing CPU 110 to execute corresponding control programs. Each mode will be described below.

First, living activity measurement mode will be described. As acceleration sensor 112, a sensor that detects and outputs an angle is employed herein.

[Living Activity Measurement Mode]

Figure 8:
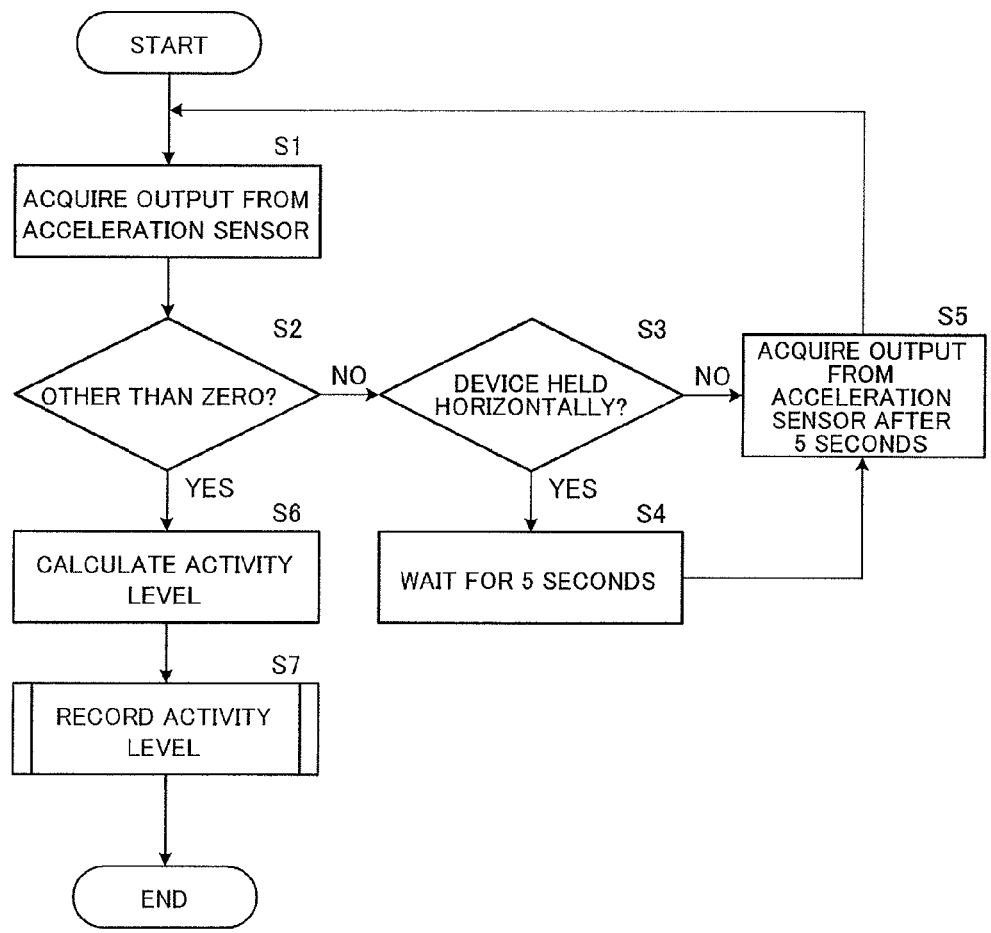
FIG. 8 is a flowchart of living activity measurement mode in a blood glucose measuring device according to Embodiment 1.

FIG. 8 is a flowchart of living activity measurement mode in blood glucose measuring device 100. This flow is repeatedly executed by CPU 110 at predetermined timings. In the drawing, S denotes each step of this flow.

First, in step S1, CPU 110 acquires an output from acceleration sensor 112.

In step S2, CPU 110 determines whether or not the change mount of the output of acceleration sensor 112 is other than zero, i.e., determines whether or not blood glucose measuring device 100 is at rest.

Whet it is determined that the change amount of the output of acceleration sensor 112 is zero, i.e., acceleration sensor 112 detects no motions and only outputs a certain degree of angle, the process proceeds to step S3. When the change amount of the output of acceleration sensor 112 is other than zero, on the other hand, the process proceeds to step S6.

In step S3, CPU 110 determines whether or not the diabetes self-monitoring device (blood glucose measuring device 100) is held horizontally, based on the output of acceleration sensor 112. When CPU 110 has determined that the device is held horizontally, the process then proceeds to step S4 where the device waits for a predetermined time (e.g., 5 seconds) in a horizontal state, and then the process proceeds to step S5. When the device is not held horizontally, the process directly proceeds to step S5.

In step S5, CPU 110 acquires an output from acceleration sensor 112 after a predetermined time (e.g., 5 seconds), and then the process proceeds back to step S1. CPU 110 detects the degree of tilting of the diabetes self-monitoring device (blood glucose measuring device 100). When the device is found to be horizontal, the device waits for at least 5 seconds before receiving an output from acceleration sensor 112. On the other hand, when the device is not held horizontally, the device acquires an output from acceleration sensor 112 5 seconds after the detection. This is to obtain proper output from acceleration sensor 112.

When it is determined in step S2 that the change amount of the output of acceleration sensor 112 is not zero, CPU 110 calculates activity level (living activity level) based on the change amount of the output of acceleration sensor 112 in step S6.

In step S7, CPU 110 records the calculated activity level in recording section 111, and then ends this flow.

The flow of living activity measurement mode in which the orientation angle of blood glucose measuring device 100 with respect to horizontal is detected and CPU 110 acquires an output from acceleration sensor 112 after waiting for a predetermined time (5 seconds in this embodiment) from the detection is one embodiment of [A. high-precision measurement control].

Next will describe blood glucose measurement mode.

[Blood Glucose Measurement Mode 1]

There are two different types of blood glucose measurement modes: blood glucose measurement mode 1 in which the orientation of blood glucose measuring device 100 with respect to horizontal is detected, and blood glucose measurement mode 2 in which the orientation of blood glucose measuring device 100 is not detected. Each mode is switched from sensor insertion mode.

Figure 9:
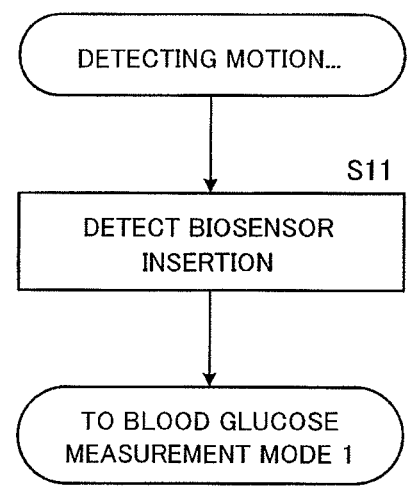
FIG. 9 is a flowchart of sensor insertion mode in a blood glucose measuring device according to Embodiment 1.
Figure 10:
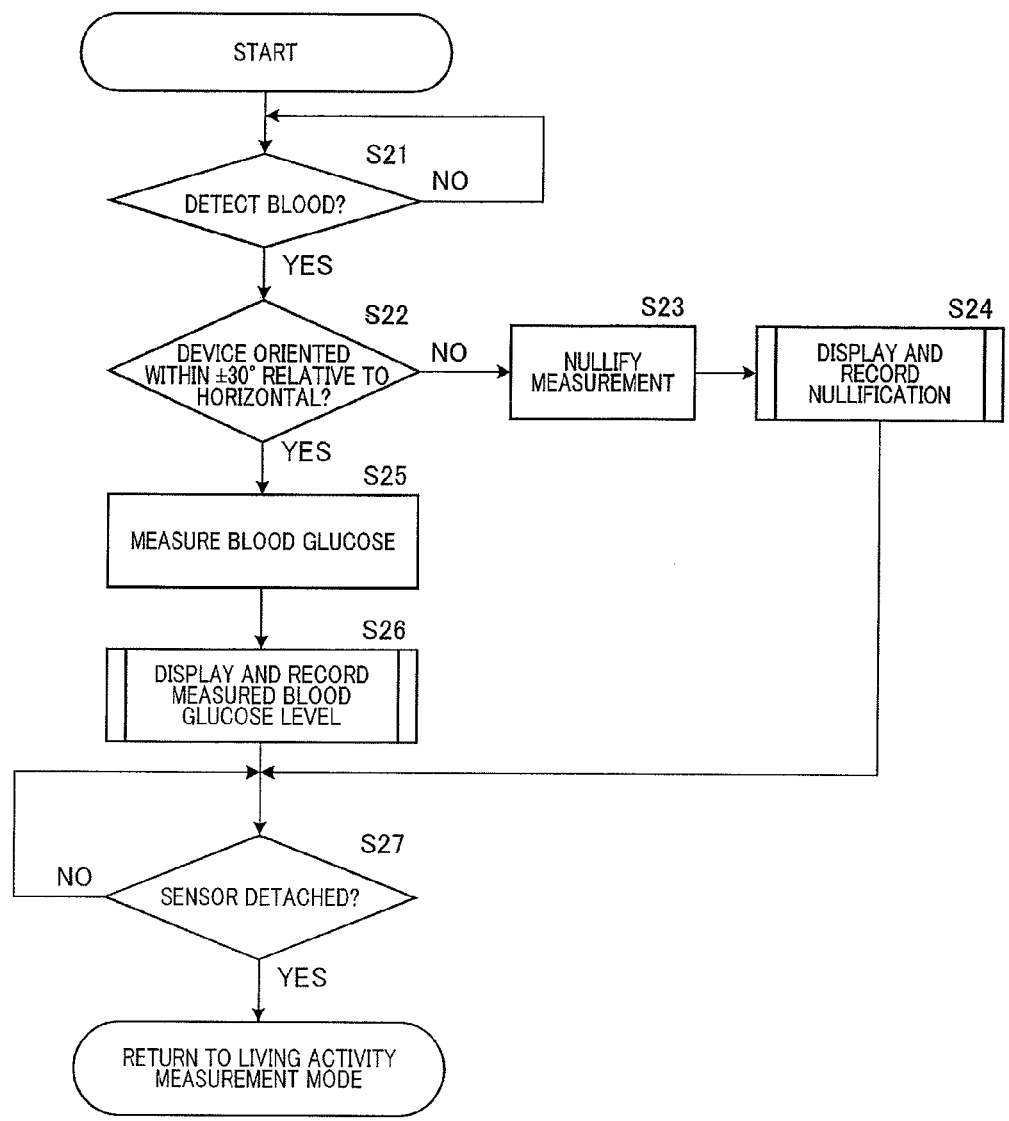
FIG. 10 is a flowchart of blood glucose measurement mode 1 activated after sensor insertion mode in a blood glucose measuring device according to Embodiment 1.

FIG. 9 is a flowchart of sensor insertion mode in blood glucose measuring device 100. FIG. 10 is a flowchart of blood glucose measurement mode 1 activated after sensor insertion mode of FIG. 9.

Sensor insertion mode of FIG. 9 starts during motion measurement, and in step S11 CPU 110 detects whether or not the biosensor (blood glucose sensor 200) has been inserted into sensor attachment part 101 of blood glucose measuring device 100. When blood glucose sensor 200 is inserted to an extent whereby it contacts a contact switch (not shown), sensor insertion mode switches to blood glucose measurement mode 1 (FIG. 10).

When blood glucose measurement mode 1 has started, in step S21, blood glucose measurement circuit section 113 determines whether or not blood has been detected; the process waits until the device confirms the presence of blood. Blood glucose measurement circuit section 113 confirms the presence of blood by receiving detection signals from lead electrodes 211 and 212 of blood glucose sensor 200 (FIG. 2) via connection sections 114 and 115.

When the presence of blood is confirmed, in step S22, CPU 110 confirms the orientation of blood glucose measuring device 100 with respect to the horizontal, determining whether or not the device is held at an angle of within ±30° with respect to the horizontal. CPU 110 can detect the orientation angle of blood glucose measuring device 100 based on the output from acceleration sensor 112.

When the orientation angle of blood glucose measuring device 100 is not within ±30° with respect to the horizontal, CPU 110 nullifies the measured blood glucose level in step S23. The mechanism by which failure to hold blood glucose measuring device 100 in a horizontal state, i.e., tilting of the biosensor (blood glucose sensor 200) attached to sensor attachment part 101 of blood glucose measuring device 100 leads to poor measurement accuracy has been described above. In this embodiment, the measured blood glucose level is nullified as being less reliable when blood glucose measuring device 100 is not held at an angle of within ±30° to the horizontal.

In step S24, with display section 102, CPU 110 notifies the user that blood glucose measurement has been nullified, as well as records the nullification event in recording section 111. The process then proceeds to step S27.

On the other hand, when it is determined in step S22 that blood glucose measuring device 100 is held at an angle of within ±30° with respect to the horizontal, blood glucose measurement circuit section 113 measures blood glucose level in step S25.

In step S26, CPU 110 displays the measured blood glucose level to the user on display section 102, as well as records the measured value in recording section 111. The process then proceeds to step S27.

In step S27, CPU 110 determines whether or not the biosensor (blood glucose sensor 200) has been detached from sensor attachment part 101 of blood glucose measuring device 100. When sensor detachment is detected, the device is switched from blood glucose measurement mode 1 to living activity measurement mode (FIG. 8). Thus, CPU 110 executes living activity measurement mode whenever an event such as blood glucose measurement mode 1 is terminated.

In this way, while blood glucose measurement mode 1 proceeds operations of blood glucose measurement in cases where blood glucose measuring device 100 is held at an angle of within +30° with respect to the horizontal, it notifies the user that the measured blood glucose level has been nullified in cases where blood glucose measuring device 100 is held at an angle over within ±30° with respect to the horizontal.

The flow of blood glucose measurement mode 1 in which it is determined whether or not blood glucose measuring device 100 is held at an angle of within ±30° with respect to the horizontal followed by blood glucose measurement is one embodiment of [A. high-precision measurement control]. The significance of limiting the tilting angle to −30° to 30° has been described with reference to FIG. 6.

[Blood Glucose Measurement Mode 2]

Blood glucose measurement mode 2 stops the operation of acceleration sensor (motion measurement section) 112 upon attachment of the biosensor (blood glucose sensor 200) to sensor attachment part 101 of blood glucose measuring device 100.

Figure 11:
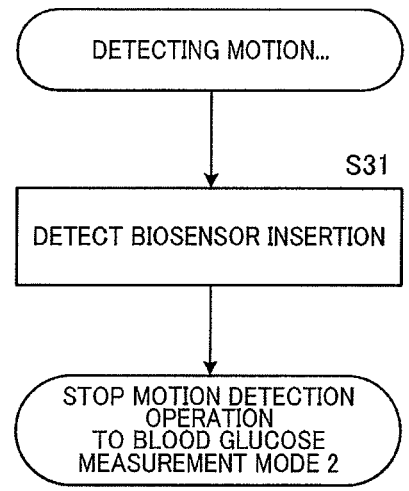
FIG. 11 is a flowchart of sensor insertion mode in a blood glucose measuring device according to Embodiment 1.
Figure 12:
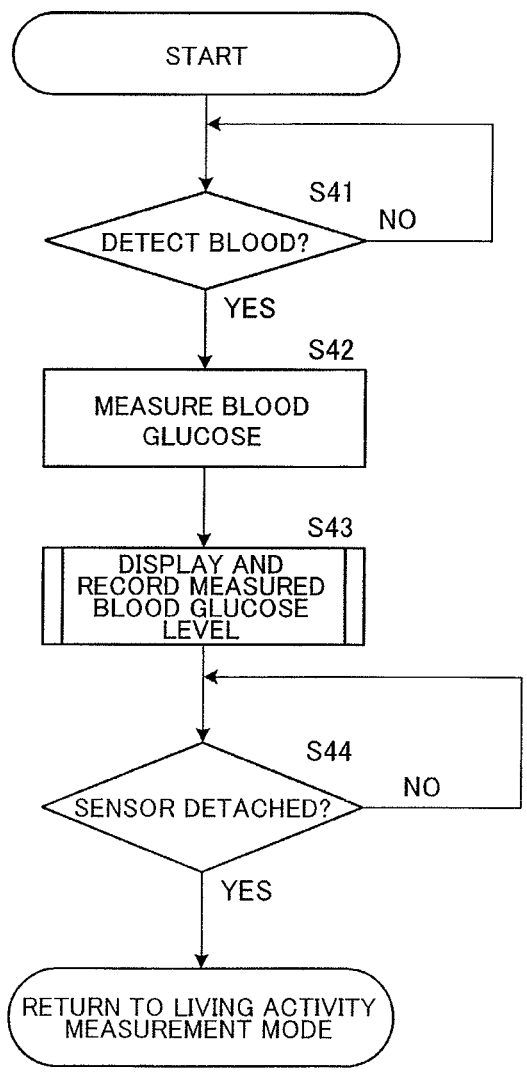
FIG. 12 is a flowchart of blood glucose measurement mode 2 activated after sensor insertion mode in a blood glucose measuring device according to Embodiment 1.

FIG. 11 is a flowchart of sensor insertion mode in blood glucose measuring device 100. FIG. 12 is a flowchart of blood glucose measurement mode 2 activated after sensor insertion mode of FIG. 11.

Sensor insertion mode of FIG. 11 starts during motion measurement, and in step S31 CPU 110 detects whether or not the biosensor (blood glucose sensor 200) has been inserted into sensor attachment part 101 of blood glucose measuring device 100. When blood glucose sensor 200 is inserted to an extent whereby it contacts a contact switch (not shown), sensor insertion mode switches to blood glucose measurement mode 2 (FIG. 12).

When blood glucose measurement mode 2 starts, in step S41, blood glucose measurement circuit section 113 determines whether or not blood has been detected; the process waits until the device confirms the presence of blood. Blood glucose measurement circuit section 113 confirms the presence of blood by receiving detection signals from lead electrodes 211 and 212 of blood glucose sensor 200 (FIG. 2) via connection sections 114 and 115.

When the presence of blood has been detected, blood glucose measurement circuit section 113 measures blood glucose level in step S42.

In step S43, CPU 110 displays the measured blood glucose level to the user on display section 102, as well as records the measured value in recording section 111. The process then proceeds to step S44.

In step S44, CPU 110 determines whether or not the biosensor (blood glucose sensor 200) has been detached from sensor attachment part 101 of blood glucose measuring device 100. When sensor detachment is detected, the device is switched from blood glucose measurement mode 2 to living activity measurement mode (FIG. 8). Thus, CPU 110 executes living activity measurement mode whenever an event such as blood glucose measurement mode 2 is terminated.

By performing the flows described above, it is possible to combine data of acceleration sensor 112 and data of blood glucose level to realize new display and record. The following details a display example of measurement results, which corresponds to the description of [B. living activity measurement control] described above.

First, the user inputs his/her personal data (age, height, weight and gender), as it is necessary to determine basal metabolism to keep track of living activity level. The input values are calculated to find user's basal metabolism standard. Using the basal metabolism standard, basal metabolism rate is calculated and recorded in recording section 111.

Next will describe readings of blood glucose measuring device 100 worn slightly below the waist.

First, the display of living activity levels on a day will be described.

Figure 13:
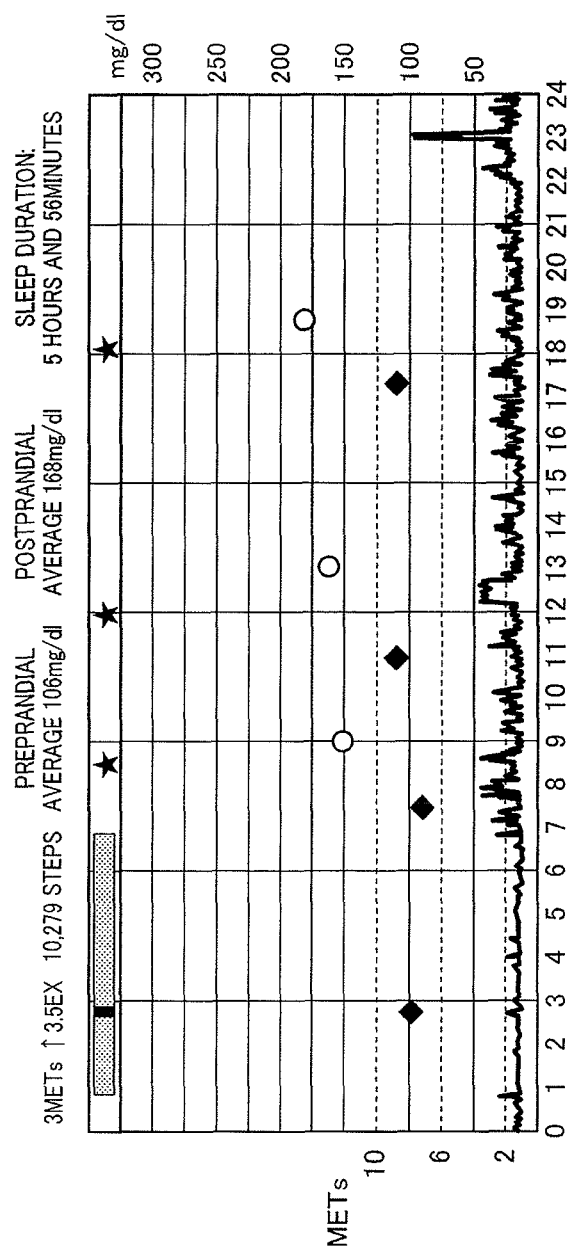
FIG. 13 shows readings of living activity level on a day, as measured with a blood glucose measuring device according to Embodiment 1.

FIG. 13 shows living activity readings of a day measured with blood glucose measuring device 100, wherein the horizontal axis is time in a 24-hour format, and vertical axis is living activity level and blood glucose level. The data is collected on a day-to-day basis by resetting the timer every 0:00 am.

This graph shows a measurement result for a particular day. In the graph, the line represents the measured living activity level, and a plot represents blood glucose levels. From the graph it can be seen that living activity level constantly changes with changes in living activity from wake-up to sleep. In the graph living activity level is indicated as a value averaged on a minute-to-minute basis.

Regarding events, in FIG. 13, ★ denotes meal, a shaded bar denotes a sleeping period, and blood glucose measurement during sleeping is denoted by a solid bar.

Referring to the upper portion of the graph, activity level equivalent to 3 METs or greater is indicated as EX (exercise). Also, preprandial and postprandial blood glucose levels, and sleep duration are indicated. The time at which the measuring device properly measured blood glucose level is excluded from the sleep duration. The type of display of activity levels can be freely changed at the user's end; for example, the user can switch the displayed activity levels equivalent to less than 3 METs to "Weak Activity", activity levels equivalent to between 3 METs and 4 METs to "Moderate Activity", and activity levels equivalent to 4 METs or greater to "Vigorous Activity" or "Exercise".

Displaying the measurement result on a daily basis in this way also allows patients by themselves to check their activity levels against living activity levels. Moreover, the measurement date (year, month and day) is also displayed in the display window, so that the user can retrieve data of a particular day.

Next will describe displaying measured values of living activity level in a 1-month trend graph.

Figure 14:
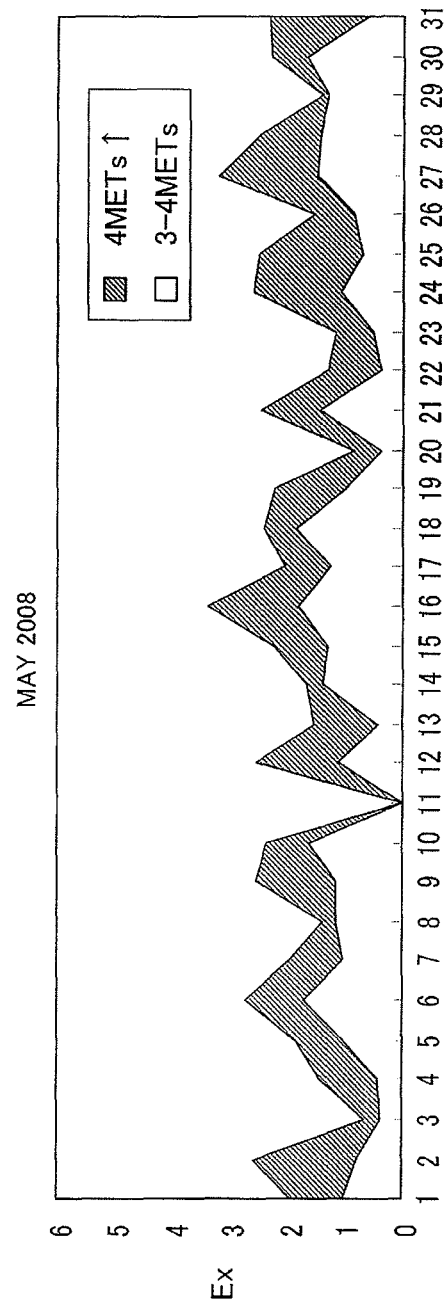
FIG. 14 is a 1-month trend graph of living activity levels as measured with a blood glucose measuring device according to Embodiment 1.

FIG. 14 shows a 1-month trend graph of living activity levels, wherein the vertical axis is the amount of exercise (EX) expressed in terms of METs multiplied by time.

This graph shows an example in which living activity levels of a day are indicated in terms of the amount of exercise by classifying them according to intensity. In this graph, the amounts of exercise are classified according to whether the living activity level is between 3 METs and 4 METs or greater than 4 METs.

In this example, the user tried to carry the measuring system everyday for one month, but failed on May 11th as he was sick in bed for a full day; no records were obtained. In view of the possibility that the user forgets or cannot to carry the device for some reasons, it is preferable that the device can selectively exclude the living activity level and blood glucose level. From the graph it can be seen that living activity level greatly varies from one day to another.

In this graph, the amounts of exercise are not classified according to whether they are measured on holidays (e.g., Saturday and Sunday) or other days. As living activity level varies depending on the person's daily rhythm, it is also preferable to classify the amounts of exercise according to whether measurements are made on holidays or other days or in consideration of the user's daily rhythm. Moreover, it is preferable to previously input special days (e.g., sick days) for later confirmation. Sick days are preferably designated as "Sick" on the screen.

Next will describe displaying measured values of living activity level in a 1-year trend graph.

Figure 15:
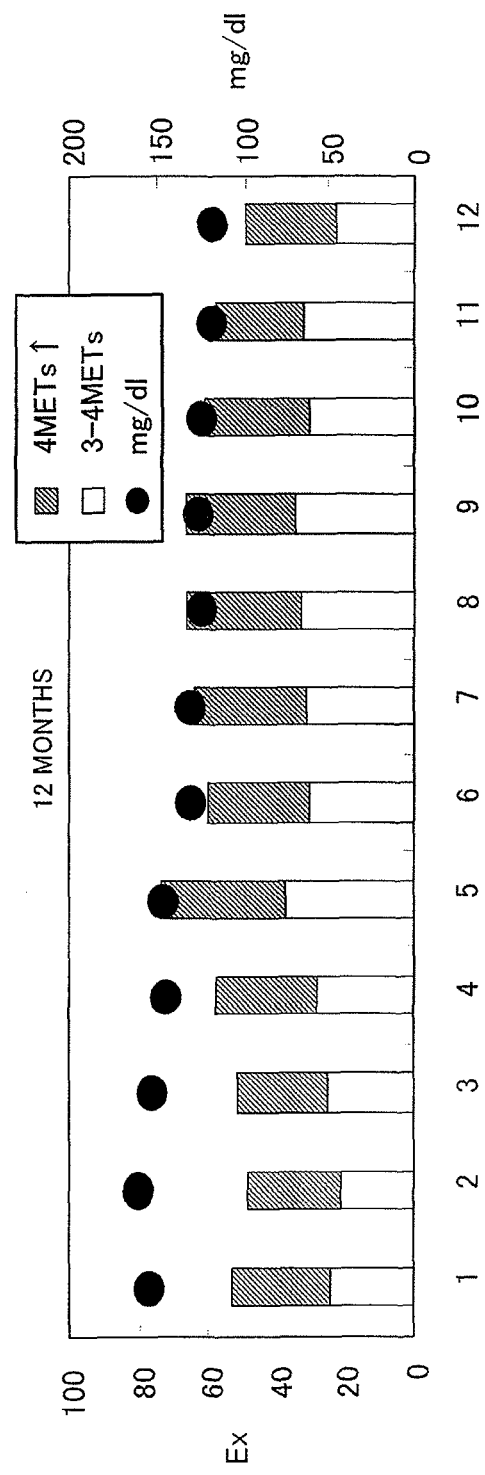
FIG. 15 is a 1-year trend graph of living activity levels and blood glucose levels as measured with a blood glucose measuring device according to Embodiment 1.

FIG. 15 is a 1-year trend graph of monthly living activity levels and blood glucose levels, wherein the horizontal axis is month, the left vertical axis is monthly total amount of exercise, and the right vertical axis is blood glucose level.

In this graph, each blood glucose reading is the daily average of blood glucose levels of the month. As blood glucose level varies significantly throughout the day, e.g., depending on whether preprandial or postprandial, blood glucose readings may also be classified according whether they are preprandial or postprandial values, or whether they are overnight fasting blood glucose levels. In view of the fact some months have different days and that the frequency at which the user forgets to carry the device changes from one month to another, it is also preferable to average living activity levels by dividing the total of the living activity levels by the number of the days in which the user worn the device, rather than the total number of the days of the month.

This graph is a 1-year trend graph of blood glucose levels.

Only small changes are observed in blood glucose level among three consecutive months. Moreover, the amounts of changes in blood glucose level are difficult to monitor because it is often influenced by the subject's physical condition and because measurement frequency data is difficult to manage. By displaying a 1-year trend of blood glucose levels in this way, it can be clearly understood that blood glucose level decreased over the 12 months.

By providing blood glucose measuring device 100 with a HbA1c measurement/input function, HbA1c level, a long-term indicator of diabetes, can be displayed. In addition to HbA1c, glycoalbumin, fluctosamine, and/or 1,5AG (1,5-anhydro-D-glucitol) may be measured with blood glucose measuring device 100.

As described above, blood glucose measuring device 100 according to this embodiment includes blood glucose sensor 200 and acceleration sensor 112 which measures motions of physical activity, wherein CPU 110 controls the measurement operation of blood glucose measurement circuit section 113 based on the motion information ([A. high-precision measurement control]).

CPU 110 also records in recording section 111, and displays on display section 102 displays, the measured blood glucose level and the motion information measured by acceleration sensor 112 while associating them with each other ([B. living activity measurement control]). CPU 110 also combines the blood glucose levels measured by blood glucose sensor 200 with the data detected by acceleration sensor 112, and executes each mode processing.

In this way it is possible to display novel information on display section 102 as well as to accumulate in the recording section 111 data that is extremely useful of self-monitoring of diabetes. It is also made possible to realize accurate blood glucose management based on daily living activities such as eating and sleeping. These achievements are expected to be highly meaningful for improving clinical outcomes by means of blood glucose monitoring.

In particular, blood glucose measuring device 100 according to this embodiment offers a unique effect that enables blood glucose level and living activity level to be measured with one device. This allows diabetic patients to live a more healthy life, as well as allows medical practitioners to easily keep track of living activity levels and blood glucose levels. Moreover, clinical activities become more beneficial to diabetic patients. When a measuring device that can provide the above effect with one circuit board is realized, the device can be utilized as a low-cost blood glucose measuring device designed to measure the living activity level as well.

It is preferable that the power source such as a battery used in blood glucose measuring device 100 be durable as well as have a long life for improving handleability and ensuring storage of recorded data. For this reason, it is preferable to employ a rechargeable (secondary) battery or a solar battery, or to utilize power generation using human movements, so that the power source can be recharged during use. It is also important to display the remaining amount of the battery on display section 102. Moreover, the configuration of blood glucose measuring device 100 can be changed depending on the need. For example, the detection frequency of acceleration by acceleration sensor 112 may be altered in order to reduce power consumption while ensuring the precision of the measurement of living activity level.

Blood glucose measuring device 100 may be connected with a computer via computer interface 116. This computer may be used by a medical practitioner such as a doctor or by a patient himself for self-monitoring. In the latter case, blood glucose measuring device 100 is called a diabetes self-monitoring device in some cases.

An example in which blood glucose measuring device 100 is connected with a computer via computer interface 116 for detailed analysis will be described in Embodiment 12.

The living activity levels and blood glucose levels thus measured are sent to the computer via computer interface 116, and the computer executes [C. detailed analysis control]. This computer stores patients' personal data (e.g., age, height, weight, gender, and basal metabolism standard).

With the data transferred to the computer, the measurement data can be processed in formats that enable users to more easily monitor their blood glucose level and living activity level, in addition to showing them in 1-day, 1-month and 1-year trend graphs. With blood glucose measuring device 100, highly health-conscious individuals as well as diabetic patients can monitor their blood glucose level and living activity level from an objective standpoint.

Thus, even in situations where patients cannot keep the motivation to measure blood glucose level on a daily basis, blood glucose measuring device 100 allow the users to keep the motivation to exercise and monitor their blood glucose level. In this way adult diseases and complications of diabetes can be prevented, as well as good blood glucose control can be realized.

Accumulating data in a computer not only enables medical practitioners such as doctors, nurses and diabetes care providers to give proper instructions or advice to diabetic patients from the viewpoint of their daily activity and blood glucose monitoring, but also realizes sharing of information via a computer network.

Embodiment 2

In Embodiment 1, improved blood glucose management based on living activity as shown in FIGS. 13 to 15 has been realized by combining the blood glucose levels measured by the biosensor (blood glucose sensor 200) and with living activity levels measured by motion measurement (acceleration sensor) 112. Embodiment 2 will describe how meal events are detected.

The hardware configuration of a blood glucose measuring system according to Embodiment 2 of the present invention is identical to that illustrated in FIGS. 1 to 3. In this embodiment, CPU 110 serves as meal time setting means as described below, which sets meal time and the number of meals.

Next will describe how meal events are detected, as well as the importance of detecting meal events.

Clinically, detection of meal events is critical. For diabetic patients, the relationship between meal and blood glucose level is particularly important for the following reason: The amount of sugar in food directly affects blood glucose levels, significantly elevating blood glucose levels particularly in diabetic patients receiving insulin therapy. Thus, for proper blood glucose management, monitoring when and at what time meals are given is as important for medical practitioners as it is for diabetic patients who inject insulin by themselves.

Conventionally, however, in order for diabetic patients to leave their records for medical practitioners, they have no choice but to manually input in the device or to take notes as to whether blood glucose measurement is preprandial or postprandial; many of the patients feel burden to leave records and fail to do so. Thus, conventionally, proper blood glucose management has been very difficult.

This embodiment automatically and precisely determines and records whether blood glucose measurement, which is clinically important, is made preprandially or postprandially, without bothering users.

Next will describe meal event detection processing.

[Meal Event Detection Processing Mode 1]

There are two different meal event detection processing modes: [Meal event detection processing mode 1], a basic meal event detection mode, and [Meal event detection processing mode 2] in which meal events—breakfast, lunch, and dinner—are detected. Each mode is switched from [blood glucose measurement mode].

Figure 16:
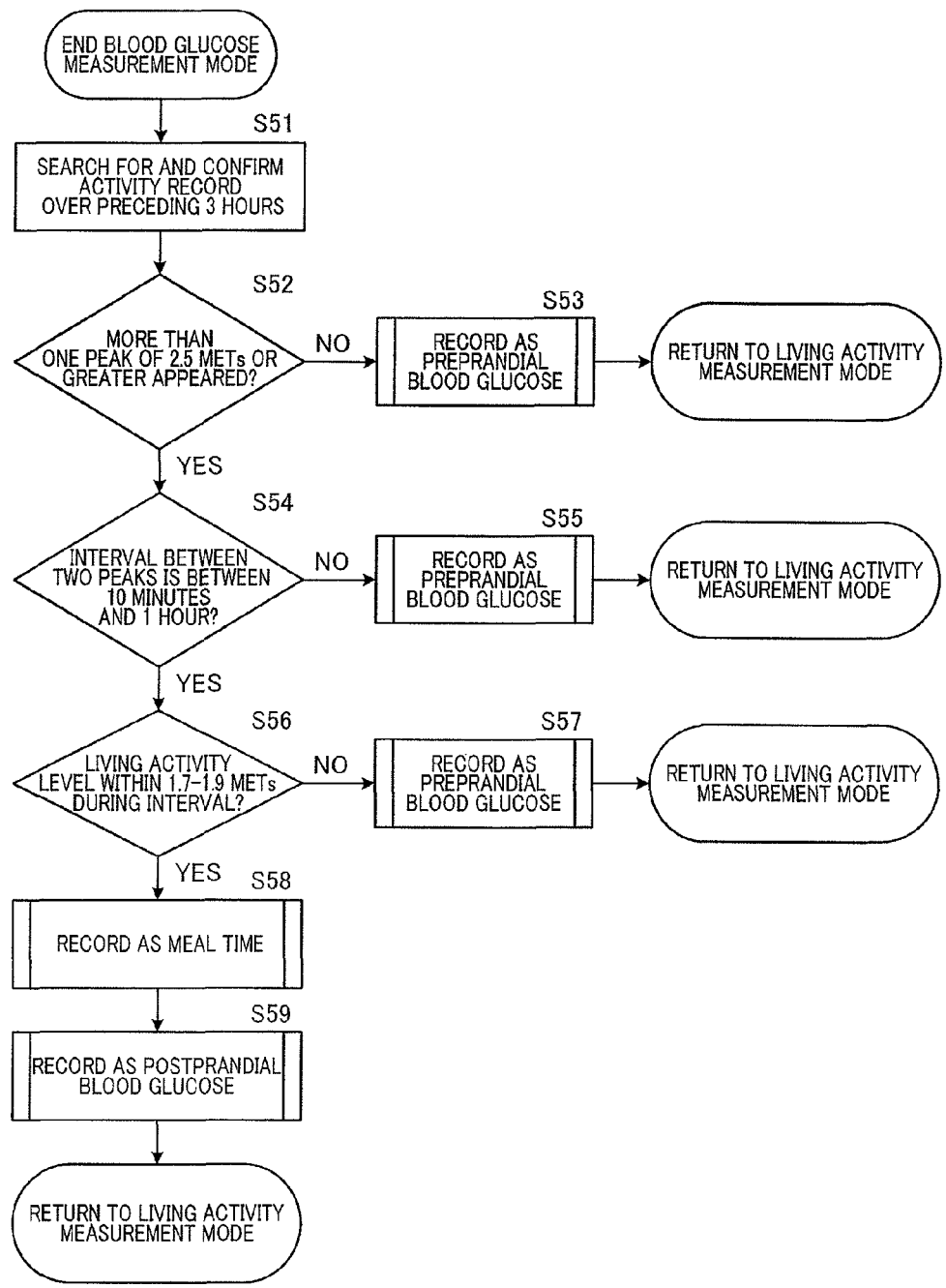
FIG. 16 is a flowchart of meal event detection processing mode 1 in a blood glucose measuring device according to Embodiment 2.

FIG. 16 is a flowchart of meal event detection processing mode 1 in blood glucose measuring device 100. This flow is repeatedly executed by CPU 110 (FIG. 2) at predetermined timings.

[Meal event detection processing mode 1] is activated by the completion of [blood glucose measurement mode 1] or [blood glucose measurement mode 2]. In step S51, CPU 110 searches recording section 111 for the living activity record over the preceding 3 hours. For example, CPU 110 retrieves a living activity pattern like that shown in FIG. 13 over the preceding 3 hours.

In step S52, CPU 110 determines whether or not two or more waves that equal to or greater than a predetermined living activity level (e.g., 2.5 METs) appeared over the preceding 3 hours.

In this embodiment, movements to and from an eating place, or preparations and doing the dishes, are supposed to be involved before and after a meal and be detected as activities each equivalent to 2.5 METs.

The threshold living activity level used to identify such activities is not limited to 2.5 METs; it can be appropriately set to any level, e.g., 2 to 3 METs, a range within which general moving activity falls.

When it is determined that two or more waves that are equal to or higher than 2.5 METs did not appeared over the preceding 3 hours, in step S53, CPU 110 records in recording section 111 the fact that the last blood glucose level is preprandial blood glucose level. Thereafter, CPU 110 switches the device from [meal event detection processing mode 1] to [living activity measurement mode] (FIG. 8).

On the other hand, when it is determined that two or more waves that are equal to or higher than 2.5 METs appeared over the preceding 3 hours, the process proceeds to step S54.

In step S54, CPU 110 determines whether or not the interval between the two waves is 10 minutes to 1 hour.

When the interval between the two waves is either less than 10 minutes or more than 1 hour, in step S55, CPU 110 records in recording section 111 the fact that the last blood glucose level is preprandial blood glucose level. Thereafter, CPU 110 switches the device from [meal event detection processing mode 1] to [living activity measurement mode] (FIG. 8).

On the other hand, when it is determined in step S54 that the interval between the two waves is 10 minutes to 1 hour, the process proceeds to step S56.

In step S56, CPU 110 determines whether or not the living activity level between the two waves falls within 1.7 to 1.9 METs. This step is based on the fact that the living activity level during a meal is generally from 1.7 to 1.9 METs on average. This range may be changed among different individuals as needed.

When the living activity level between the two waves falls outside the range of 1.7 to 1.9 METs, in step S57, CPU 110 records in recording section 111 the fact that the last blood glucose level is preprandial blood glucose level. Thereafter, CPU 110 switches the device from [meal event detection processing mode 1] to [living activity measurement mode] (FIG. 8).

On the other hand, when it is determined in step S56 that the living activity level between the two waves falls within the range of 1.7 to 1.9 METs, the process proceeds to step S58.

In step S58, CPU 110 records in recording section 111 the fact that a meal was taken during that period. In step S59, CPU 110 then records in recording section 111 the fact that the last blood glucose level is postprandial blood glucose level. Thereafter, CPU 110 switches the device from [meal event detection processing mode 1] to [living activity measurement mode] (FIG. 8).

Specifically, it is judged that a meal has been eaten only where two waves of 2.5 METs or greater are identified during a time period of 10 minutes to 1 hour and the living activity level between the two waves is 1.7 to 1.9 METs, deeming the last blood glucose level as postprandial blood glucose level. As long as this condition is not satisfied, all measured blood glucose levels are deemed as preprandial blood glucose levels.

[Meal Event Detection Processing Mode 2]

Figure 17:
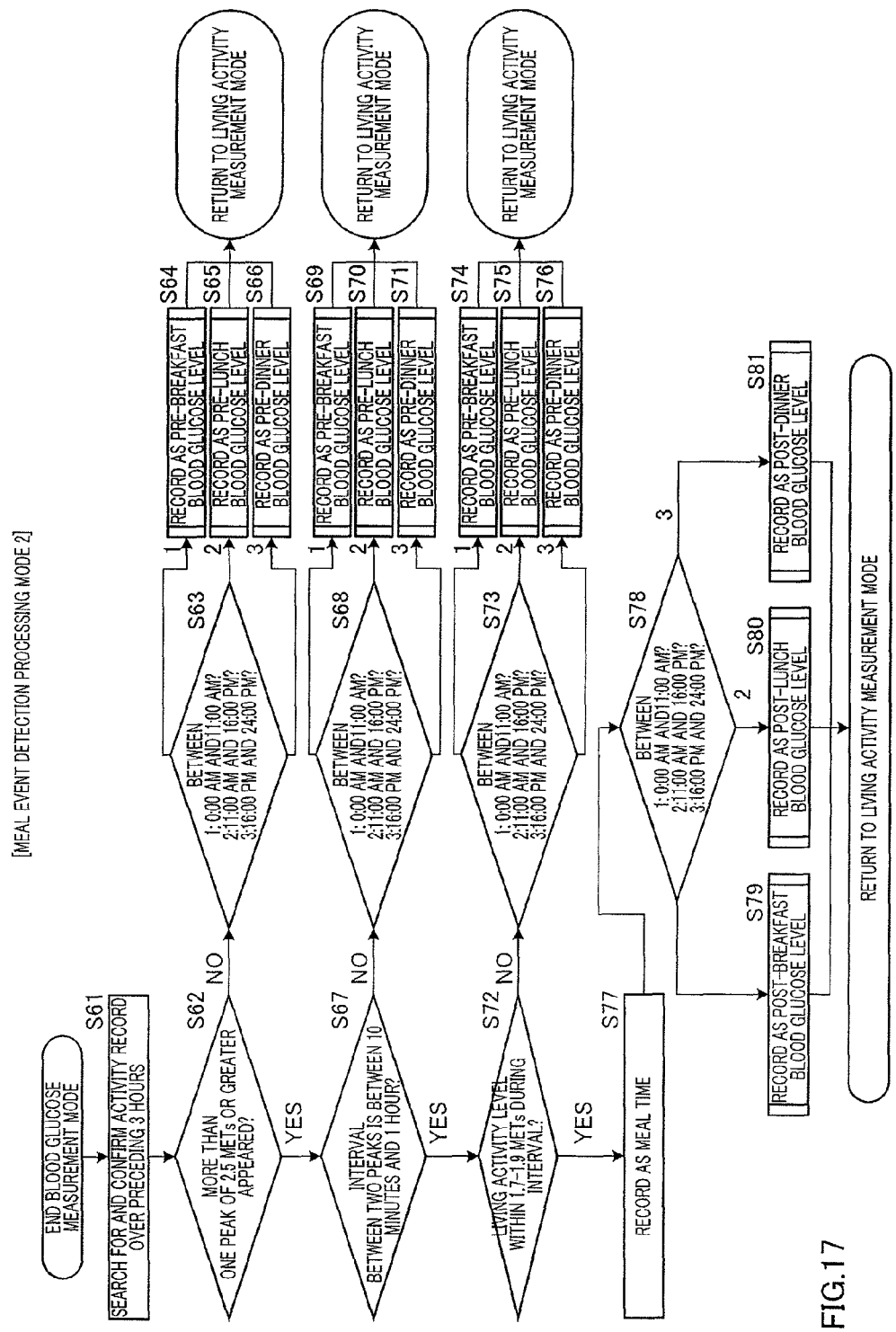
FIG. 17 is a flowchart of meal event detection processing mode 2 in a blood glucose measuring device according to Embodiment 2.

FIG. 17 is a flowchart of meal event detection processing mode 2 in blood glucose measuring device 100.

[Meal event detection processing mode 2] is activated by the completion of [blood glucose measurement mode 1] or [blood glucose measurement mode 2]. In step S61, CPU 110 searches recording section 111 for the living activity record over the preceding 3 hours. For example, CPU 110 confirms a living activity pattern like that shown in FIG. 13 over the preceding 3 hours.

Basically, criteria used to determine the occurrence of a meal event in [meal event detection processing mode 2] are substantially identical to those of [meal event detection processing mode 1] except that time zones are also taken into consideration.

In step S62, CPU 110 determines whether or not two or more waves that are equal to or greater than 2.5 METs appeared over the preceding 3 hours.

When two or more waves that are equal to or higher than 2.5 METs did not appear over the preceding 3 hours, CPU 110 then determines in step S63 as to whether the time zone is between 0:00 am and 11:00 am, between 11:00 am and 16:00 pm, or between 16:00 pm and 24:00 pm.

When the time zone is between 0:00 am and 11:00 am, in step S64, CPU 110 records in recording section 111 the fact that the last blood glucose level is pre-breakfast blood glucose level. When the time zone is between 11:00 am and 16:00 pm, in step S65, CPU 110 records in recording section 111 the fact that the last blood glucose level is pre-lunch blood glucose level. When the time zone is between 16:00 pm and 24:00 pm, in step S66, CPU 110 records in recording section 111 the fact that the last blood glucose level is pre-dinner blood glucose level.

After recording of a preprandial blood glucose level, CPU 110 switches the device from [meal detection processing mode 2] to [living activity measurement mode] (FIG. 8).

When two or more waves that are equal to or higher than 2.5 METs were identified over the preceding 3 hours in step S62, the process proceeds to step S67.

In step S67, CPU 110 then determines whether or not the interval between the two waves is 10 minutes to 1 hour.

When the interval between the two waves is either less than 10 minutes or more than 1 hour, in step S68, CPU 110 then determines in step S63 as to whether the time zone is between 0:00 am and 11:00 am, between 11:00 am and 16:00 pm, or between 16:00 pm and 24:00 pm.

When the time zone is between 0:00 am and 11:00 am, in step S69, CPU 110 records in recording section 111 the fact that the last blood glucose level is pre-breakfast blood glucose level. When the time zone is between 11:00 am and 16:00 pm, in step S70, CPU 110 records in recording section 111 the fact that the last blood glucose level is pre-lunch blood glucose level. When the time zone is between 16:00 pm and 24:00 pm, in step S71, CPU 110 records in recording section 111 the fact that the last blood glucose level is pre-dinner blood glucose level.

After recording of a preprandial blood glucose level, CPU 110 switched the device from [meal detection processing mode 2] to [living activity measurement mode] (FIG. 8).

When it is determined in step S67 that the interval between the two waves that are equal to or higher than 2.5 METs is 10 minutes to 1 hour, the process proceeds to step S72.

In step S72, CPU 110 then determines whether or not the living activity level between the two waves falls within 1.7 to 1.9 METs.

When the living activity level between the two waves falls outside the range of 1.7 to 1.9 METs, in step S73, CPU 110 determines whether the time zone is between 0:00 am and 11:00 am, between 11:00 am and 16:00 pm, or between 16:00 pm and 24:00 pm.

When the time zone is between 0:00 am and 11:00 am, in step S74, CPU 110 records in recording section 111 the fact that the last blood glucose level is pre-breakfast blood glucose level. When the time zone is between 11:00 am and 16:00 pm, in step S75, CPU 110 records in recording section 111 the fact that the last blood glucose level is pre-lunch blood glucose level. When the time zone is between 16:00 pm and 24:00 pm, in step S76, CPU 110 records in recording section 111 the fact that the last blood glucose level is pre-dinner blood glucose level.

After recording of a preprandial blood glucose level, CPU 110 switches the device from [meal detection processing mode 2] to [living activity measurement mode] (FIG. 8).

When it is determined in step S72 that the interval between the two waves that are equal to or higher than 2.5 METs is 10 minutes to 1 hour, the process proceeds to step S77.

In step S77, CPU 110 records in recording section 111 the fact that a meal was taken during that period.

In step S78, CPU 110 determines whether the time zone is between 0:00 am and 11:00 am, between 11:00 am and 16:00 pm, or between 16:00 pm and 24:00 pm.

When the time zone is between 0:00 am and 11:00 am, in step S79, CPU 110 records in recording section 111 the fact that the last blood glucose level is post-breakfast blood glucose level. When the time zone is between 11:00 am and 16:00 pm, in step S80, CPU 110 records in recording section 111 the fact that the last blood glucose level is post-lunch blood glucose level. When the time zone is between 16:00 pm and 24:00 pm, in step S81, CPU 110 records in recording section 111 the fact that the last blood glucose level is post-dinner blood glucose level.

After recording of a preprandial blood glucose level, CPU 110 switches the device from [meal detection processing mode 2] to [living activity measurement mode] (FIG. 8).

Specifically, [meal event detection mode 2] is one which makes it possible confirm the time zone in which blood glucose measurement was made (breakfast, lunch or dinner time zone), in addition to [meal event detection mode 1].

By executing the above flow meal times are detected automatically, and then a list of postprandial blood glucose levels can be displayed to the user at any desired timing.

FIGS. 18 and 19 show a list of preprandial and postprandial blood glucose levels.

FIG. 18 lists preprandial blood glucose levels on the left column and postprandial blood glucose levels on the right column. For example, CPU 110 displays a list of measured blood glucose levels on display section 102 (see FIG. 1) of blood glucose measuring device 100.

As shown in FIG. 18, an average blood glucose level during a given period is displayed on the top of each column. When a given blood glucose level is selected, date, time, feedback symbols of blood glucose management and the like are also highlighted as shown in FIG. 18 or boxed for user's recognition.

In FIG. 18, average blood glucose levels over the preceding 2 weeks as of the selected measurement day are displayed by way of example. However, it is also possible to display average values over the next 2 weeks as of the selected measurement day.

Measured preprandial or postprandial blood glucose levels may be averaged on a daily basis, weekly basis, 2, 3 or 4 week basis, or 30 day basis. Moreover, all values of measured blood glucose level may be averaged. In FIG. 18, the symbol "▲" indicates that the user can select other data not displayed.

As shown in FIG. 19, blood glucose levels may be displayed in the order in which they were measured. In this case, in FIG. 19, data are classified by whether measurement was made preprandially or postprandially, by using the symbol "♪" (indicative of preprandial) and the symbol "!" (indicative of postprandial) for user's confirmation. The number of the symbol is used a measure of the time lapsed after a meal. Other symbols may also be used.

According to this embodiment, it is thus made possible to automatically and precisely determine and record whether blood glucose measurement, which is clinically important, was made preprandially or postprandially, without bothering users, thereby realizing for the first time accurate blood glucose management based on daily living activities such as eating and sleeping. These achievements are expected to be highly meaningful for improving clinical outcomes by means of blood glucose monitoring.

Embodiment 3

In Embodiment 2, meal events have been described as one example of living activities. Embodiment 3 will describe sleep events as one example of living activities.

The hardware configuration of a blood glucose measuring system according to Embodiment 3 of the present invention is identical to that illustrated in FIGS. 1 to 3.

Next will describe detection of sleep events, as well as the importance of detecting sleep events.

Clinically, detection of sleep events is critical. For diabetic patients, the relationship between sleep and blood glucose level is particularly important for the reason as will be described below.

Development of sleep apnea syndrome, a sympthon often seen in diabetic patients, results in significant elevation of blood glucose level; therefore, it is critical for medical practitioners to obtain a sleep history that addresses how long the patient sleeps, how well he/she sleeps, etc., for proper blood glucose management. However, as monitoring of sleeping condition using a general accelerometer has not yet been adopted clinically, there is no choice but to instruct patients to record their sleeping condition on a notebook from their point of view.

Thus, the current situation is that proper blood glucose management is extremely difficult to achieve, because diabetic patients feel it is burdensome to take a sleep history and many of them quit recording sleep condition and sleep duration. Moreover, for severe diabetic patients, like those who receive insulin pump therapy, blood glucose measurement should be made early in the morning around 3:00 am, in view of significant blood glucose elevation in the early morning hours due to the dawn phenomenon as well as for the purpose of adjusting insulin dosage.

Even if an acceleration sensor is used alone to detect sleep condition, activity level accosited with blood glucose measurement is almost equal to that associated with rolling over in the bed. For this reason, it does not reflect the actual sleeping condition and the actual living activity level.

In this embodiment, the exact sleep duration as well as sleep condition, which are clinically important, can be measured and recorded properly and accurately without bothering users.

Next will describe sleep processing.

There are two different sleep processing modes: [sleep processing mode 1] which is a fundamental mode for detecting sleep events, and [sleep processing mode 2] that detects sleep events during a given period. Each mode is switched from [blood glucose measurement mode].

[Sleep Processing Mode 1]

Figure 20:
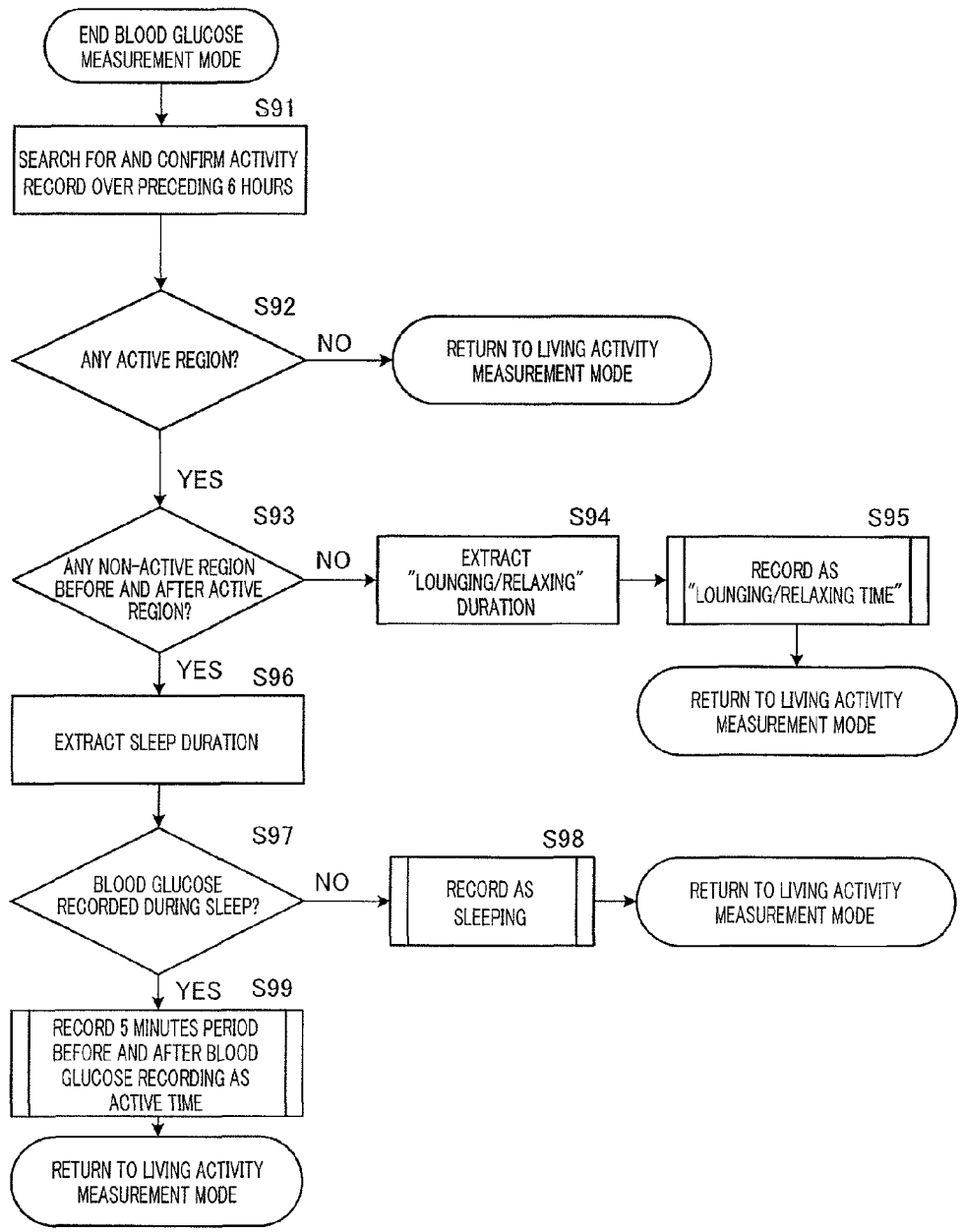
FIG. 20 is a flowchart of sleep processing mode 1 in a blood glucose measuring device according to Embodiment 3.

FIG. 20 is a flowchart of sleep processing mode 1 in blood glucose measuring device 100. This flow is repeatedly executed by CPU 110 (FIG. 2) at predetermined timings.

[Sleep processing mode 1] is activated by the completion of [blood glucose measurement mode 1] or [blood glucose measurement mode 2]. In step S91, CPU 110 searches recording section 111 for the living activity record over the preceding 6 hours. For example, CPU 110 retrieves a pattern of living activity level like that shown in FIG. 13 over the preceding 6 hours.

The living activity levels during each of two consecutive hours over the preceding 6 hours are collected for subsequent confirmation and determination processes as will be described below. Note that the 6 hours may be divided into three consecutive 2-hour blocks, or may be divided into five 2-hour blocks, each overlapped by 1 hour with the adjacent ones.

The length of the overlapping period can be set freely. The following describes an example where 6 hours are divided into five 2-hour blocks, each overlapped by 1 hour with the adjacent ones.

In step S92, CPU 110 calculates the total time the living activity levels have been within the range of 1 to 2 METs during the consecutive 2 hours, and if it is determined that the total time makes up 60% or more of the period, CPU 110 then recognizes the consecutive 2 hours as an active region. CPU 110 then determines whether or not such an active region appeared over the preceding 6 hours.

If no active regions have been found, [sleep processing mode 1] is terminated and CPU 110 switches the device back to [living activity measurement mode] (FIG. 8).

If any active region has been found, the process then proceeds to step S93.

In step S93, CPU 110 calculates the total time living activity levels have been kept at 1 MET during each of the two 2 consecutive hours flanking or partially overlapping the time period corresponding the active region. CPU 110 then determines whether or not there has been any period where the total time makes up 60% or more of the 2 consecutive hours (hereinafter this region is referred to as a "non-active region").

Absence of non-active regions during the period checked in step S93 means that there were no low-activity period, equivalent to sleep duration, either before or after the active region. CPU 110 then deems the active region as a time period where the user was "lounging and relaxing", not "sleeping", and then the process proceeds to step S94.

In step S94, CPU 110 checks not only the period checked in step S93 but also the period over the preceding 6 hours for the presence of an active region. If any active region has been found, CPU 110 then calculates the total time the active region appeared over the preceding 6 hours while considering the overlapping period described above, and extracts the total time as a lounging/relaxing duration.

In step S95, CPU 110 records in recording section 111 the patient's status that he/she was lounging/relaxing, the active region detected in step S92 and determination in step S93, and lounging/relaxing duration extracted in step S94, while correlating them with one another. Information about the status, living activity and duration can be used for subsequent analysis of the patient's sleep events.

After recording the status of "lounging/relaxing", CPU 110 switches the device from [sleep processing mode 1] to [living activity measurement mode] (FIG. 8).

When any non-active region has been found in the time period checked in step S93, the process proceeds to step S96. This means that the active region corresponded to the period where the patient was "sleeping."

In step S96, CPU 110 checks not only the period checked in step S93 but also the period over the preceding 6 hours for the presence of a non-active region. If any non-active region has been found, CPU 110 then calculates the total time the non-active region appeared over the preceding 6 hours while considering the overlapping period described above, and extracts the total time as a sleep duration.

In step S97, CPU 110 determines whether or not recording of blood glucose level was made during sleep, i.e., in the active region and the region detected in step S96.

If no records of blood glucose level was detected during sleep, in step S98, CPU 110 records in recording section 111 the patient's status that he/she was asleep, the active region detected in step S92 and determination in step S93, and sleep duration extracted in step S96, while correlating them with one another. Information about the status, living activity and duration can be used for subsequent analysis of the patient's sleep events.

After recording the status of "asleep", CPU 110 switches the device from [sleep processing mode 1] to [living activity measurement mode] (FIG. 8).

When recording of blood glucose level has been detected in step S97, in step S99, CPU 110 records in recording section 111 the fact that the 5-minute period before and after blood glucose measurement is active time, the active region detected in step S92 and determination in step S93, and during extracted in step S96, while correlating them with one another.

Thereafter, CPU 110 switches the device from [sleep processing mode 1] to [living activity measurement mode] (FIG. 8).

Figure 21:
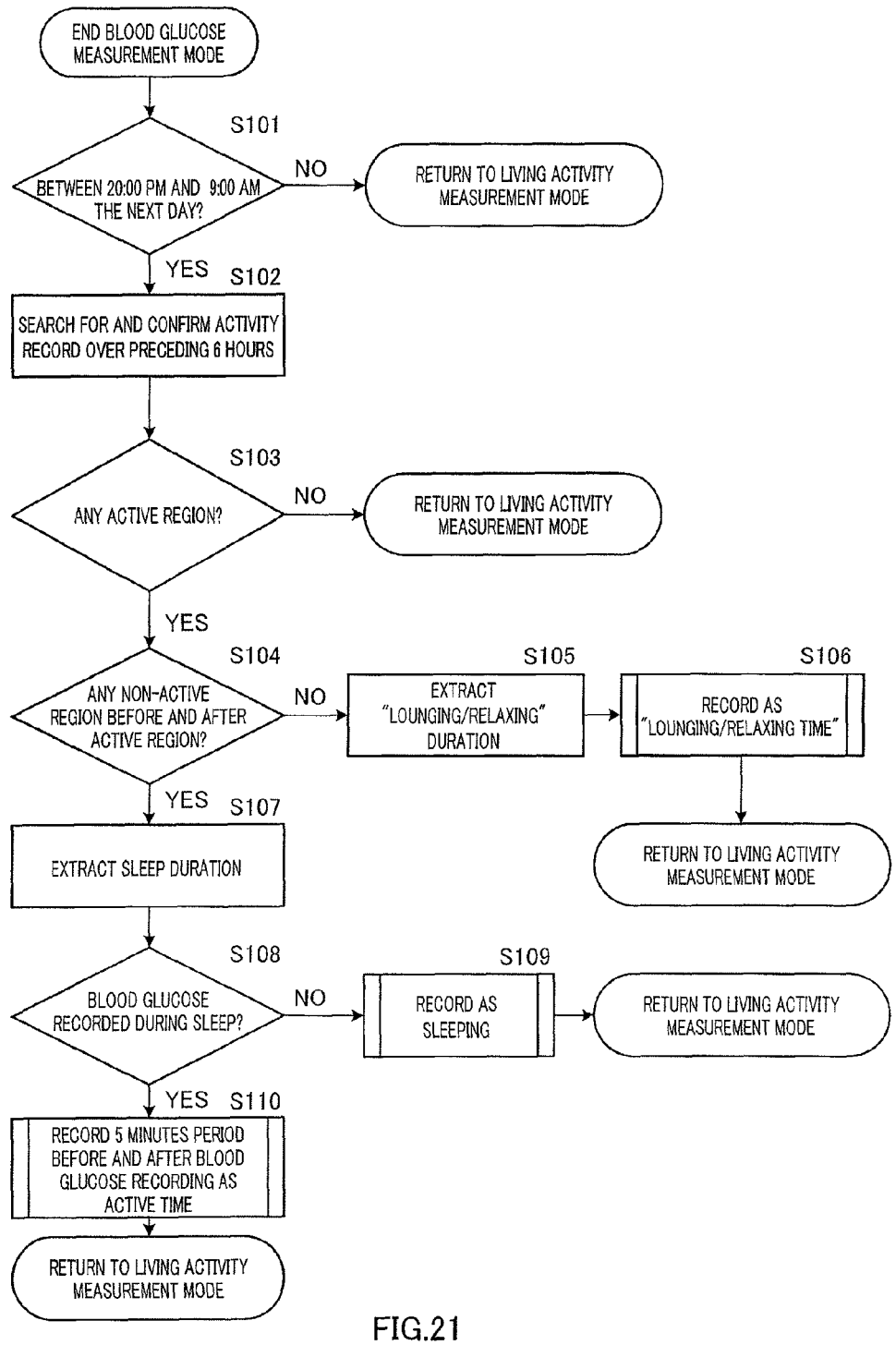
FIG. 21 is a flowchart of sleep processing mode 2 in a blood glucose measuring device according to Embodiment 3.

FIG. 21 is a flowchart of sleep processing mode 2 in blood glucose measuring device 100.

[Sleep processing mode 2] is activated by the completion of [blood glucose measurement mode 1] or [blood glucose measurement mode 2]. In step S101, CPU 110 checks clock data to determine whether or not the time zone is between 20:00 pm and 9:00 am the next day.

When the time zone is not between 20:00 pm and 9:00 am the next day, CPU switches the device from [sleep processing mode 2] to [living activity measurement mode] (FIG. 8).

When the time zone is between 20:00 pm and 9:00 am the next day, on the other hand, in step S102, CPU 110 searches recording section 111 for the living activity record over the preceding 6 hours. For example, CPU 110 retrieves a pattern of living activity level that shown in FIG. 13 over the preceding 3 hours. As in [sleep processing mode 1], CPU 110 then extracts the living activity level, followed by determination and confirmation processes.

In step S103, CPU 110 determines whether or not any active region has appeared over the preceding 6 hours as in step S92 of [sleep processing mode 1].

When no active region has been found, CPU switches the device from [sleep processing mode 2] to [living activity measurement mode] (FIG. 8).

When any active region has been found, on the other hand, the process proceeds to step S104.

As in step S93 of [sleep processing mode 1], in step S104, CPU 110 determines whether or not a non-active region has appeared in time regions flanking or partially overlapping the time period corresponding the active region detected in step S103.

Absence of non-active regions during the period checked in step S93 means that there were no low-activity period, equivalent to sleep duration, either before or after the active region. CPU 110 then deems the active region as a time period where the user was "lounging and relaxing", not "asleep", and then the process proceeds to step S105.

In step S105, CPU 110 checks not only the period checked in step S104 but also the period over the preceding 6 hours for the presence of an active region. If any active region has been found, CPU 110 then calculates the total time the active region appeared over the preceding 6 hours as in [sleep processing mode 1], and extracts the total time as a lounging/relaxing duration.

In step S106, CPU 110 records in recording section 111 the patient's status that he/she was lounging/relaxing, the active region detected in step S103 and determination in step S104, and lounging/relaxing duration extracted in step S105, while correlating them with one another. Information about the status, living activity and duration can be used for subsequent analysis of the patient's sleep events.

After recording the status of "lounging/relaxing", CPU 110 switches the device from [sleep processing mode 2] to [living activity measurement mode] (FIG. 8).

When any non-active region has been found in the time period checked in step S104, the process proceeds to step S107. This means that the active region corresponded to sleep duration.

In step S107, CPU 110 checks not only the period checked in step S104 but also the period over the preceding 6 hours for the presence of a non-active region. If any non-active region has been found, CPU 110 then calculates the total time the non-active region appeared over the preceding 6 hours as in [sleep processing mode 1], and extracts the total time as a sleep duration.

In step S108, CPU 110 determines whether or not recording of blood glucose level occurred during sleep, i.e., in the active region and the region detected in step S107.

If recording of blood glucose level was not detected during sleep, in step S109, CPU 110 records in recording section 111 the patient's status that he/she was asleep, the active region detected in step S103 and determination in step S104, and sleep duration extracted in step S107, while correlating them with one another. Information about the status, living activity and duration can be used for subsequent analysis of the patient's sleep events.

After recording the status of "asleep", CPU 110 switches the device from [sleep processing mode 2] to [living activity measurement mode] (FIG. 8).

When recording of blood glucose level has been detected in step S108, in step S110, CPU 110 records in recording section 111 the fact that the 5-minute period before and after blood glucose measurement is active time, the active region detected in step S103 and determination in step S104, and during extracted in step S107, while correlating them with one another.

Thereafter, CPU 110 switches the device from [sleep processing mode 2] to [living activity measurement mode] (FIG. 8).

As described above, in this embodiment, the exact sleep duration as well as sleep condition, which are clinically important, can be measured and recorded properly and accurately without bothering users. It is also made possible according to this embodiment to appropriately cope with the dawn phenomenon, an abnormal early-morning increase in blood glucose level frequently seen in severe diabetic patients, enabling for the first time blood glucose monitoring from many aspects, including sleeping. These achievements are expected to be highly meaningful for improving clinical outcomes by means of blood glucose monitoring.

Embodiment 4

Embodiment 4 describes another embodiment of living activity measurement mode.

The hardware configuration of a blood glucose measuring system according to Embodiment 4 of the present invention is identical to that illustrated in FIGS. 1 to 3.

[Living Activity Measurement Mode 2]

Figure 22:
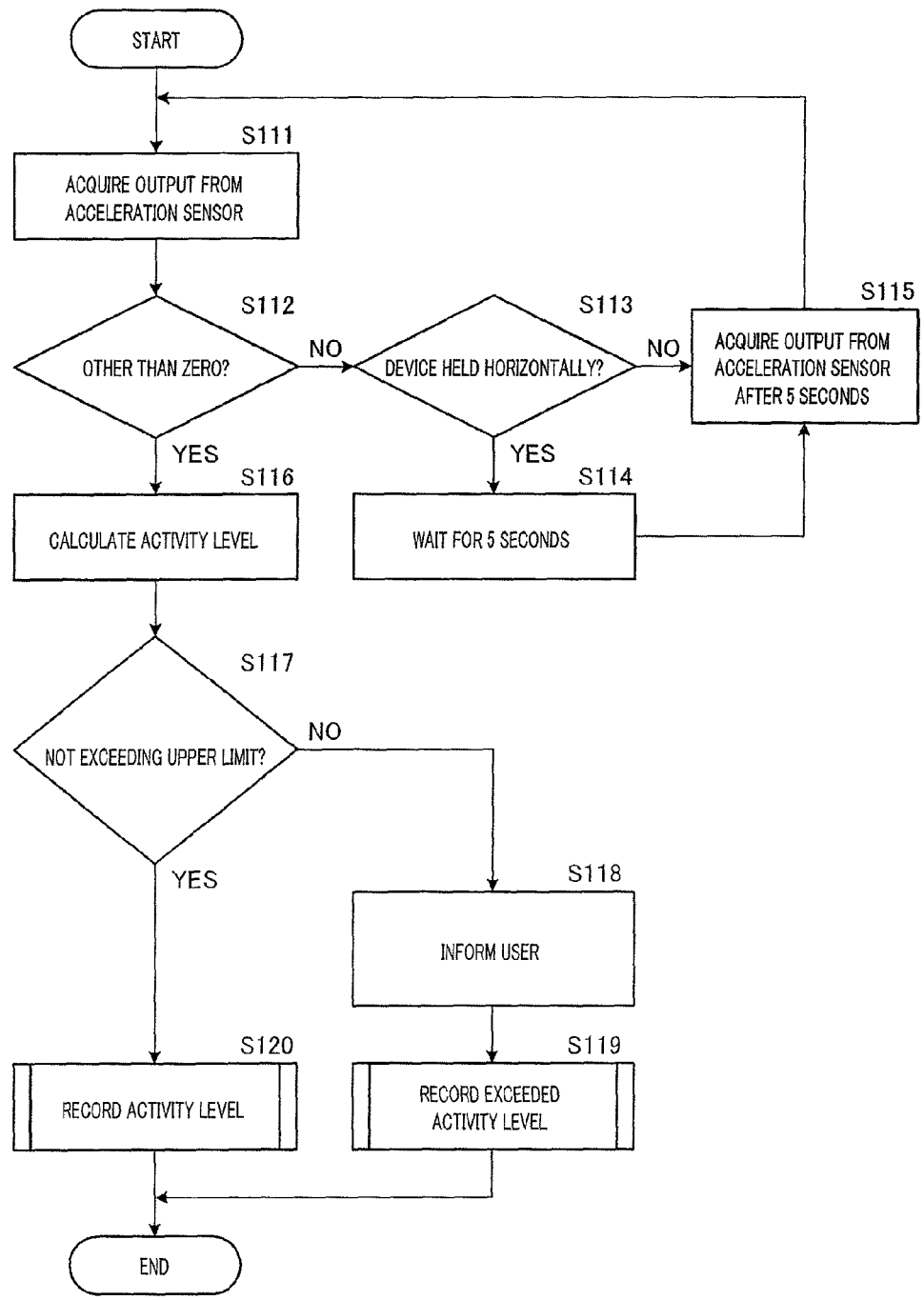
FIG. 22 is a flowchart of living activity measurement mode 2 in a blood glucose measuring device according to Embodiment 4.

FIG. 22 is a flowchart of living activity measurement mode 2 in blood glucose measuring device 100.

First, in step S111, CPU 110 acquires an output from acceleration sensor 112.

In step S112, CPU 110 determines whether or not the output from acceleration sensor 112 is other than zero.

When the output from acceleration sensor 112 is not other than zero, i.e., when acceleration sensor 112 detected motion, the process proceeds to step S113. Meanwhile, when the output from acceleration sensor 112 is other than zero, the process proceeds to step S116.

In step S113, CPU 110 determines whether or not the diabetes self-monitoring device (blood glucose measuring device 100) is held horizontally, based on the output from acceleration sensor 112. When CPU 110 has determined that the device is held horizontally, the process then proceeds to step S114 where the device waits for a predetermined time (e.g., 5 seconds) in a horizontal state, and then the process proceeds to step S115. When the device is not held horizontally, the process directly proceeds to step S115.

In step S115, CPU 110 waits for a predetermined time (e.g., 5 seconds) and then acquires an output from acceleration sensor 112, and the process returns to step S111. CPU 110 determines whether the diabetes self-monitoring device (blood glucose measuring device 100) is held horizontally. If it is determined that the device is held horizontally, CPU 110 waits for at least 5 seconds before acquiring an output from acceleration sensor 112. On the other hand, if the device is not held horizontally, CPU acquires the output 5 seconds after the determination. This is in order to obtain a proper output from acceleration sensor 112.

When the output from acceleration sensor 112 in step S112 is other than zero, in step S116, CPU 110 calculates activity level (living activity level) based on the output.

In step S117, CPU 110 determines whether or not the activity level is below the upper limit value input.

When the activity level exceeds the upper limit value previously set, CPU 110 notifies the user by beeping, displaying a message, flashing its icon, or any combinations of the above. Alternatively, a voice synthesizer LSI may be used to notify the user by voice.

In step 119, CPU 110 records in recording section 111 the exceed amount of living activity level, and then ends this flow.

On the other hand, when the activity level calculated in step S117 is below the upper limit, in step S120, CPU 110 records the calculated value in recording section 111 and ends this flow.

Step S112 for detecting the orientation of blood glucose measuring device 100 with respect to horizontal is one embodiment of [A. high-precision measurement control].

Next will describe [living activity restriction mode].

[Living Activity Restriction Mode]

Figure 23:
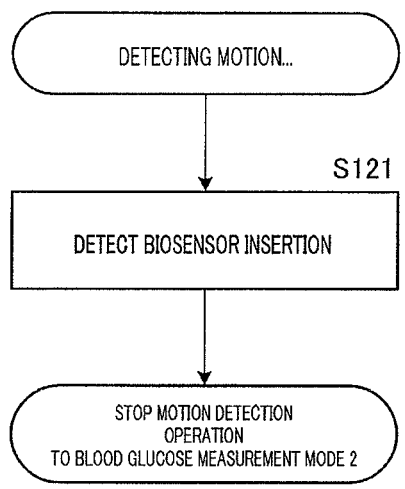
FIG. 23 is a flowchart of living activity restriction mode in a blood glucose measuring device according to Embodiment 4.

FIG. 23 is a flowchart of living activity restriction mode in blood glucose measuring device 100.

Living activity restriction mode illustrated in FIG. 23 is activated during a motion measurement operation. In step S121, CPU 110 detects the insertion of a biosensor (blood glucose sensor 200) into sensor attachment 101 of blood glucose measuring device 100. When blood glucose sensor 200 is inserted to reach a defined portion, the motion measurement operation is stopped, and the device switches to [blood glucose measurement mode 2] (FIG. 12).

In this way, according to this embodiment, it is possible not only to bring about the effect of Embodiment 1, but to caution the user that the living activity level has exceeded the upper limit.

Embodiment 5

The diabetes self-monitoring devices (blood glucose measuring devices 100) according to Embodiments 1 to 4 have enabled accurate blood glucose management based on living activity, by combining the blood glucose levels measured by the biosensor (blood glucose sensor 200) with the amounts of living activity detected by motion measurement section (acceleration sensor) 112.

Embodiment 5 describes an effective method of using the blood glucose measuring systems having the excellent features described above.

Figure 24:
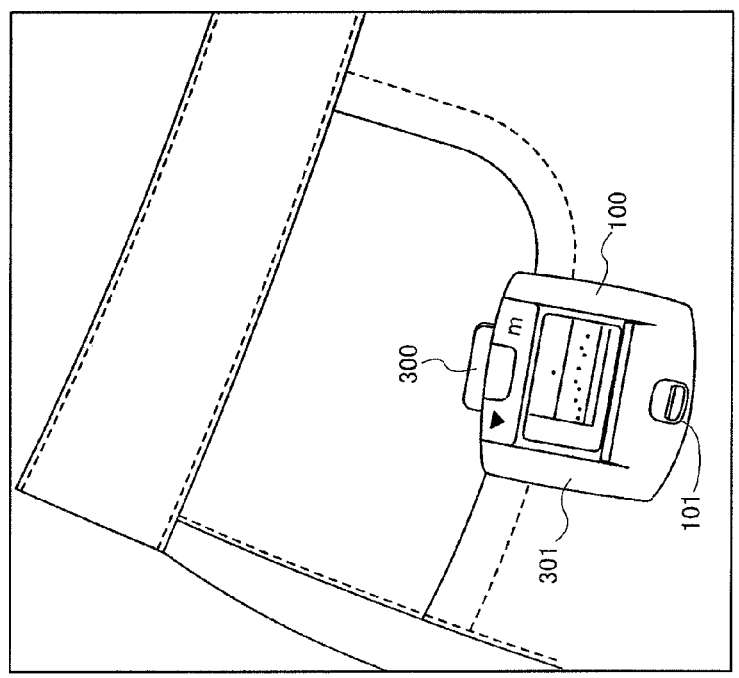
FIG. 24 illustrates an example of how a blood glucose measuring device according to Embodiment 5 is used.

FIG. 24 illustrates an example of how blood glucose measuring device 100 is used, illustrating an example where the device is attached to a pocket of a jeans.

As illustrated in FIG. 24, attachment unit 300 is attached onto pocket 301 of a jeans, and blood glucose measuring device 100 is coupled to attachment unit 300.

The joint between attachment unit 300 and blood glucose measuring device 100 freely rotates about one axis. With this configuration, the user can confirm the display by rotating the joint without having to remove attachment unit 300 from pocket 301. The joint may also be so configured as to rotate about two or three axes.

In FIG. 24, blood glucose measuring device 100 is made water repellent, as it is an electric device and exposed to the outside. It is also possible to provide means of notifying the occurrence of water wetting; to protect blood glucose measuring device 100 by providing a cover for the display section and other operation keys; and/or to equip the device with the display section facing the body side so as to hide the display from others.

Although blood glucose measuring device 100 is shown attached onto pocket 301 of a jeans in FIG. 24, it can be attached in any form to any article that can achieve an equivalent effect, including waist belt, underclothes, clothes, clothes pockets, shoes and hats or caps; accessories such as necklace and bracelet; and articles that are usually carried or worn, such as pen and wristwatch.

Figure 25:
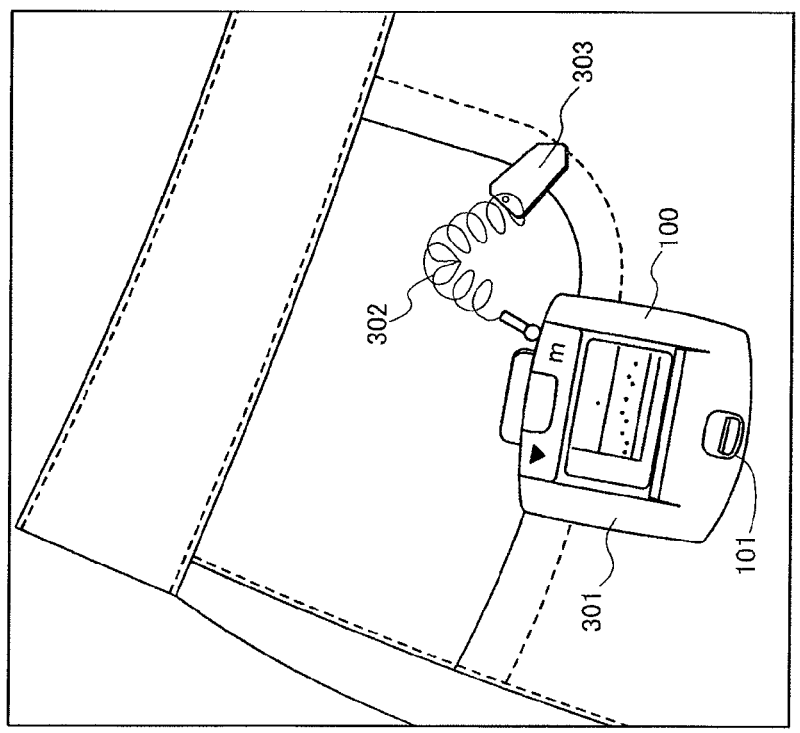
FIG. 25 illustrates another example of how a blood glucose measuring device according to Embodiment 5 is used.

FIG. 25 illustrates another example of how blood glucose measuring device 100 is used, illustrating an example where a strap clip is attached to the device.

As illustrated in FIG. 25, blood glucose measuring device 100 includes strap clip 302 and mini-clip 303.

Strap clip 302 prevents blood glucose measuring device 100 from being accidentally detached from the attachment section in cases where, for example, the user arm collides with the device. Strap clip 302 is connected to blood glucose measuring device on one end, and to mini clip 303 on the other end, which clip is attached to the rim of jeans pocket 301. When the blood glucose measuring system is not used, the user releases mini clip 303 to remove the entire system from the body.

Strap clip 302 can be attached to and detached from blood glucose measuring device 100, and the stripe of strap clip 302 is preferably formed as an extendable helix stripe. Strap clip 302 is directly to blood glucose measuring device 100 and to mini clip 302. Thus, even when measurement is made with the system separated from strap clip 302, strap clip 302 remains connected to mini clip 302. It is thus possible to improve handleability by preventing the strap from falling.

Figure 26:
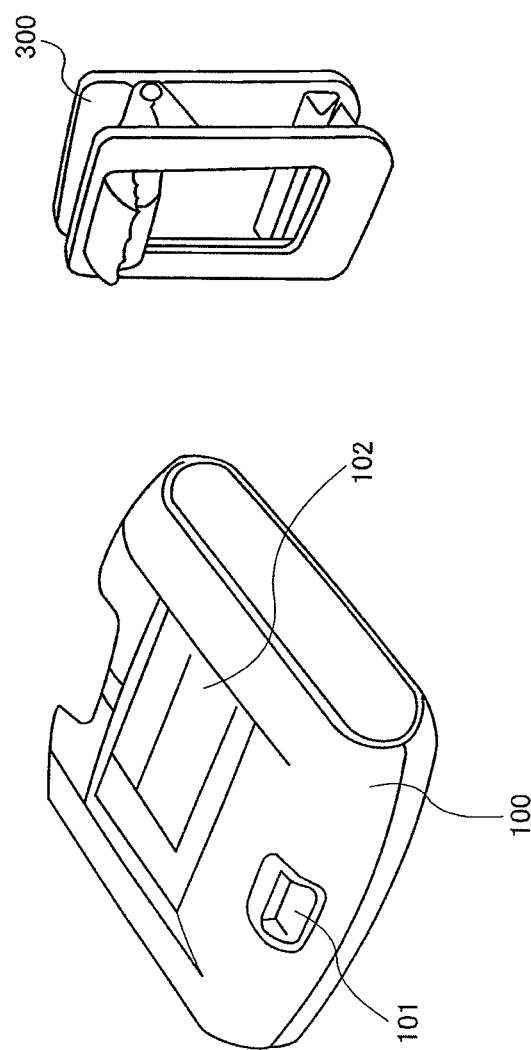
FIG. 26 illustrates another example of how a blood glucose measuring device according to Embodiment 5 is used.

FIG. 26 illustrates another example of how blood glucose measuring device 100 is used, illustrating an example where attachment unit 300 is used while being separated from blood glucose measuring device 100. As illustrated in FIG. 26, attachment unit 300 is removed from clothes or the like, and blood glucose measuring device 100 and attachment unit 300 are separated from each other.

Figure 27:
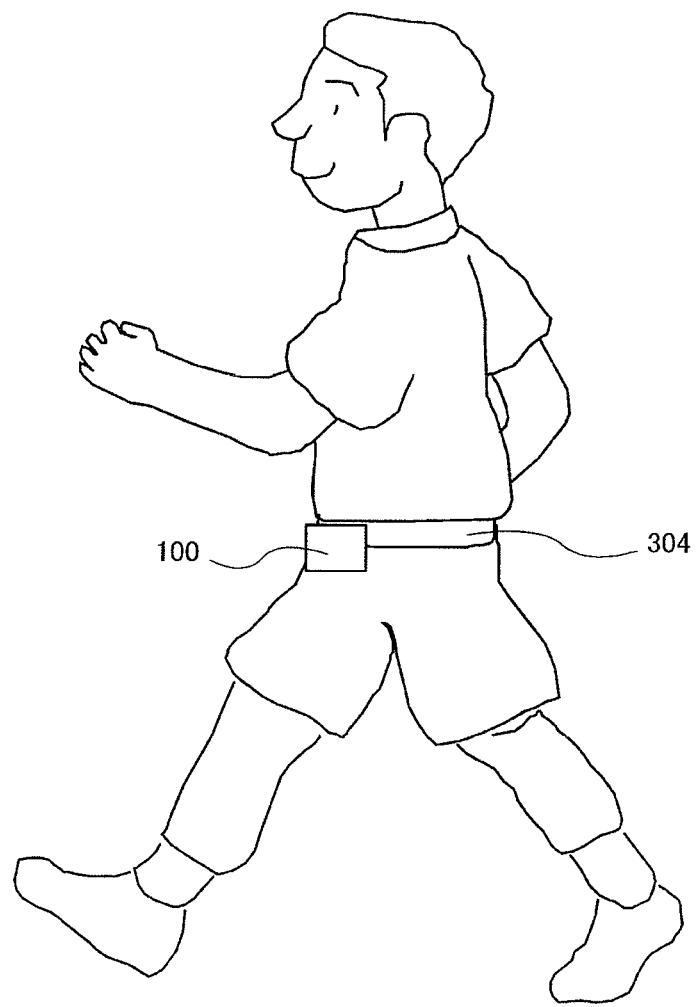
FIG. 27 illustrates another example of how a blood glucose measuring device according to Embodiment 5 is used.

FIG. 27 illustrates another example of how blood glucose measuring device 100 is used, showing a conceptual illustration how blood glucose measuring device 100 is worn just below the waist. As illustrated in FIG. 27, blood glucose measuring device 100 is attached to belt 304. Because the device measures blood glucose levels as well as the amounts of living activity, it is preferable to wear the device at just below the waist as in FIG. 24 where it is attached to jeans pocket 301. However, a person having ordinary skill in the art can freely choice the shape, size, dimension, attachment position, etc., depending on the intended purpose.

It is also possible to put the device into a dedicated pocket or the like. Moreover, where the user wishes to carry the device privately, it can be worn over underclothes or at any site invisible from the outside. Further, in order to avoid possible contact with hands or arms during daily activities, the device is preferably worn such that the top side of blood glucose measuring device 100 is positioned below the upper end of the pants or belt around the waist.

Embodiment 6

Figure 28:
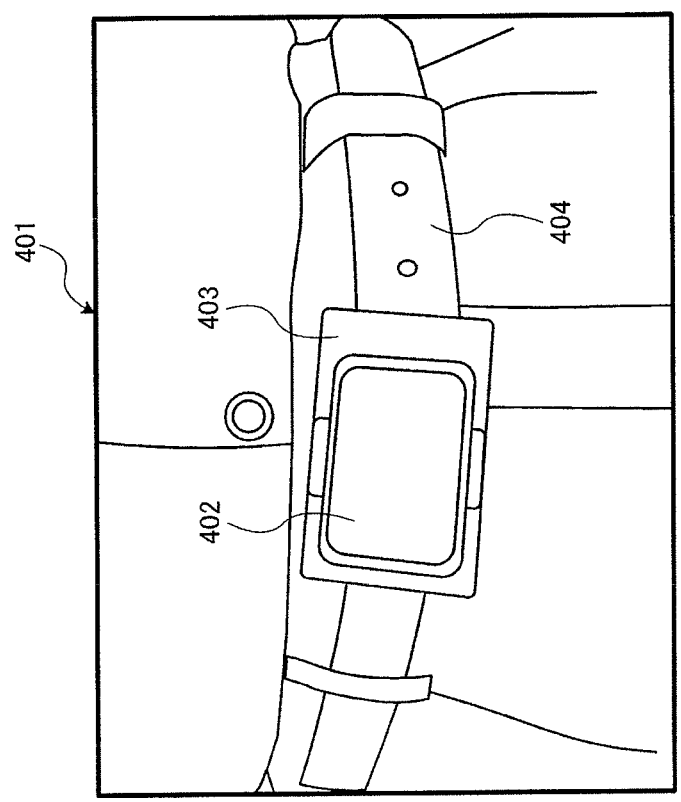
FIG. 28 is an overview illustration of a blood glucose measuring device according to Embodiment 6.

FIG. 28 is an overview illustration of a blood glucose measuring device according to Embodiment 6. This embodiment is directed to an example where the blood glucose measuring system is applied to a blood glucose measuring device-incorporated belt.

As illustrated in FIG. 28, blood glucose measuring system 401 is composed of blood glucose measuring device 402, belt buckle 403 equipped with blood glucose measuring device 402, and belt 404 having belt buckle 403.

Blood glucose measuring device 402 has the same function as blood glucose measuring device 100 illustrated in FIGS. 1 and 2.

Figure 29:
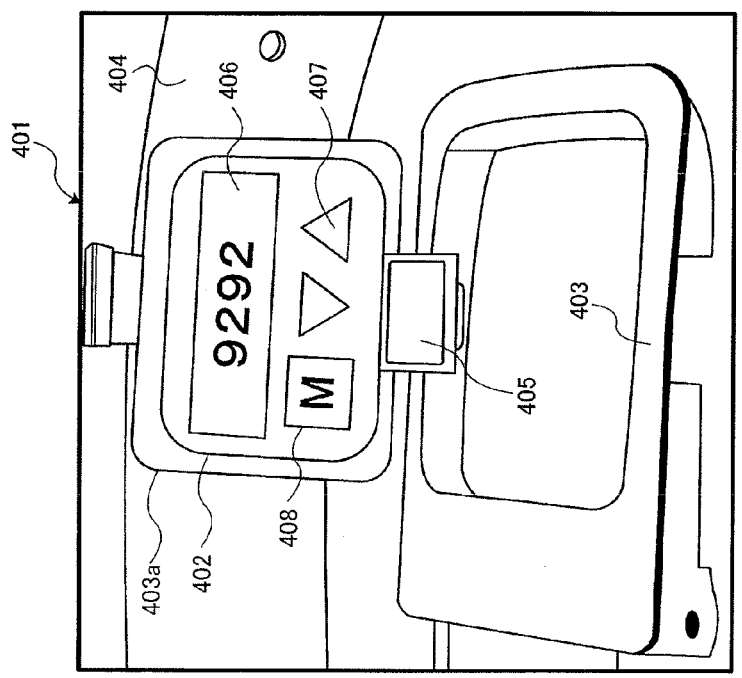
FIG. 29 illustrates a blood glucose measuring device according to Embodiment 6, with the belt buckle opened up to show the display section.

FIG. 29 illustrates a blood glucose measuring device, with the belt buckle opened up so that the user can see the display section.

As illustrated in FIG. 29, blood glucose measuring device 402 includes sensor attachment 403*a* incorporated into belt buckle 403, hinge 405, display section 406, operation keys 407, and memory & decision key 408.

To sensor attachment 403*a*, blood glucose sensor 200 illustrated in FIGS. 1 and 2 can be attached.

Hinge 405 pivotably supports blood glucose measuring device 402 and belt buckle 403.

Display section 406 is composed of LCD or the like and displays a measurement history and the like. In FIG. 29, display section 406 indicates the measured living activity level.

In the drawing, operation keys 407 are illustrated as arrow keys; the user inputs a command to software programs by using the operations keys and memory & decision key 408.

Memory & decision key 408 causes display section 406 to display a measurement history and the like in response to a user command. The user inputs a command to software programs with memory & decision key 408 and operation keys 407.

Blood glucose measuring device 402 is incorporated into belt buckle 403. Blood glucose measuring system 401 includes belt 404 in which blood glucose measuring device 402 is attached to belt buckle 403. This configuration prevents users from forgetting to attach blood glucose measuring device 402. Moreover, as blood glucose measuring device 402 is already mounted to belt buckle 403, there is no need to wear the device in a pockets or the like, thereby avoiding bothersome operations.

Figure 30:
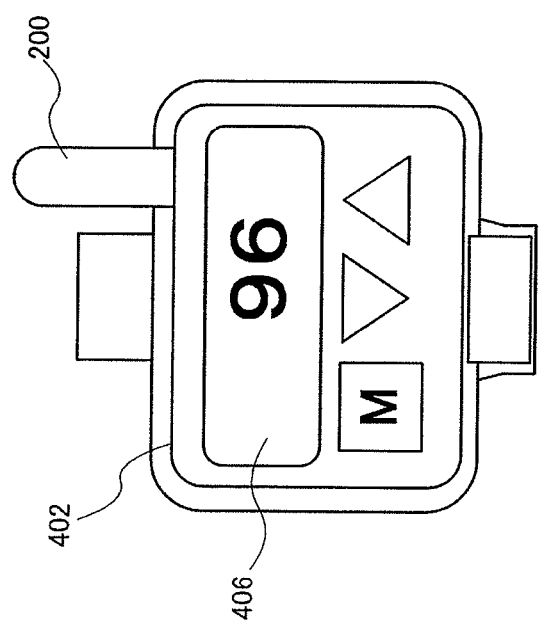
FIG. 30 illustrates a blood glucose measuring device according to Embodiment 6 in a state where it is detached from the belt buckle.

FIG. 30 illustrates blood glucose measuring device 402 detached from belt buckle 403.

In FIG. 30, display section 406 displays a blood glucose level measured with blood glucose sensor 200.

As illustrated in FIG. 30, blood glucose measurements are made with blood glucose sensor 200 attached to blood glucose measuring device 402. Because blood glucose measuring device 402 includes therein an acceleration sensor and/or an angular speed sensor as does blood glucose measuring device 100 illustrated in FIGS. 1 and 2, the data displayed on display section 406 is preferably inverted so that the user can easily confirm the measured value. The advantage of inverting the display also applies to Embodiment 5 wherein a clip is used for attachment.

Embodiment 7

Embodiment 7 describes a CGM sensor unit. Blood glucose measuring devices 100 according to Embodiments 1 to 6 use as a biosensor blood glucose sensor 200. On the other hand, Embodiment 7 employs a continuous glucose monitoring (CGM) sensor unit that measures a CGM value using as a biosensor a CGM sensor inserted under the skin.

With this sensor system difference, the CGM sensor unit is small, light, and thin when compared to blood glucose measuring devices 100 according to Embodiments 1 to 6.

Figure 31:
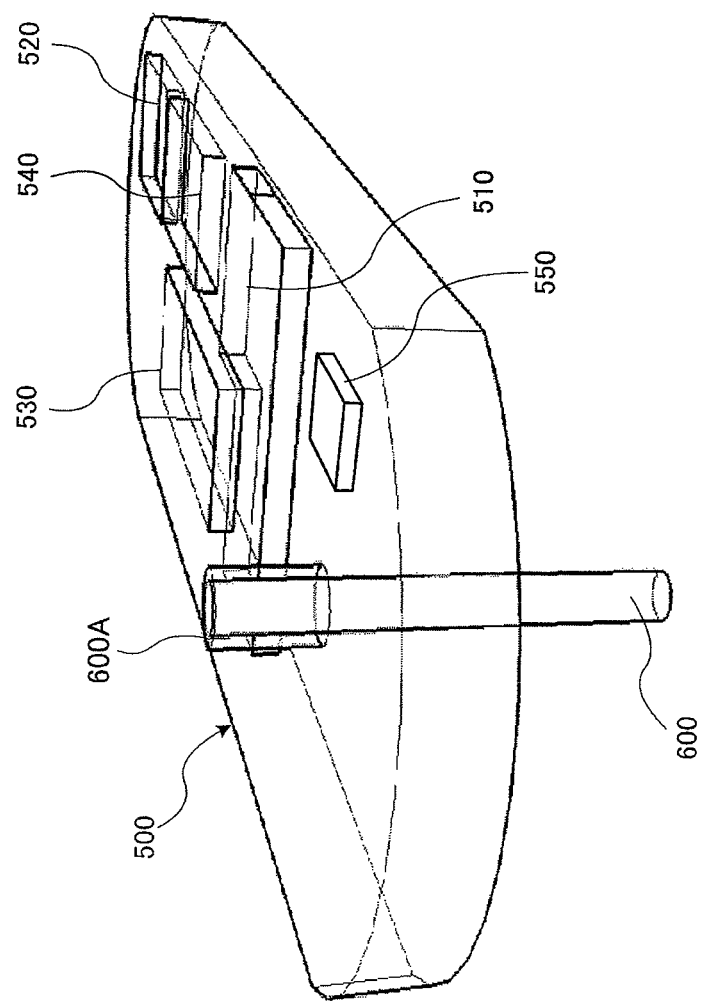
FIG. 31 is an overview illustration of a CGM sensor unit according to Embodiment 7.

FIG. 31 is an overview illustration of a CGM sensor unit according to Embodiment 7 of the present invention. This embodiment is directed to an example where a blood glucose measuring system is applied to a CGM sensor unit.

As illustrated in FIG. 31, CGM sensor unit 500 includes CGM sensor unit circuit section 510, living activity measurement section 520, communication section 530, power supply 540, temperature measurement section 550, and CGM sensor connector 600A.

CGM sensor 600 is inserted under the skin and continuously measures glucose levels in the interstitial fluid. CGM sensor 600 has a reagent such as enzyme immobilized thereon. CGM sensor 600 is connected to CGM sensor unit circuit section 510 via CGM sensor connector 600A. The detailed structure of CGM sensor 600 will be described later with reference to FIGS. 32A to 32C.

Other than the function regarding the CGM detection system, CGM sensor unit circuit section 510 executes the same control operation as that of blood glucose measuring device 100 illustrated in FIGS. 1 and 2 with regard to the measurement of the amount of human living activity, Specifically, CGM sensor unit circuit section 510 controls the operation of each section and records in recording section 111 (FIG. 2) CGM values, glucose levels in the interstitial fluid, which are measured by CGM sensor 600, and motion information measured by living activity measurement section 520, while correlating them with one another. CGM sensor unit circuit section 510 controls transmission of the CGM values, which have been associated with the motion information and stored in recording section 111 (FIG. 2), to blood glucose measuring device 200 (FIG. 2) via communication section 530.

Living activity measurement section 520 conducts the same living activity measurements as motion measurement section (acceleration sensor) 112 illustrated in FIGS. 1 and 2. It should be noted that living activity measurement section 520 outputs the move amount of CGM sensor unit 500.

Communication section 530 is dedicated or general communication means and is either wireless or wired. For the communication method, a wireless communication system such as specified near-field wireless communication, Bluetooth®, Ultra Wideband (UWB), or RF communication can be used. Specified near-field wireless communication, Bluetooth®, Ultra Wideband (UWB) are also referred to as low-power near-field bilateral wireless communication systems.

Temperature measurement section 550 measures and outputs body temperature. CPU 110 records in recording section 111 the temperature measured by temperature measurement section 550 while correlating it with blood glucose level and living activity level.

As CGM sensor unit 500 is placed directly on the skin, more precise living activity measurement is possible. CGM sensor unit 500 preferably has a temperature measuring function. Temperature measurement not only prevents the CGM sensor from generating abnormal values, but also enables body temperature monitoring as a vital sign.

CGM sensor unit 500 is small, light, and thin when compared with blood glucose measuring device 100 illustrated in FIG. 1. There are no particular limitations to the size and shape of CGM sensor unit 500; it is preferably small enough (e.g., coin size) that the subject does not feel discomfort even when carrying the device all the time. CGM sensor unit 500 is attached to the subject's body like CGM insulin pump unit 800 illustrated in FIG. 38 to be described later.

CGM sensor unit 500 is attached to the subject's body during use. For this reason, CGM sensor unit 500 needs to be as small, light and this as possible.

In this embodiment, CGM sensor unit circuit section 510, which also serves as analyte measuring means and sleep duration detection means, is equivalent to blood glucose measuring device illustrated in FIG. 2 in which display section 102, operation keys 103 and memory & decision key 104 are disposed of.

Blood glucose measurement circuit 113 of blood glucose measuring device 100 illustrated in FIG. 2 is incorporated into CGM sensor unit circuit section 510, and the corresponding circuit of CGM sensor unit circuit section 510 measures a CGMS value instead of blood glucose. CGM sensor unit circuit section 510 includes communication section 530 instead of computer interface 116 of blood glucose measuring device 100 illustrated in FIG. 2.

CGM sensor unit 500 and blood glucose measuring device 100 (FIGS. 1 and 2) are basically identical in structure except for the differences described above. Specifically, CGM sensor unit 500 and blood glucose measuring device 100 both include a motion measurement section that measures motions of physical activities (corresponding to living activity measurement section 520 for CGM sensor unit 500, and motion measurement section 112 for blood glucose measuring device 100), and recording section 111 (FIG. 2) for recording motion information and measured value of blood glucose level or CGM while associating motion information and measured value with each other.

In other words, any desired configuration may be employed for the measuring device according to this embodiment as long as it includes a motion measurement section that measures motions of physical activities, and a recording section that records the motion information and the value measured by the motion measurement section into a memory while associating the motion information and measured value with each other.

Figure 32:
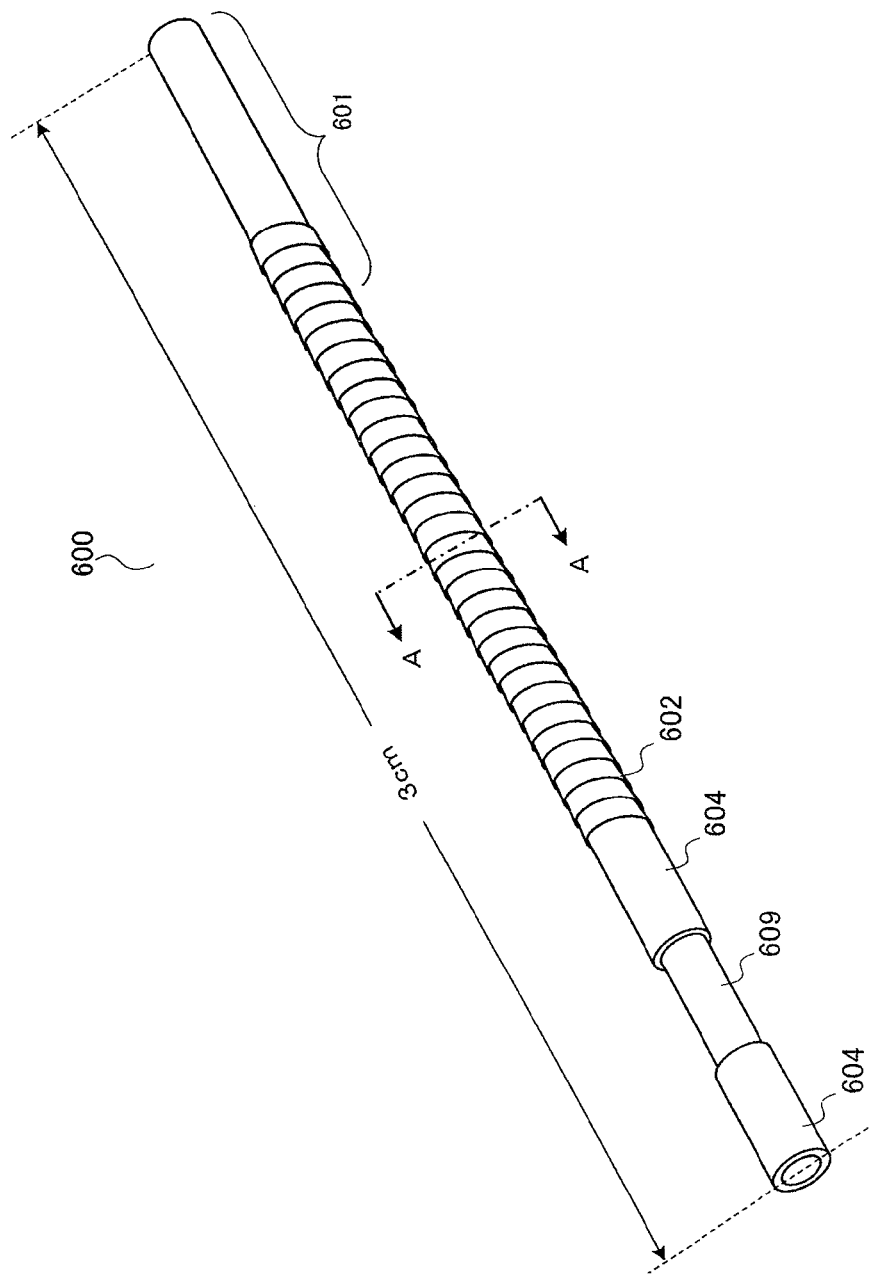
FIG. 32A is a perspective view illustrating the detail structure of a CGM sensor of a CGM sensor unit according to Embodiment 7.
FIG. 32B is a sectional view of FIG. 32A taken along A-A line.
FIG. 32C illustrates an example of dimensions of a CGM sensor of a CGM sensor unit according to Embodiment 7.
Figure 32C:
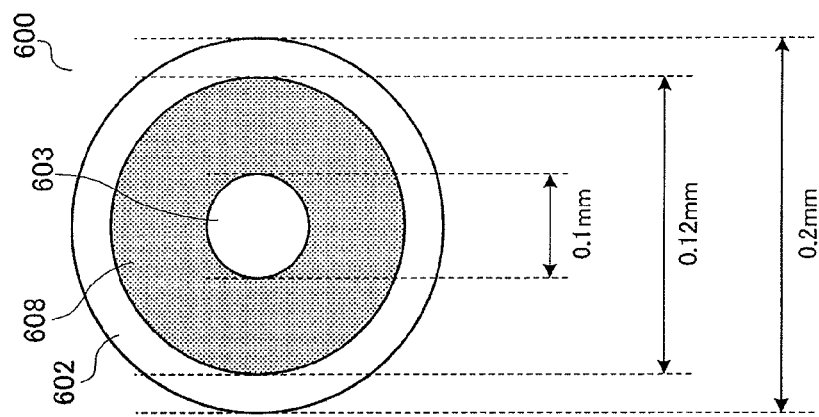
Figure 32B:
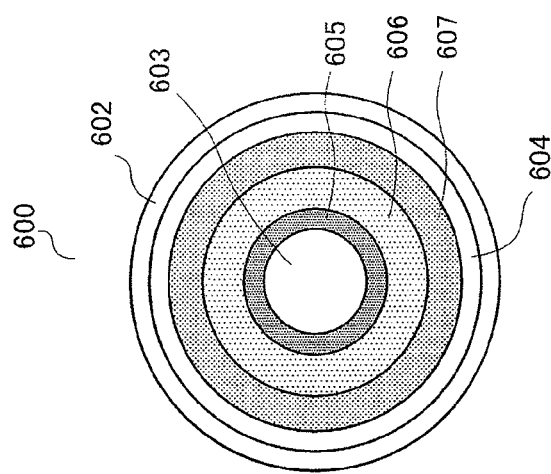

FIG. 32A is a perspective view illustrating the detail structure of CGM sensor 600, FIG. 32B is a sectional view of FIG. 32A taken along A-A line, and FIG. 32C illustrates an example of dimensions of CGM sensor 600. Note in FIG. 32A that the tip of CGM sensor 600 is partially disassembled for explaining the internal structure of the sensor.

As illustrated in FIGS. 32A and 32B, CGM sensor 600 includes connector connection section 601, counter/reference electrode 602, working electrode 603, hydrophilic polymer 605, immobilized enzyme film 606, semipermeable film 607, and insulator 604.

Herein, in CGM sensor 600, a layer formed of hydrophilic polymer 605, immobilized enzyme film 606, semipermeable film 607 and insulator 604 is referred to as insulating layer 608 (see FIG. 32C). Further, a portion of CGM sensor 600 around which counter/reference electrode 602 is not wound and in which semipermeable film 607 is exposed by peeling insulator 604 from insulating layer 608 such that interstitial fluid infiltrates toward working electrode 603 is referred to as sensing part 609.

Although insulating layer 608 has been illustrated as being formed of hydrophilic polymer 605, immobilized enzyme film 606, semipermeable film 607 and insulator 604 in this embodiment, there are no particular limitations to the components of insulating layer 608.

As illustrated in FIG. 32C, CGM sensor 600 is circular in section, and counter/reference electrode 602, insulating layer 608 and working electrode 603 have an outer dimension of 0.2 mm, 0.12 mm and 0.1 mm in diameter, respectively. Note that the circular sectional shape and the outer dimensions are for example purposes only; for example, the outer diameter of the needle-type biosensor in FIG. 35a described later is some 26 gauge (0.4572 mm) to 21 gauge (0.8121 mm) in diameter.

Connector connection section 601 is connected to CGM sensor connector 600A of CGM sensor unit 500 (FIG. 31).

CGM sensor 600 is inserted under the skin and measures glucose levels in an environment surrounded by adipocytes and filled with the interstitial fluid. Proteins are removed from the interstitial fluid by semipermeable film 607 when the fluid infiltrates CGM sensor 600 at sensing part 609. Glucose oxidase of immobilized enzyme film 606 catalyses the following reaction in the interstitial fluid from which proteins have been removed.

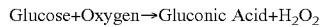

Glucose+Oxygen→Gluconic Acid+$H_2O_2$

Working electrode 603 electrically detects $H_2O_2$, hydrogen peroxide, produced by the above reaction.

CGM sensor 600 is a biosensor that detects glucose levels in blood or interstitial fluid, as does blood glucose sensor 200 according to Embodiments 1 to 5. CGM sensor 600 is inserted under the skin of a subject for continuous measurement of continuous glucose monitoring (CGM) values. Thus, CGM sensor unit 500 (FIG. 31) provided with CGM sensor 600 is directly attached onto the subject's skin.

Living activity measurement section 520 (e.g., acceleration sensor 112) incorporated into CGM sensor unit 500 also detects subject's motions over the skin, i.e., physical motions of the subject. Namely, living activity measurement section 520 measures motions of the subject in which CGM sensor 600 is inserted in the skin, as motions of the patient's physical activities.

Next will describe operations of the CGM sensor described above.

First, CGMS living activity measurement mode will be described.

[CGMS Living Activity Measurement Mode]

Figure 33:
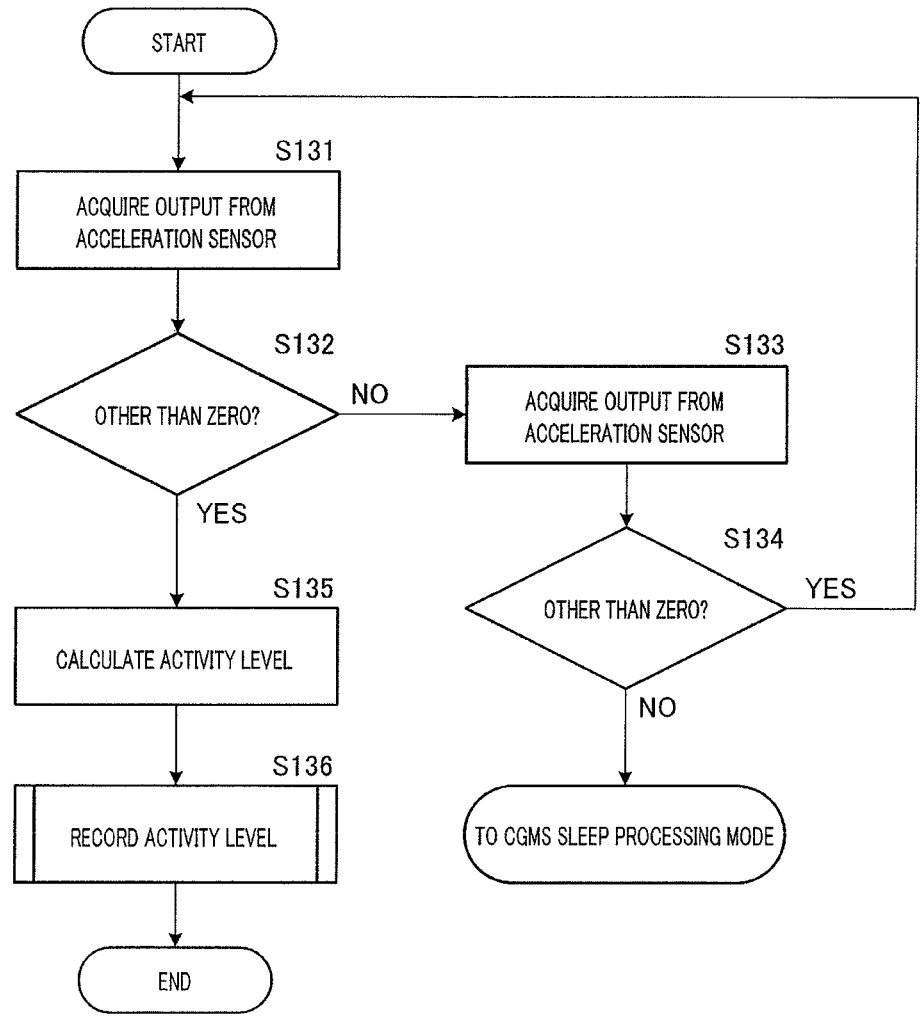
FIG. 33 is a flowchart of CGMS living activity measurement mode in a CGM sensor unit of a CGM sensor unit according to Embodiment 7.

FIG. 33 is a flowchart of CGMS living activity measurement mode in CGM sensor unit 500. This flow is repeatedly executed by CPU 110 (FIG. 2) in CGM sensor unit circuit section 510 at predetermined timings.

With regard to living activity measurement processing, CPU 110 performs the same processing as CPU 110 of blood glucose measuring device illustrated in FIGS. 1 and 2. Namely, other than the function regarding the CGM detection system, CGM sensor unit circuit section 510 has the same control operation as that of blood glucose measuring device 100 illustrated in FIGS. 1 and 2.

However, CGM sensor unit 500 is characterized in that CGM sensor 600 is inserted under the skin for continuous measurement of CGM values, and that living activity measurement section 520 housed in CGM sensor unit 500 measures physical motions of a subject all the time.

For living activity measurement 520, motion measurement section (acceleration sensor) 112 illustrated in FIGS. 1 and 2 is exemplified. Instead of acceleration sensor 112, an angular speed sensor, a vibration sensor or the like may be used. Acceleration sensor 112 outputs the movement amount of the CGM sensor unit.

First, in step S131, CPU 110 acquires an output from acceleration sensor 112.

In step S132, CPU 110 determines whether or not the output from acceleration sensor 112 is other than zero.

When it has been determined that the output from acceleration sensor 112 is zero, i.e., when acceleration sensor 112 has not detected any movement, the process proceeds to step S133. On the other hand, when the output from acceleration sensor 112 is other than zero, the process proceeds to step S135.

In step S133, CPU 110 again acquires an output from acceleration sensor 112 after a predetermined time (e.g., 3 minutes).

In step S134, CPU 110 determines whether or not the output from acceleration sensor 112 is other than zero. When the output is other than zero, the process proceeds back to step S131.

Figure 34:
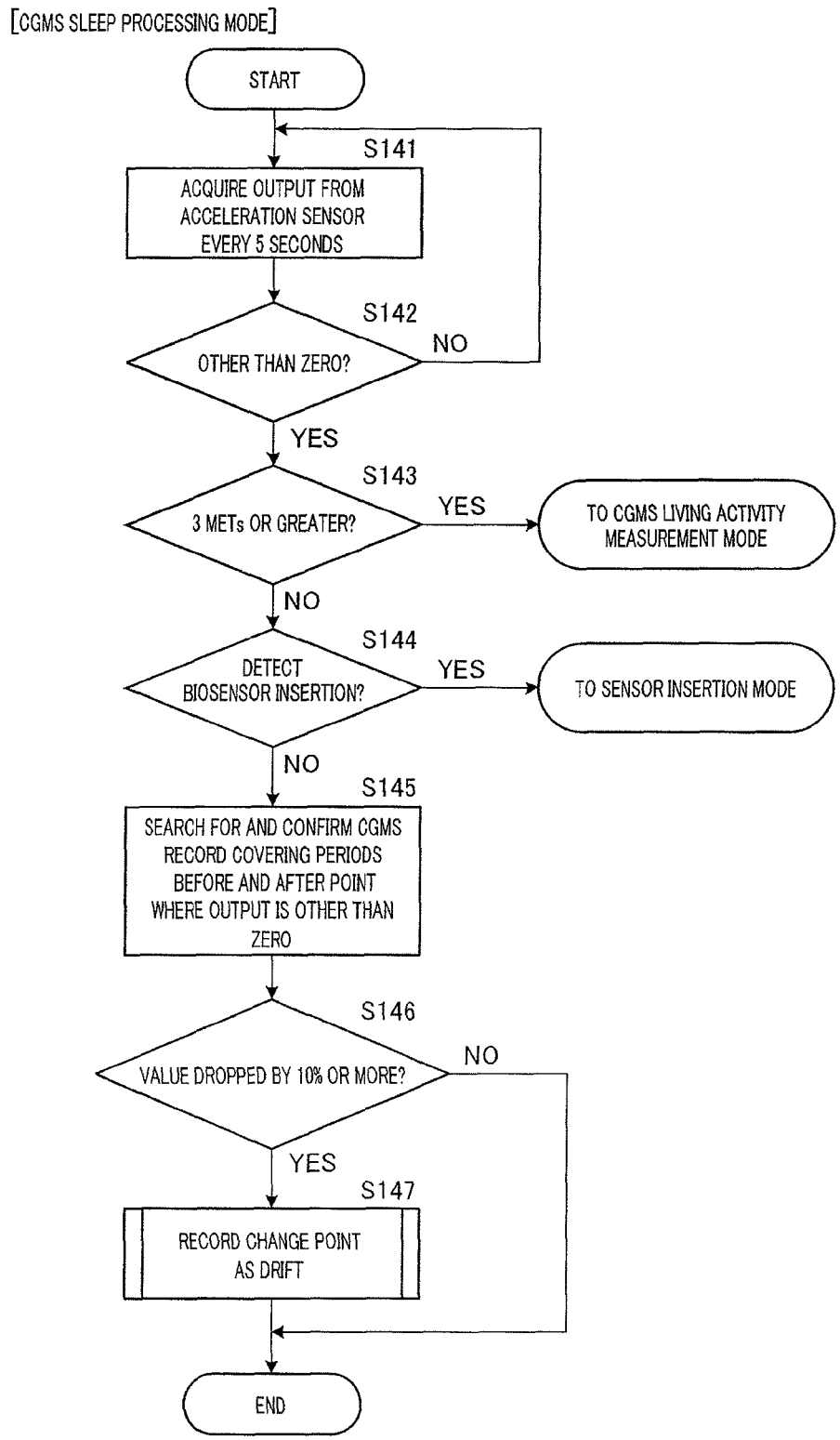
FIG. 34 is a flowchart of CGMS sleep processing mode in a CGM sensor unit according to Embodiment 7.

When it is determined in step S134 that the output from acceleration sensor 112 is zero, CPU 110 then determines that the subject's body is not moving, because the two outputs of acceleration sensor 112, received at a predetermined interval, are both zero, and switches the device to [CGMS sleep processing mode] (FIG. 34).

On the other hand, when it is determined in step S132 that the output from acceleration sensor 112 is other than zero, in step S135, CPU calculates activity level (living activity level) based on the output from acceleration sensor 112.

In step S136, CPU 110 records the calculated activity level in recording section 112 (FIG. 2) and ends this flow.

Although this embodiment has described an example where CGM sensor unit circuit section (FIG. 31) calculates the living activity level based on the output from acceleration sensor 112, it is only necessary that CGM sensor unit 500 record in recording section 111 (FIG. 2) the motion information of physical activities and CGM values measured by CGM sensor 660, while associating the motion information and CGM values with each other.

For example, CGM sensor unit 500 records in recording section 111 (FIG. 2) the motion information of physical activities and CGM values measured by CGM sensor 660, while associating the motion information and CGM values with each other. At any appropriate timing, CGM sensor unit circuit section 510 (FIG. 31) calculates the living activity level based on the measured value which has been associated with the motion information and recorded in recording section 111 (FIG. 2). At this time, CGMS sleep processing mode (later described) may be executed.

Namely, calculation of living amount level is effected at any timing as long as CGM sensor unit 500 records in recording section 111 (FIG. 2) the motion information of physical activities and CGM values measured by CGM sensor 600 while associating them with each other.

Further, CGM sensor unit 500 may conduct calculation of living activity level on blood glucose measuring device 100 (FIGS. 1 and 2) side. In this case, CGM sensor unit 500 transfers the measured value, which has been associated with motion information and recorded in recording section 111 (FIG. 2), to computer interface 116 (FIGS. 1 and 2) of blood glucose measuring device 100 via communication section 530 (FIG. 31).

Next will describe CGMS sleep processing mode.

CGM sensor unit 500 needs to consider drifts that occur upon CGMS measurements during sleep. [CGMS sleep processing mode] records drifts.

[CGMS Sleep Processing Mode]

FIG. 34 is a flowchart of CGMS sleep processing mode in CGM sensor unit 500. This mode is switched from [CGMS living activity measurement mode] when it is determined that the output from acceleration sensor 112 in step S134 of FIG. 33 is not other than zero.

In step S141, CPU 110 acquires an output from acceleration sensor 112 at every predetermined interval (5 seconds herein).

In step S142, CPU 110 sequentially determines whether or not the output from acceleration sensor 112 acquired is other than zero, and waits until the output from acceleration sensor 112 becomes other than zero by returning to step S141.

When the output from acceleration sensor 112 is other than zero, in step S143, CPU 110 determines whether or not the living activity level calculated based on the output from acceleration sensor 112 is 3 METs or greater.

When the living activity level is 3 METs or greater, the device switches to [CGMS living activity measurement mode] (FIG. 33).

On the other hand, when the living activity level calculated in step S143 is less than 3 METs, in step S144, CPU 110 determines whether or not biosensor 200 has been inserted.

When biosensor 200 has been inserted, the device switches to sensor insertion mode (not illustrated), which determines whether or not biosensor 200 has been put in place.

When no insertion of biosensor 200 has been detected, in S145, CPU 110 searches for and confirms a CGMS record that covers periods before and after the point at which the output from acceleration sensor 112 is other than zero.

In step S146, CPU 110 determines whether or not the CGMS value has dropped by a predetermined amount (e.g., 10%) or more, based on the retrieved CGMS record.

When the CGMS value has dropped by 10% or more, in step S147, CPU 110 records the changing point as a drift, and then ends the flow. On the other hand, when the CGMS value has not dropped by 10% or more, CPU 110 ends the processing without recording any drift.

Figure 35:
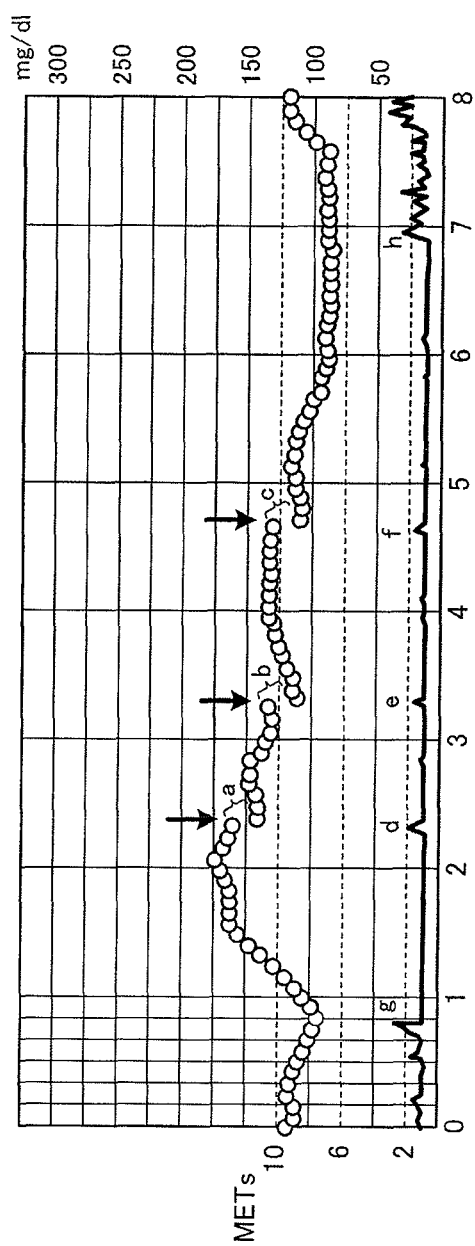
FIG. 35 shows a graph of CGMS values over time during sleeping measured with a CGM sensor unit according to Embodiment 7, and of activity levels over time during sleeping measured with an acceleration sensor in the CGM sensor unit.

FIG. 35 shows a graph of CGMS values over time during sleep, and a graph of activity levels of physical motions over time during sleep measured with acceleration sensor 112 of CGM sensor unit 500. In the diagram, the X axis is time, discrete white dots on the upper side are CGMS values in terms of mg/dl (right Y axis), and a continuous line on the lower side represents living activity levels in terms of METs (left Y axis) measured with the acceleration sensor.

The inventors attached CGM sensor unit 500 to a subject for simultaneous measurements of CGMS values and physical motions during sleep, allowing the measured CGMS values and motion information to be recorded in recording section 111 (FIG. 2) while associating them with each other.

FIG. 35 shows graphs respectively of the CGMS values and activity levels of physical motions during sleep, recorded in recording section 111. As seen from the graph of CGMS values, there occurred three unwanted discontinuities (hereinafter "drifts", see "a", "b" and "c" in the graph). At first, the inventors attributed these drifts to data acquisition errors caused by some reasons.

The inventors studied the results of CGMS measurement in combination with the results of physical motion measurement, and found that physical motions (see "d", "e" and "f") were detected at the same time as the drifts (see "a", "b" and "c"). Further experiments and studies revealed that the occurrence of a drift in conjunction with a certain physical motion corresponds to "turn over in bed" (see arrows).

It was also established that motion in the absence of a drift (see "g" and "h") is not "turn over in bed". The data of FIG. 35 indicates that the subject rolled over three times in bed during 8 sleep hours.

As described above, in this embodiment, by recording the measured CGM values and motion information in recording section 111 while associating them with each other, it has succeeded for the first time in providing the number of times the subject turned over in bed—novel information totally different motion information of CGM values, physical quantities. The times of turn over is an important parameter associated with the depth of sleep, or sleep quality.

The most notable points in the graph of FIG. 35 are drifts (see "a", "b" and "c"), discontinuities in the graph of CGMS. It can be seen that the drifts, or jumping of CGM values, were always accompanied by small peaks (2 METs or less) in the graph.

Because small peaks of 2 METs or less during sleep are derived from either rolling over in bed or blood glucose measurement by SGBG as described above, it can be seen herein that the small peaks in FIG. 35 are derived from rolling over in bed. CGMS sensor 600 measures glucose level every 1-5 minutes with a needle-type biosensor connected to a transmitter. The biosensor is 15 mm or less in length so as to reach the abdominal subcutaneous adipose tissue and is 26 gauge (0.4572 mm) to 21 gauge (0.8121 mm) in thickness.

Thus, CGMS sensor 600 itself is not directly secured to the body; it is a medical tape adhered to a jig connecting the transmitter and CGMS sensor 600 together that holds CGMS sensor 600. That is, it is considered that when physical motion occurs at the CGMS sensor attachment part, CGMS sensor 600, which is not as soft as adipocytes, is temporally separated from the surrounding adipose tissue, generating drifts in the graph of CGMS values.

Typically, each cycle of non-REM sleep and REM sleep is called a "sleep cycle" and is said to last approximately 90 minutes; therefore, for adults who sleep 8 hours a night, the cycle is repeated 5 times, and 4 times for adults who sleep 6 hours a night. Turn over occur during non-REM sleep.

That is, where only CGMS measurement is conducted in clinical applications, the occurrence of drifts every 90 minutes in the CGMS graph due to turn over makes the practitioner completely clueless as to which value is the CGMS value itself, which is clinically useless.

As described above, CGM sensor unit 500 according to this embodiment includes CGM sensor 600 to be connected to CGM sensor connector 600A, and living activity measurement section 500 that measures motions of physical activities. CGM sensor unit circuit section 510 records CGM values and motion information in recording section 111 (FIG. 2) while associating them with each other.

This embodiment thus can provide the same effect as Embodiment 1, i.e., can record novel information—CGM values associated with motion information—in recording section 111. With this information, it is made possible to realize accurate blood glucose management based on daily living activities such as eating and sleeping.

In particular, this embodiment provides a peculiar effect that CGM sensor unit 500 can measure CGM value and living activity level with one device, with the unit attached to the subject's body.

For example, CGM sensor unit 500 can record drifts that occur upon CGMS measurement during sleep. This allows medical practitioners to easily keep track of patient's blood glucose levels during sleep. As a result, clinical activities become more beneficial to diabetic patients.

Embodiment 8

Embodiment 8 describes an insulin pump unit. An insulin pump unit according to Embodiment 8 is an insulin infusion device, not a biosensor that measures blood glucose level or CGM value. It has been established, however, that a unprecedented effect can be provided upon priming (squirting a unit of insulin), by providing the insulin pump unit with a motion measurement section that measures motions of human activity.

Figure 36:
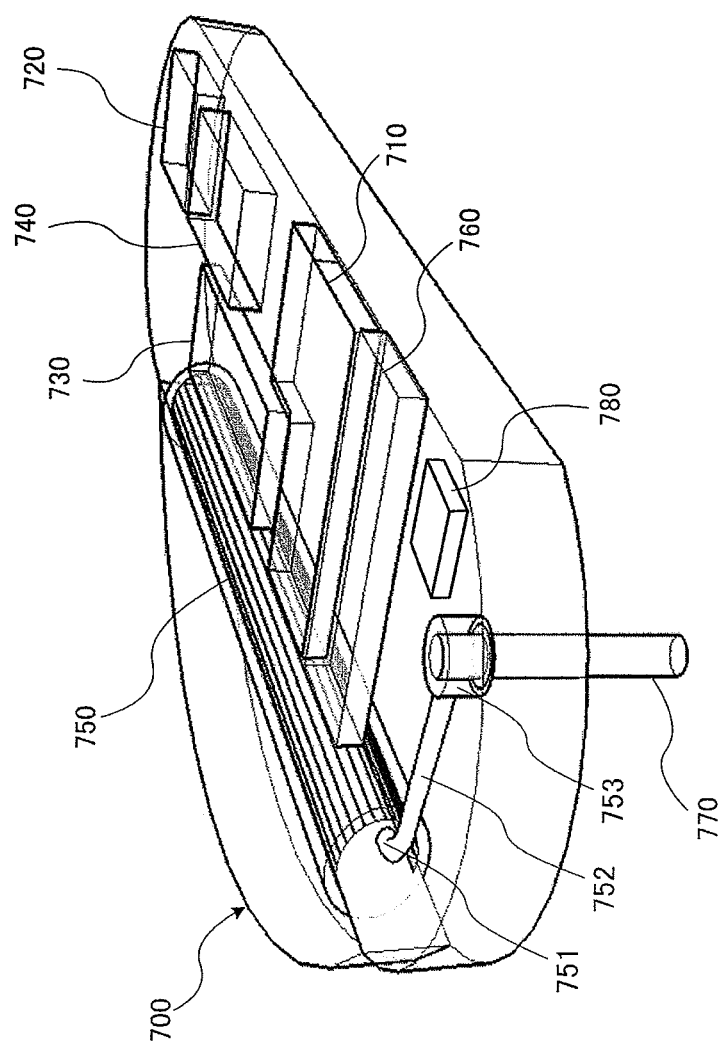
FIG. 36 is an overview illustration of an insulin pump unit according to Embodiment 8.

FIG. 36 is an overview illustration of an insulin pump unit according to Embodiment 8. This embodiment is an example in which a blood glucose measuring system is applied to an insulin pump unit.

As illustrated in FIG. 36, insulin pump unit 700 includes insulin pump unit circuit section 710, living activity measurement section 720, communication section 730, power supply 740, insulin infusion section 750, pump section 760, cannula 770, and temperature measurement section 780.

Insulin pump unit 700 illustrated in FIG. 31 is small, light and thin when compared with blood glucose measuring device 100 illustrated in FIG. 1, as is CGM sensor unit 500 illustrated in FIG. 31. There are no particular limitations to the size and shape of insulin pump unit 700; it is preferably small enough (e.g., coin size) that the subject does not feel discomfort even when carrying the device all the time. Insulin pump unit 700 is attached to the subject's body like CGM insulin pump unit 800 illustrated in FIG. 38 to be described later.

Insulin pump unit 700 is attached to the subject's body during use. For this reason, insulin pump unit 700 needs to be as small, light and this as possible, and therefore, a display section and other components are not disposed of.

Insulin pump unit circuit section 710 (controlling means) controls the operation of each section as well as the delivery of insulin, stored in the reservoir of insulin infusion section 750, under the skin via cannula 770 with pump section 760, based on the insulin delivery programs input to communication section 730. Insulin pump unit circuit section 710 also controls the transmission of the motion information, measured by living activity measurement section 720, to blood glucose measuring device 100 (see FIGS. 1 and 2) via communication section 730.

In particular, insulin pump unit circuit section 710 controls, based on the motion information, the operation of notifying the user of the timing of priming (squirting of insulin) of insulin pump unit 700 and of the recommended direction to which the user points the device upon priming. The operation of priming will be described in detail later with reference to FIG. 37.

Living activity measurement section 720 measures living activity level in the same manner as the motion measurement section (acceleration sensor 112) of FIGS. 1 and 2. In this case, in relation to the priming operation described later, vertical direction is standard direction.

As with communication section 530 illustrated in FIG. 36, communication section 730 is dedicated or general communication means and is either wireless or wired. In the case of wireless communication, low-power near-field bilateral wireless communication systems such as specified near-field wireless communication, Bluetooth®, Ultra Wideband (UWB), etc. are preferable.

Insulin infusion section 750 stores insulin in an internal cylinder. Insulin stored in the reservoir of insulin infusion section 750 is one directly delivered in the reservoir from the outside of insulin pump unit 700 using a syringe or the like (not shown).

This inevitably entails inclusion of air in the reservoir of insulin infusion section 750. Trapped air in the reservoir can be removed by appropriate priming (squirting a unit of insulin). However, this operation is time consuming.

Insulin infusion section 750 has opening 751 at one end, which is cannula 770 side. Opening 751 communicates with cannula connector 753 via communication channel 752.

Insulin stored in the reservoir of insulin infusion section 750 is delivered through opening 751, communication channel 752 and cannula connector 753 to cannula 770.

Because insulin infusion section 750 has a function of storing consumable insulin, it is preferably detachable from insulin pump unit 700. Insulin pump unit 700 can more precisely measure living activity as it is directly arranged on the skin.

Moreover, insulin pump unit 700 preferably has a temperature measuring function. Temperature measurement realizes detection of changes in the patient's insulin sensitivity. Moreover, temperature measurement can not only preclude troubles in the insulin pump unit, but also enable body temperature monitoring as a vital sign.

Pump section 760 delivers insulin to cannula 770, which is stored in the reservoir of insulin infusion section 750.

By measuring the operation time of pump section 760, insulin pump unit circuit section 710 can estimate the quantity of insulin delivered to cannula 770, i.e., the actual dose delivered to the body by continuous subcutaneous insulin infusion.

Further, insulin pump unit circuit section 710 can memorize the type and dose of bolus insulin previously administered by continuous subcutaneous insulin infusion. This allows for the estimation of the quantity of the last bolus insulin that is still active in the body (insulin on board).

Insulin pump unit circuit section 710 transmits the dose of bolus insulin administered by continuous subcutaneous insulin infusion and the quantity of remaining insulin to blood glucose measuring device 100 and the like via communication section 730. By this, it is possible to determine an appropriate insulin dose for the next administration, avoiding overdosing or under dosing and improving safety.

Cannula 770 is inserted under the skin for appropriate delivery of insulin. Insulin is one delivered from the reservoir of insulin infusion section 750.

Temperature measurement section 780 measures and outputs body temperature, which is then transmitted to blood glucose measuring device 100 and the like via communication section 730.

Next will describe the operation of the insulin pump unit having the structure described above, particularly the priming operation before pump attachment.

Figure 37:
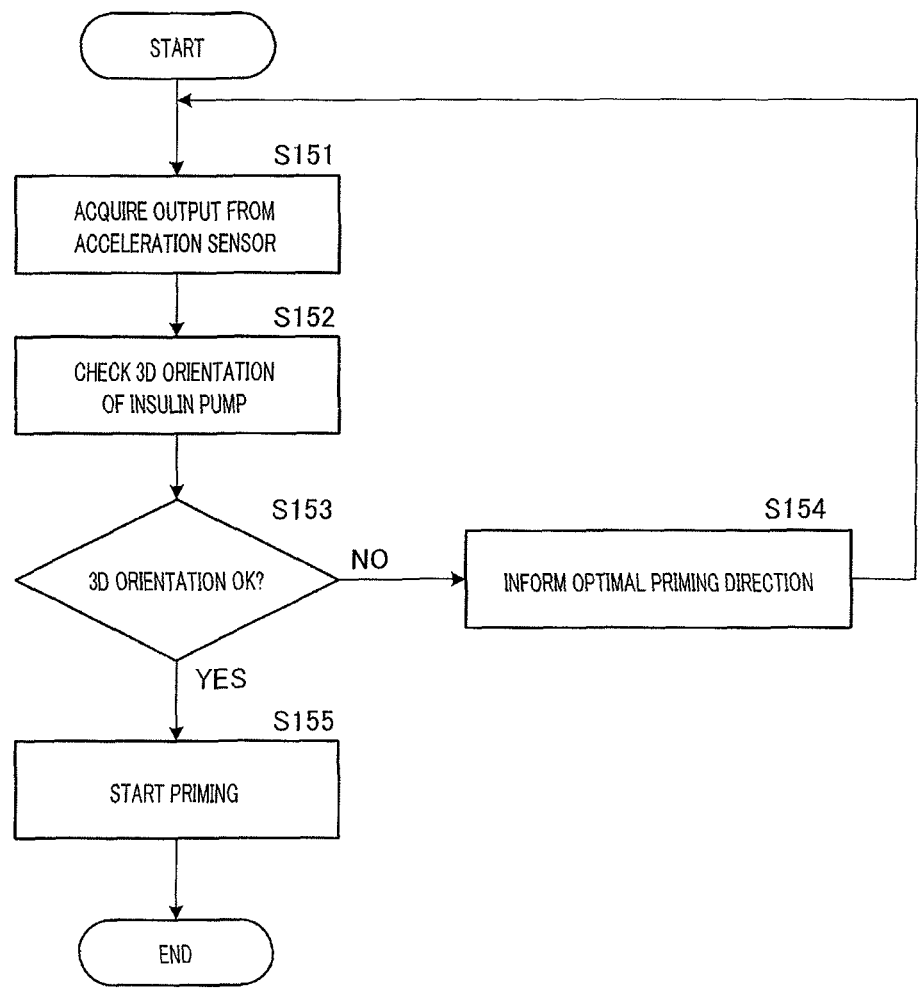
FIG. 37 is a flowchart of a pump priming operation of an insulin pump unit according to Embodiment 8.

FIG. 37 is a flowchart of a pump priming operation of insulin pump unit 700. This process is repeatedly executed by a CPU (not shown) of insulin pump unit circuit section 710 at predetermined timings. The CPU of insulin pump unit circuit 710 section performs the same processing as CPU 110 of blood glucose measuring device 100 illustrated in FIGS. 1 and 2 with regard to living activity measurement processing.

In step S151, the CPU acquires an output from acceleration sensor 112.

In step S152, the CPU confirms which side of insulin pump unit 700 faces up or down and which direction the device is oriented, based on the output from acceleration sensor 112.

In step S153, the CPU checks whether the side and three-dimensional orientation of insulin pump unit 70 are proper for priming.

When it is determined that side and the three-dimensional orientation and the like of the device are not proper for priming, the CPU 110 then notifies the user of an optimal priming direction, after which the process proceeds back to step S151. This embodiment is directed to an example of insulin pump unit 700 not provided with notification means such as a display section.

Accordingly, in practice, notification in step S154 is effected by transmitting via communication section 730 control commands to blood glucose measuring device 100 (FIGS. 1 and 2) equipped with notification means, so that blood glucose measuring device 100 notifies the user by beeping, displaying a message, by voice using voice synthesizer LSI, or any combinations thereof. Alternatively, insulin pump unit 700 may include a display section, an LED section, a voice synthesizer LSI, a speaker, all of which are not illustrated, for notification.

When the center axis of cylindrical insulin infusion section 750 in insulin pump unit 700 is, for example, made parallel to horizontal axis as illustrated in FIG. 36, there is concern that air, which should be purged by priming, remains in the reservoir of insulin infusion section 750.

In the case of FIG. 36, insulin pump unit 700 needs be held upright (vertical) so that opening 751 of insulin infusion section 750 faces up. As soon as insulin pump unit 700 is held upright by the user, he/she is notified to that effect. Alternatively, the user is notified of the fact that proper priming is impossible unless insulin pump unit 700 is held upright.

When it is determined that three-dimensional orientation of the insulin pump is proper for priming, priming is commenced in step S155, and ends the flow.

By executing the above flow, the following effect can be brought about.

Iusulet Corporation (U.S.) recently released OmniPod®, an infusion set-free disposable insulin pump. This system solves the problems pertinent in tubed insulin pumps, including possible injuries caused by the snagging of the infusion set's tubing on objects, and possible elevated blood glucose level during sleep that occurs when the user unwittingly bends his/her tubing under the body during sleep to block the insulin flow. Nevertheless, this system is not yet easy to use, because the patient needs to fill the insulin reservoir using an syringe following by priming of the tubing.

In particular, with this system, it is highly likely that all of the air bubbles cannot be purged by priming, because insulin is a peptide and thus is easy to bubble and because insulin's state is difficult to confirm in a reservoir of a disposable insulin pump compared to that of an insulin pump that requires an infusion set. Injection of insulin that is not completely free of bubbles results in a smaller insulin dose than is originally intended, which may lead to, even temporarily, elevated blood glucose levels.

The OmniPod® adopts a configuration that the reservoir delivery the insulin to catheter is placed at a position opposite to the catheter delivery the insulin to subcutaneous. Because of the configuration, the pod is upside down. Therefore, bubbles are likely to remain in the pod.

To solve the problem, in this embodiment, insulin pump unit 700 is applied to an infusion set-free disposable insulin pump capable of wireless communication.

Insulin pump unit 700 includes acceleration sensor 112, and insulin pump unit circuit section 710 controls the operation of notifying the timing of priming of insulin pump unit 700 or recommended priming direction, based on the measured motion information.

Upon priming, the user can point the disposable insulin pump to an optimal direction, and thus, the device becomes significantly easy to use. Such an insulin infusion device where priming direction is optimized has not heretofore been available in the art.

An optimal direction to which insulin pump unit 700 is oriented for priming relies on the directions of opening 751 and communication channel 752 that connect insulin infusion section 750 with cannula 770, not the direction of cannula 770 to be inserted under the skin. Because opening 751 and communication channel 750 are provided inside insulin pump unit 700, they are hard to recognize. In this embodiment, it is possible to improve safety by helping the user prime insulin pump unit 700.

Embodiment 9

Figure 38:
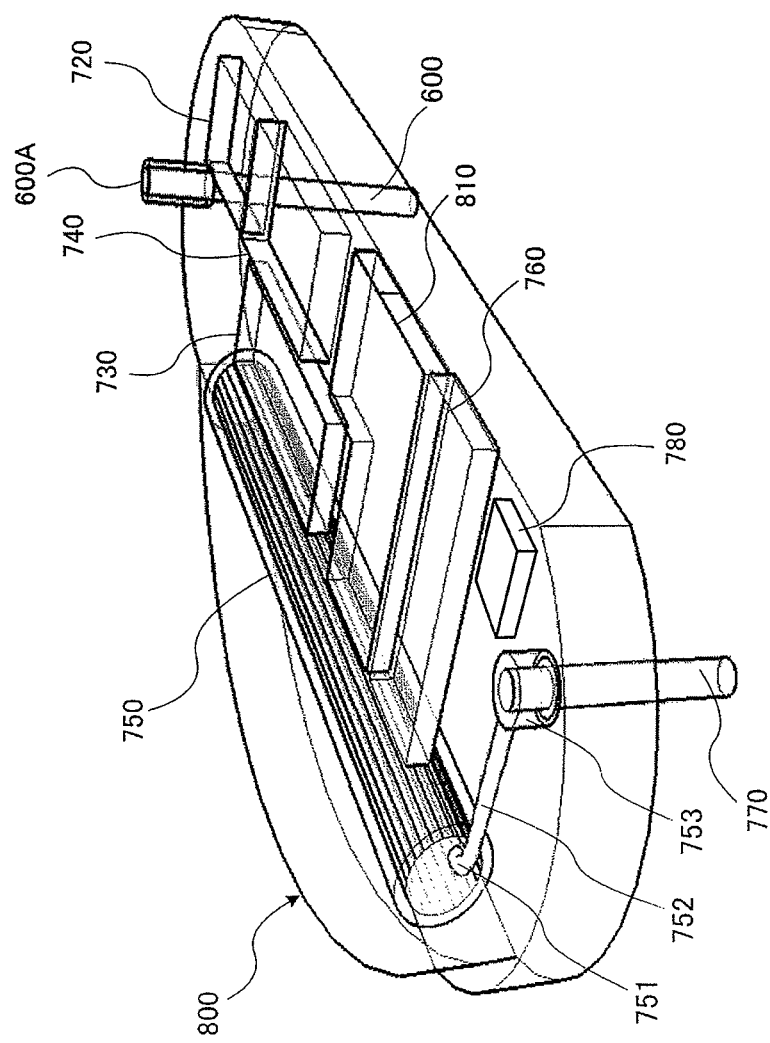
FIG. 38 is an overview illustration of a CGM insulin pump unit according to Embodiment 9.

FIG. 38 is an overview illustration of a CGM insulin pump unit according to Embodiment 9, a unit in which CGM sensor unit 500 according to Embodiment 9 and insulin pump unit 700 according to Embodiment 8 are combined. Like components are denoted by the same numerals as those in FIGS. 31 and 36 and will not be explained.

As illustrated in FIG. 38, CGM insulin pump unit 800 includes CGM sensor 600, CGM insulin pump unit circuit section 810, living activity measurement section 720, communication section 730, power supply 740, insulin infusion section 750, pump section 760, cannula 770, and temperature measurement section 780.

CGM sensor 600 and cannula 770 are inserted under the skin, and CGM sensor 600 continuously measures glucose levels in the interstitial fluid. CGM sensor 600 has a reagent such as enzyme immobilized thereon.

Cannula 770 inserted under the skin delivers insulin as needed, which is stored in the reservoir of insulin infusion section 750.

Because insulin infusion section 750 has a function of storing consumable insulin, it is preferably detachable from CGM insulin pump unit 800. Although the two sections are shown as separate parts, they may be integrated as a single section.

CGM insulin pump unit circuit section 810 controls not only the operation of each section, but also the transmission of glucose levels in the interstitial fluid measured by CGM sensor 600 and living activity levels measured by living activity measurement section 720 to the blood glucose measuring device (see FIGS. 1 and 2) via communication section 730.

CGM insulin pump unit circuit section 810 also controls the transmission of the motion information measured by living activity measurement section 720 to blood glucose measuring device 100 (see FIGS. 1 and 2) via communication section 730.

Moreover, CGM insulin pump unit circuit section 810 records in recording section 111 (FIG. 2) the motion information of physical activities measured by acceleration sensor 112 and the CGM values measured by CGM sensor 600, while associating motion information and CGM values with each other. In this case, CGM insulin pump unit circuit section 810 may be so configured to calculate living activity levels based on the measured values which have been associated with the motion information and recorded in recording section 111.

CGM insulin pump unit circuit section 810 controls, based on the motion information, the operation of notifying the user of the timing of priming of insulin pump unit 700 and of the recommended direction to which the user points the unit upon priming. The operation of priming will be described in detail later with reference to FIG. 37.

As CGM insulin pump unit 800 is placed directly on the skin, more precise living activity measurement is possible. Moreover, CGM insulin pump unit 800 preferably has a temperature measuring function. Temperature measurement prevents the CGM sensor from generating abnormal values, realizes detection of changes in the patient's insulin sensitivity, precludes troubles in the insulin pump, and enables body temperature monitoring as a vital sign.

Figure 39B:
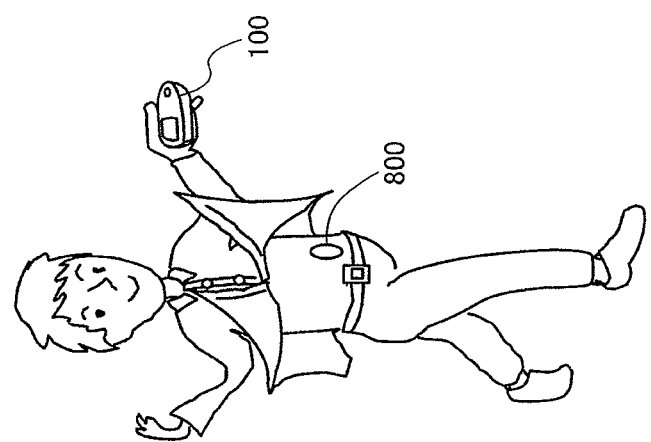
FIGS. 39A and 39B illustrate how a CGM insulin pump unit according to Embodiment 9 is carried by a user.
Figure 39A:
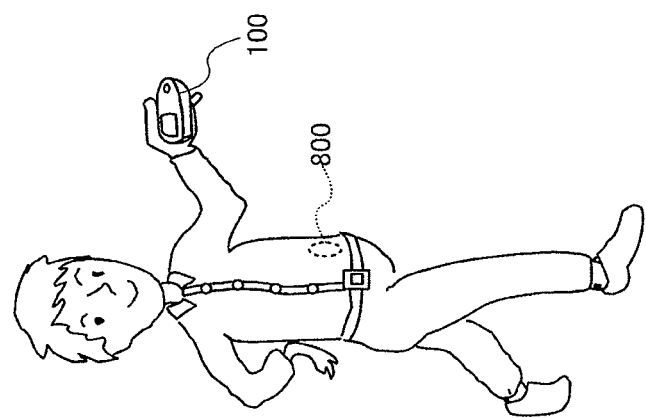

FIGS. 39A and 39B illustrate how CGM insulin pump unit 800 is carried by a user.

As illustrated in FIG. 39A, CGM insulin pump unit 800 is attached directly to the skin. That is, CGM sensor 600 and cannula 700 are inserted under the skin, and CGM insulin pump unit 800 is attached to the skin with a medical tape or the like.

In daily life the user cannot see the device as it is hidden under the clothes, as illustrated in FIG. 39A. The user can see the device by taking off the clothes, as illustrated in FIG. 39B.

CGM insulin pump unit 800 communicates with blood glucose measuring device 100 via communication section 730 using a low-power near-field bilateral wireless communication system such as specified near-field wireless communication or Bluetooth®.

As described above, CGM insulin pump unit 800 directly placed on the skin can record more precise living activity levels in recording section 111 (FIG. 2). Blood glucose measuring device 100 thus can receive more precise living activity levels from CGM insulin pump unit 800, enabling controls and data management described in Embodiments 1 to 5.

In cases where CGM insulin pump unit 800 does not include any notification means such as a display section, blood glucose measuring device 100 receives data transmitted from communication section 730 of CGM insulin pump unit 800, and then notifies the user of priming operation information, in conjunction with the function of CGM insulin pump unit 800.

Figure 40:
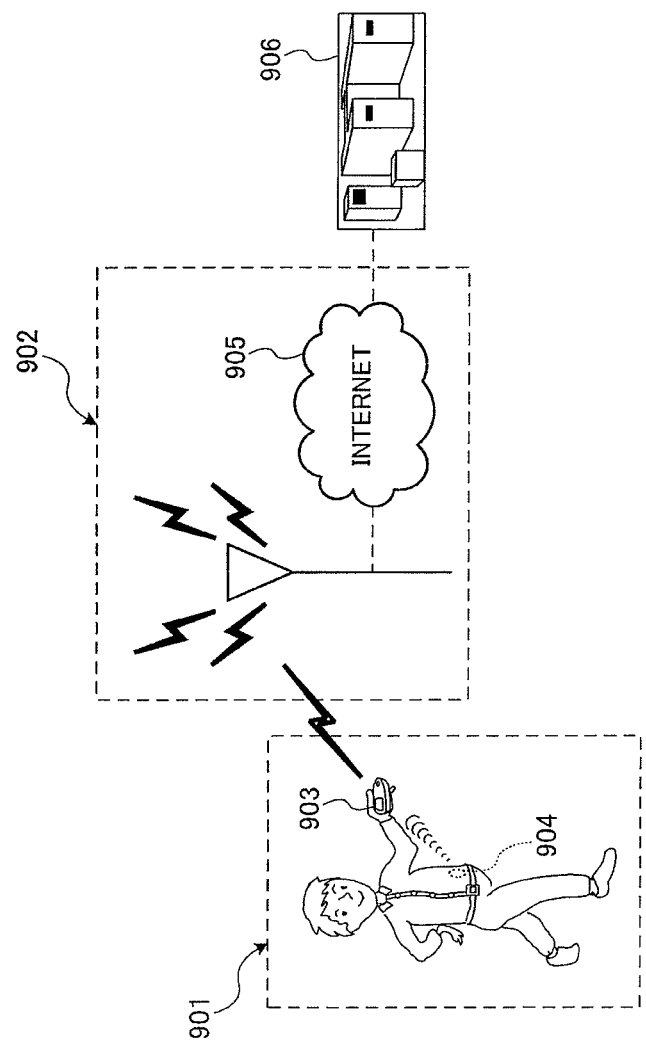
FIG. 40 is a conceptual diagram of a blood glucose measuring system according to Embodiment 9.

FIG. 40 is a conceptual diagram of a blood glucose measuring system.

As illustrated in FIG. 40. the system includes short range communication system 901, electronic communication system 902, computer 903, and device 904.

Electronic communication system 902 wirelessly transmits or receives data to or from computer 903. Wired communication is also possible, instead of wireless communication. Computer 903 is coupled to calculation device 906 via Internet 905. Thus, bilateral communication is established between computer 903 and calculation device 906.

Device 904 is, more specifically, CGM insulin pump unit 800 illustrated in FIG. 39. While CGM insulin pump unit 800 is preferably a CGM insulin pump capable of monitoring of living activity level, CGM sensor unit 500 and insulin pump unit 700, both of which are capable of monitoring of living activity level, can be employed singly.

Computer 903 transmits the monitored information to calculation device 906. As one use example, the user can order a consumable good by confirming the information displayed on the screen of computer 903. Calculation device 906 can transmit an encouraging message or analysis result to computer 903

Embodiment 10

Embodiment 10 describes arbitrary meal event input mode and its importance.

Meal events have been described in detail in Embodiment 2 (see FIGS. 16 to 19).

As has been described in Embodiments above, detection of meal events is clinically very important. For diabetic patients, the relationship between meal and blood glucose level is particularly important. In order to make the device available worldwide in the current world where we face a growing epidemic of diabetes, we should first consider the big differences in eating customs among countries or regions, rather than technical issues. Eating customs vary greatly across the globe—which include eating on the floor, eating at the table, eating with chopsticks, spoons or forks, etc.

The hardware configuration of a blood glucose measuring system according to Embodiment 10 of the present invention is identical to that illustrated in FIGS. 1 to 3. It is, of course, possible to apply the hardware configuration to CGM sensor unit 500 illustrated in FIG. 31, insulin pump unit 700 illustrated in FIG. 36, or CGM insulin pump unit 800 illustrated in FIG. 38.

[Arbitrary Meal Event Input Mode]

Figure 41:
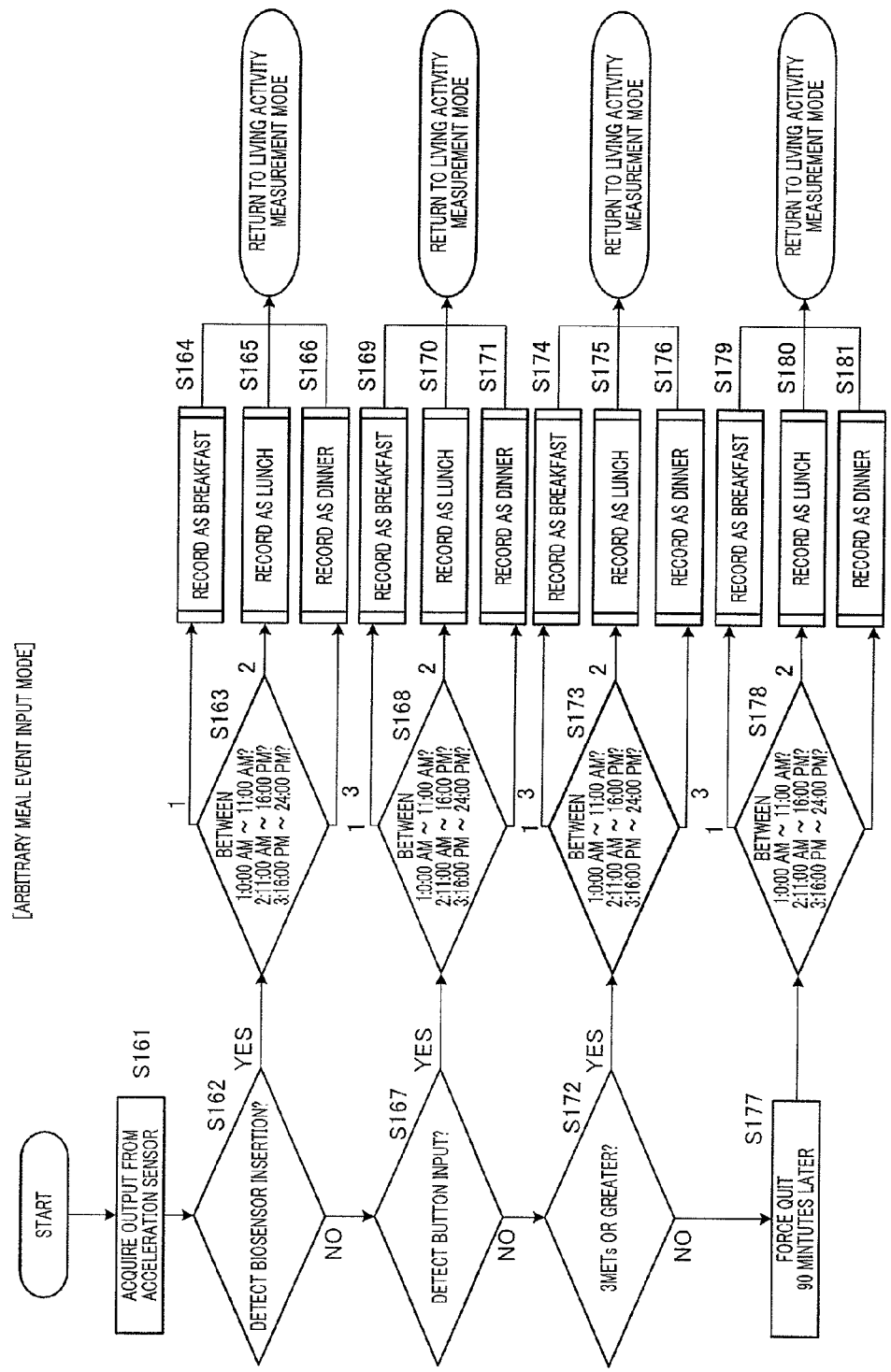
FIG. 41 is a flowchart of arbitrary meal event input mode in a blood glucose measuring system according to Embodiment 10.

FIG. 41 is a flowchart of arbitrary meal event input mode. This flow is repeatedly executed by CPU 110 of blood glucose measuring device 100 (FIGS. 1 and 2) at predetermined timings.

When arbitrary meal event input mode is started, CPU 110 acquires an output from acceleration sensor (motion measurement section) 112 (FIG. 2) in step S161.

In step S162, CPU 110 determines whether or not biosensor 200 (FIG. 2) has been inserted.

When insertion of biosensor 200 has been detected, in step S163, CPU 110 determines whether detection was made between 0:00 am and 11:00 am, between 11:00 am and 16:00 pm, or between 16:00 pm and 24:00 pm.

When the time zone is between 0:00 am and 11:00 pm, in step S164, CPU 110 records in recording section 111 (FIG. 2) the fact the acceleration pattern after start corresponds to breakfast. When the time zone is between 11:00 am and 16:00 pm, in step S165, CPU 110 records in recording section 111 the fact the acceleration pattern after start corresponds to lunch. When the time zone is between 16:00 pm and 24:00 pm, in step S166, CPU 110 records in recording section 111 the fact the acceleration pattern after start corresponds to dinner.

After recording of the acceleration pattern of meal, CPU 110 switches the device from [arbitrary meal event input mode] to [living activity measurement mode] (FIG. 8).

When insertion of biosensor 200 has not been detected in step S162, the process proceeds to step S167.

In step S167, CPU 110 determines whether or not any previously set button has been pressed.

When pressing of any previously set button has been detected, in step S168, CPU 110 determines whether the input was received between 0:00 am and 11:00 am, between 11:00 am and 16:00 pm, or between 16:00 pm and 24:00 pm.

When the time zone is between 0:00 am and 11:00 pm, in step S169, CPU 110 records in recording section 111 the fact the acceleration pattern after start corresponds to breakfast. When the time zone is between 11:00 am and 16:00 pm, in step S170, CPU 110 records in recording section 111 the fact the acceleration pattern after start corresponds to lunch. When the time zone is between 16:00 pm and 24:00 pm, in step S171, CPU 110 records in recording section 111 the fact the acceleration pattern after start corresponds to dinner.

After recording of the acceleration pattern of meal, CPU 110 switches the device from [arbitrary meal event input mode] to [living activity measurement mode] (FIG. 8).

When receipt of input has not been detected in step S167, the process proceeds to step S172.

In step S172, CPU 110 determines whether or not the living activity level calculated based the output from acceleration sensor 112 is 3 METs or greater.

When it has been determined that the living activity level calculated based the output from acceleration sensor 112 is 3 METs or greater, in step S173, CPU 110 determines whether the detection was made between 0:00 am and 11:00 am, between 11:00 am and 16:00 pm, or between 16:00 pm and 24:00 pm.

When the time zone is between 0:00 am and 11:00 pm, in step S174, CPU 110 records in recording section 111 the fact the acceleration pattern after start corresponds to breakfast. When the time zone is between 11:00 am and 16:00 pm, in step S175, CPU 110 records in recording section 111 the fact the acceleration pattern after start corresponds to lunch. When the time zone is between 16:00 pm and 24:00 pm, in step S176, CPU 110 records in recording section 111 the fact the acceleration pattern after start corresponds to dinner.

After recording of the acceleration pattern of meal, CPU 110 switches the device from [arbitrary meal event input mode] to [living activity measurement mode] (FIG. 8).

When it has not been determined in step S172 that the living activity level calculated based the output from acceleration sensor 112 is 3 METs or greater, in step S177, CPU 110 prepares for force termination of [arbitrary meal event input mode] 90 minutes later. That is, CPU 110 counts 90 minutes in step S177 before proceeding to step S178.

In step S178, CPU 110 determines whether the time zone is between 0:00 am and 11:00 am, between 11:00 am and 16:00 pm, or between 16:00 pm and 24:00 pm.

When the time zone is between 0:00 am and 11:00 pm, in step S179, CPU 110 records in recording section 111 the fact the acceleration pattern after start corresponds to breakfast. When the time zone is between 11:00 am and 16:00 pm, in step S180, CPU 110 records in recording section 111 the fact the acceleration pattern after start corresponds to lunch. When the time zone is between 16:00 pm and 24:00 pm, in step S181, CPU 110 records in recording section 111 the fact the acceleration pattern after start corresponds to dinner.

After recording of the acceleration pattern of meal, CPU 110 switches the device from [arbitrary meal event input mode] to [living activity measurement mode] (FIG. 8).

By executing the above flow, after detection of an output from acceleration sensor 112, such events as insertion of biosensor 200, button pressing, or elevation of living activity level, can be correlated with meals.

[Arbitrary Meal Event Detection Processing Mode]

Figure 42:
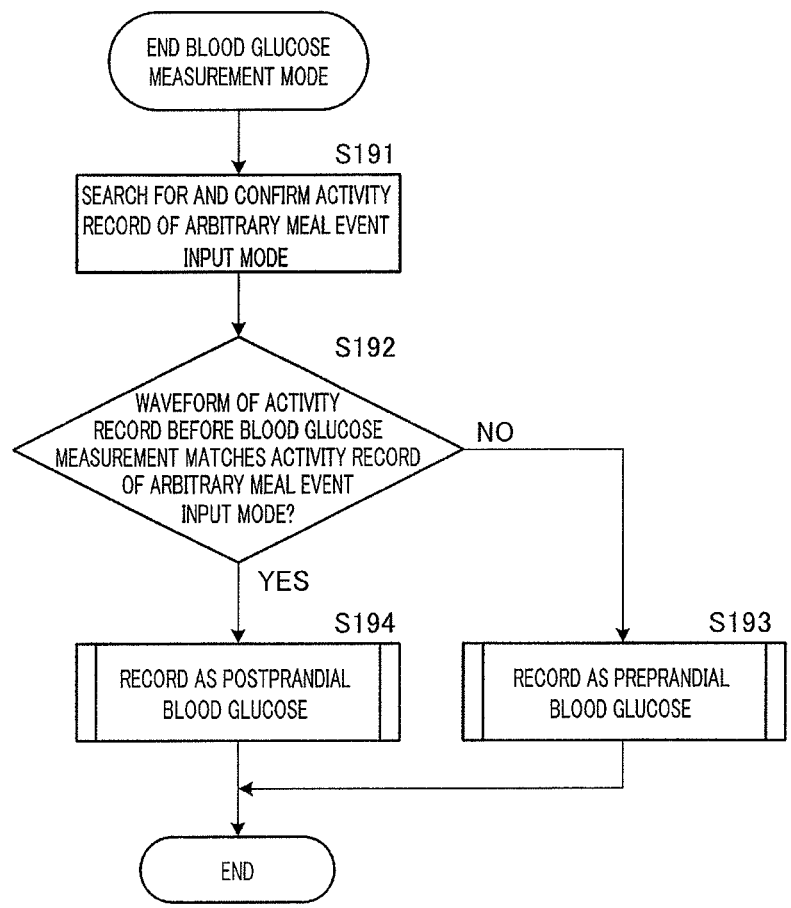
FIG. 42 is a flowchart of arbitrary meal event detection processing mode according to arbitral inputs in a blood glucose measuring system according to Embodiment 10.

FIG. 42 is a flowchart of arbitrary meal event detection processing mode activated according to arbitrary input.

First, in step S191, CPU 110 searches recording section 111 for the activity record obtained in arbitrary meal event input mode.

In step S192, CPU 110 determines whether or not the waveform of the activity record before blood glucose measurement matches the waveform of the activity record of arbitrary meal event input mode.

When the waveform of the activity record before blood glucose measurement does not match the waveform of the activity record of arbitrary meal event input mode, in step S193, CPU 110 records in recording section 111 the fact that blood glucose level was measured preprandially.

On the other hand, when the waveform of the activity record before blood glucose measurement matches waveform of the activity record of arbitrary meal event input mode, in step S194, CPU 110 records in recording section 111 the fact that blood glucose level was measured postprandially, and ends the flow.

Thus, by recording various user's physical activity patterns for a meal, this embodiment enables to automatically and precisely determine whether blood glucose measurement, which is clinically important, is made preprandially or postprandially, without bothering the patient.

Embodiment 11

Embodiment 11 demonstrates displaying novel information with regard to changes over time in living activity level and blood glucose level, which is one embodiment of [B. living activity measurement control].

The hardware configuration of a blood glucose measuring system according to Embodiment 11 of the present invention is identical to that illustrated in FIGS. 1 to 3.

Figure 43:
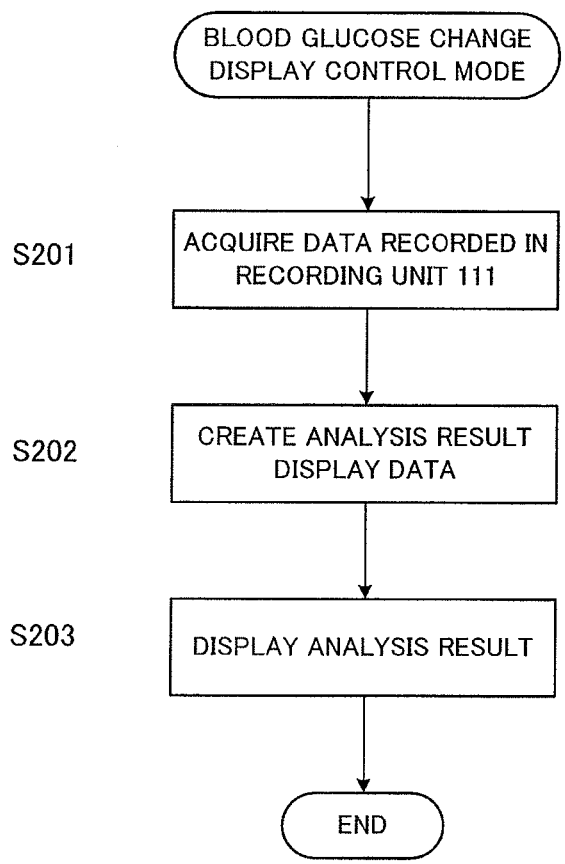
FIG. 43 is a flowchart of controlling displaying, from a new viewpoint, changes over time in living activity level and blood glucose level on a blood glucose measuring system according to Embodiment 10.

FIG. 43 is a flowchart of controlling displaying, from a new viewpoint, changes over time in living activity level and blood glucose level. This flow is repeatedly executed by CPU 110 of blood glucose measuring device 100 (FIGS. 1 and 2) at predetermined timings.

Once [blood glucose level change display control mode] is started, in step S201, CPU 110 acquires blood glucose level data which has been associated with living activity level and stored in recording section 111 (FIG. 2).

As has been described in Embodiments above, daily living activities to be stored in recording section 111 include meal events (meal time, meal time zone) and sleep events (sleep duration, sleep time zone, or the times of turn over or the number of waking episodes), which are detected by motion measurement section (acceleration sensor) 112 (FIG. 2) and, combined with blood glucose level data from blood glucose sensor 200, recorded in recording section 111 (FIG. 2).

Recording methods have been described in detail in Embodiment 1 (FIGS. 8, 10 and 12), Embodiments 2 to 4 (FIGS. 16 to 22), and Embodiment 10 (FIG. 42), for example. Living activity level may be combined with CGM value or insulin dose, rather than blood glucose level, as has been described in detail in Embodiment 7 (FIG. 33) and Embodiment 8 (FIG. 37), for example. Needless to say, novel information can be displayed by providing various combinations of these parameters.

Referring the flow shown in FIG. 43 again, in steps S202, CPU 110 creates display data based on new findings by combining the living activity levels with blood glucose levels (or CGM values or insulin doses) acquired.

In step S203, CPU 110 displays the created data on display section 102 (FIGS. 1 and 2), and ends this flow.

FIGS. 44 to 47 illustrate an example of displayed data created and displayed by executing the above flow.

Figure 44:
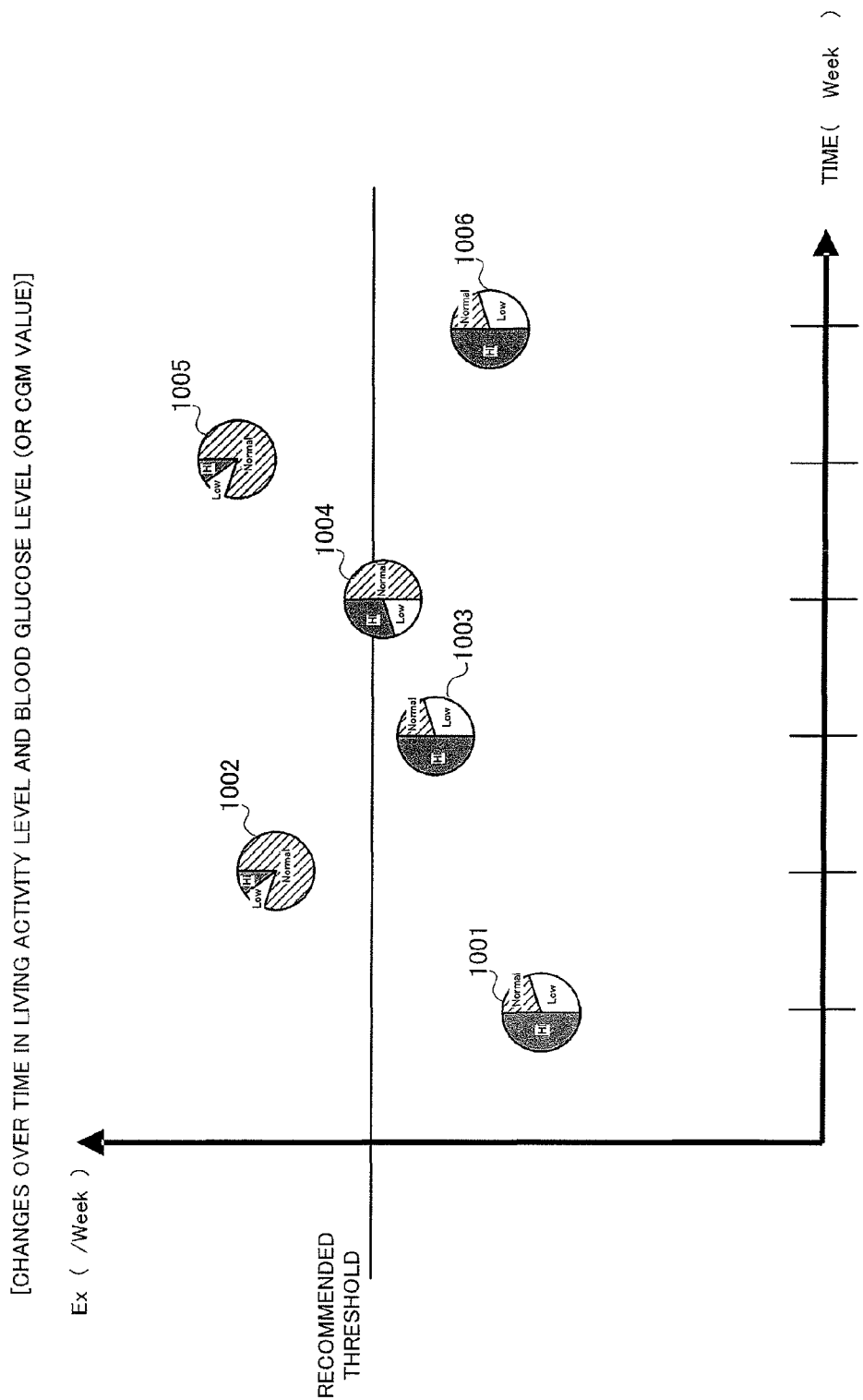
FIG. 44 illustrates an example of display of changes over time in living activity level and blood glucose level or CGM value on a blood glucose measuring system according to Embodiment 11.

FIG. 44 illustrates an example of display of changes over time in living activity level and blood glucose level or CGM value, where the horizontal axis is time which is graduated in weeks, and the vertical axis is exercise amount per week. Moreover, a recommended threshold is set for the exercise amount in this graph.

As illustrated in FIG. 44, each week's blood glucose level, coupled with living activity level, is plotted on a graph. Blood glucose levels 1001 to 1006 are each displayed as a pie chart in which blood glucose levels measured in the week are classified into low, normal and high groups. Normal group is indicated by hatch lines, low group is indicated by a blank, and high group (abbreviated as "HI" in the chart) is indicated by a shaded area. These groups may be distinguished by different colors.

In the pie chart, "Normal" means standard blood glucose level, e.g., 70-180 mg/dl, "Low" means low blood glucose level, which is 70 mg/dl or less, and "High" means high blood glucose level, which is 180 mg/dl or higher.

In this way, blood glucose levels 1001 to 1006 are expressed as pie charts consisting of Normal, Low and High sections while being correlated with the corresponding weekly living activity levels. That is, blood glucose levels 1001 to 1006 appear as pie charts with which users can confirm blood glucose levels in units of normal, low and high at a glance, and the pie charts plotted against the corresponding values of exercise amount (living activity level).

In other words, the measured blood glucose levels are stored while being correlated with the weekly exercise amount, and the blood glucose levels are displayed while being classified into normal, low and high levels. Note that although changes in exercise amount and blood glucose level are displayed on a weekly basis, the changes may also be displayed on a 2 to 5 days basis, or hourly basis, for example.

With this graph, users can confirm weekly changes in living activity level and blood glucose level. Referring blood glucose level 1001 of FIG. 44, it can be seen at a glance that, for the first week, "High" accounted for approximately half of the total measured blood glucose levels 1001, with "Low" and "Normal" accounting for approximately ⅓ and less than ¼, respectively.

Blood glucose level 1001 also indicates circumstances of exercise in the first week; it can be seen that the first week's exercise was sluggish (lowest in the graph), suggesting that, where the subject is a diabetic patient, he/she did little exercise which deems to be effective. The subject's bad blood glucose readings can be correlated with the low exercise amount.

Referring the second week, it can be seen that "Normal" accounted for about ¾ of the total, and "High" and "Low" accounted for less than ¼ in total. It can also be seen that the subject did much exercise to an extent exceeding the recommended threshold value. It can be understood that the subject's blood glucose level correlates with exercise amount.

It is the third week when the subject reduced exercise amount (living activity level). Referring the third week, the subject's blood glucose level readings, once improved in the second week, deteriorated to a level comparable to that of the first week. That is, in the third week, "High" accounted for approximately half of the total, whereas "Low" accounted for approximately ⅓, and "Normal" accounted for approximately less than ¼. It can also be seen that the subject did exercise to an extent not exceeding the recommended threshold value. It is possible to simultaneously observe these changes over time in living activity level and blood glucose level.

Referring the fourth week, "Normal" accounted for approximately half of the total, whereas "High" accounted for approximately ⅓ and "Low" accounted for approximately less than ¼. It can also be seen that the subject only did exercise to an extent just below the recommended threshold value. It is possible to simultaneously observe these changes over time in living activity level and blood glucose level.

Referring the fifth week, as in the second week, "Normal" accounted for about ¾ of the total, with "High" and "Low" accounting for approximately less than ¼ in total. It can also be seen that the amount of exercise is large in the second week (largest in this graph), suggesting that the subject did effective exercise sufficiently to an extent exceeding the recommended threshold value.

Referring the sixth week, the subject's blood glucose level readings, once improved in the fifth week, deteriorated to a level comparable to that of the third week. That is, in the sixth week, "High" accounted for approximately half of the total, whereas "Low" accounted for approximately ⅓, and "Normal" accounted for approximately less than ¼. It can also be seen that the subject only did exercise to an extent not exceeding the recommended threshold value. It is possible to simultaneously observe these changes over time in living activity level and blood glucose level.

The net result of the above is that the subject's living activity level and blood glucose level are closely correlated with each other, demonstrating that doing exercise is significantly effective for improving blood glucose level readings. It is generally known that exercise improves blood glucose level; however, no measures have been available in the art that allow users to know how much exercise is needed to improve blood glucose readings.

According to this embodiment, it is possible to quantitatively inform how blood glucose level changed by exercise during a given period. It is the present invention that first discloses creating such novel display data.

It should be noted that this embodiment by no means displays mere changes in blood glucose level over time by indicating whether it falls within a low, normal or high range. By way of example, where a patient is on medication, it may be that the patient's blood glucose level falls within a normal level for approximately ¾ of a certain week, like blood glucose level 1002 of FIG. 44. As long as attempting to improve blood glucose readings, administration of medication poses no problem; however, this is not preferable when intending to ameliorate diabetes without relying on any medication. By simply measuring blood glucose levels, it is totally impossible to decide whether blood glucose readings have been improved by medication or for other reasons.

The most desirable case for diabetic patients is that their blood glucose level is kept within a normal range by moderate exercise that exceeds a recommended threshold level. By displaying a correlation between blood glucose level and exercise, patients can realize the effectiveness of exercise.

Moreover, doctors can make use of the above information for clinical purposes. For example, a display of changes over time in blood glucose level and living activity level like that shown in FIG. 44 allows doctors to quantitatively monitor the degree of correlation between exercise and blood glucose level of the patient, to decide medication type, dose, and frequency of administration. Furthermore, with this information, doctors can instruct their patients to do some exercise.

As to the recommended threshold of exercise, doctors can advice their patients to do moderate exercise which does not put excessive load on the body. For those patients whose degree of correlation between exercise and blood glucose level is relatively small, doctors can instruct them not to do exercise excessively.

In this way, according to this embodiment, it is possible to display novel display data with regard to changes over time in blood glucose level and living activity level.

Figure 45:
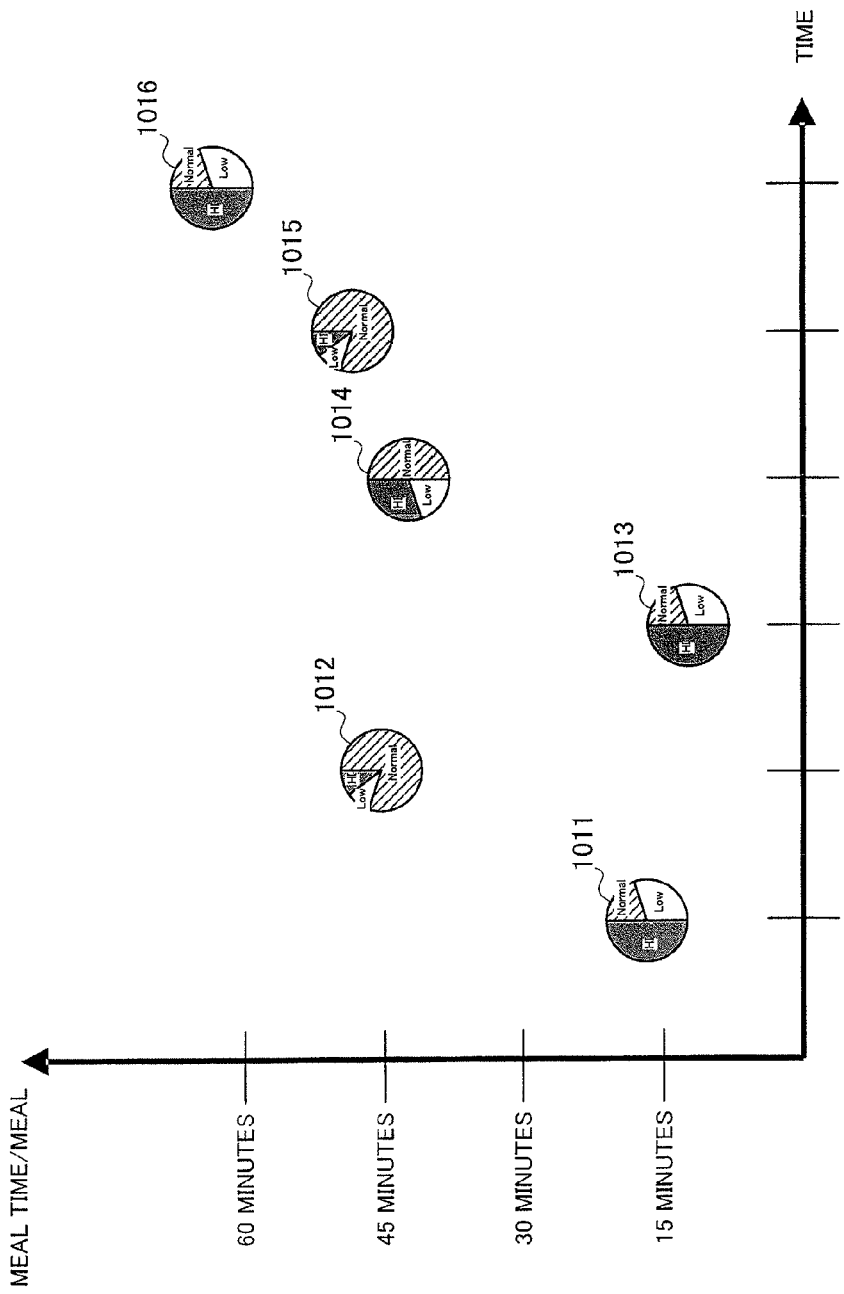
FIG. 45 illustrates an example of displaying changes over time in meal time per meal and blood glucose level or CGM value on a blood glucose measuring system according to Embodiment 11.

FIG. 45 illustrates an example of displaying changes over time in meal time per meal and blood glucose level or CGM value, where the horizontal axis is time which is graduated in days, and the vertical axis is meal time per meal, which is a mean meal time of the day.

As illustrated in FIG. 45, each day's blood glucose level, coupled with meal time per meal, is plotted on a graph. Blood glucose levels 1011 to 1016 are each displayed as a pie chart in which blood glucose readings in the day are classified into low, normal and high groups. Normal group is indicated by hatch lines, low group is indicated by a blank, and high group (abbreviated as "HI" in the chart) is indicated by a shaded area. These groups may be distinguished by different colors.

In the pie chart, "Normal" means standard blood glucose level, e.g., 70-180 mg/dl, "Low" means low blood glucose level, which is 70 mg/dl or less, and "High" means high blood glucose level, which is 180 mg/dl or higher.

In this way, blood glucose levels 1011 to 1016 are expressed as pie charts consisting of Normal, Low and High sections while being correlated with the corresponding meal time per meal.

This graph allows for monitoring of daily changes in blood glucose level and meal time per meal. Referring blood glucose level 1011 of FIG. 45, it can be seen at a glance that when the meal time per meal is little over 15 minutes, "High" accounted for approximately half of the total, with "Low" and "Normal" accounting for approximately ⅓ and less than ¼, respectively.

Blood glucose level 1012 is one in which meal time per meal was about 45 minutes. It can be seen that "Normal" accounted for approximately ¾ of the total and "High" and "Low" accounted for approximately less than ¼ in total.

Blood glucose level 1013 is one in which meal time per meal was about 15 minutes. As in the case of blood glucose level 1011, it can be seen at a glance that "High" accounted for approximately half of the total, "Low" account for approximately ⅓, and "Normal" accounted for approximately less than ¼.

Blood glucose level 1014 is one in which meal time per meal was about 45 minutes. It can be seen that "Normal" accounted for approximately half of the total, "High" accounted for approximately ⅓, and "Low" accounted for approximately less than ¼.

Blood glucose level 1015 is one in which meal time per meal was about 50 minutes. It can be seen that "Normal" accounted for approximately ¾ of the total, and "High" and "Low" accounted for approximately less than ¼ in total, as in the case of blood glucose level 1012.

Blood glucose level 1016 is one in which meal time per meal was over 60 minutes. It can be seen at a glance that "High" accounted for approximately half of the total, "Low" account for approximately ⅓, and "Normal" accounted for approximately less than ¼.

Blood glucose levels 1011 and 1013 in this graph, in which meal time per meal is about 15 minutes, support the general concept that individuals with short meal time, or speed eaters, tend to overeat and show elevated blood glucose levels. Namely, it has been learned that it is advantageous to take a longer time to eat a meal for normalizing blood glucose level.

In blood glucose levels 1012, 1014 and 1015 where meal time per meal is about 45 minutes, "Normal" accounted for more than half of the total. It has been established that taking 45 minutes to eat a meal by itself makes it possible to normalize blood glucose levels even when other conditions (e.g., exercise amount) are identical.

In the case of blood glucose level 1016 where the meal time per meal exceeds 60 minutes, the proportion of "Normal" decreased to approximately less than ¼—a result that runs against the above conclusion that longer meal time leads to normalization of blood glucose level. The reason for this remains elusive, but may be due to overeating of such a meal that easily raises blood glucose level.

With reference to FIG. 45 showing an example of a correlation between meal time per meal and blood glucose level, it has been established that taking 45 minutes or longer to eat a meal results in normalization of blood glucose level. By displaying the correlation between meal time per meal and blood glucose level, subjects can realize the effectiveness of prolonging meal time. These results support the general concept that shorter meal time results in unwanted rapid rise in blood glucose level particularly in diabetic patients. Although shorter meal time can be considered as an inherent habit, it may be attributed to busy lifestyle.

In this way, according to this embodiment, it is possible to display novel display data with regard to changes over time in blood glucose level and meal time per meal, which information leads to improved dietary habits.

Figure 46:
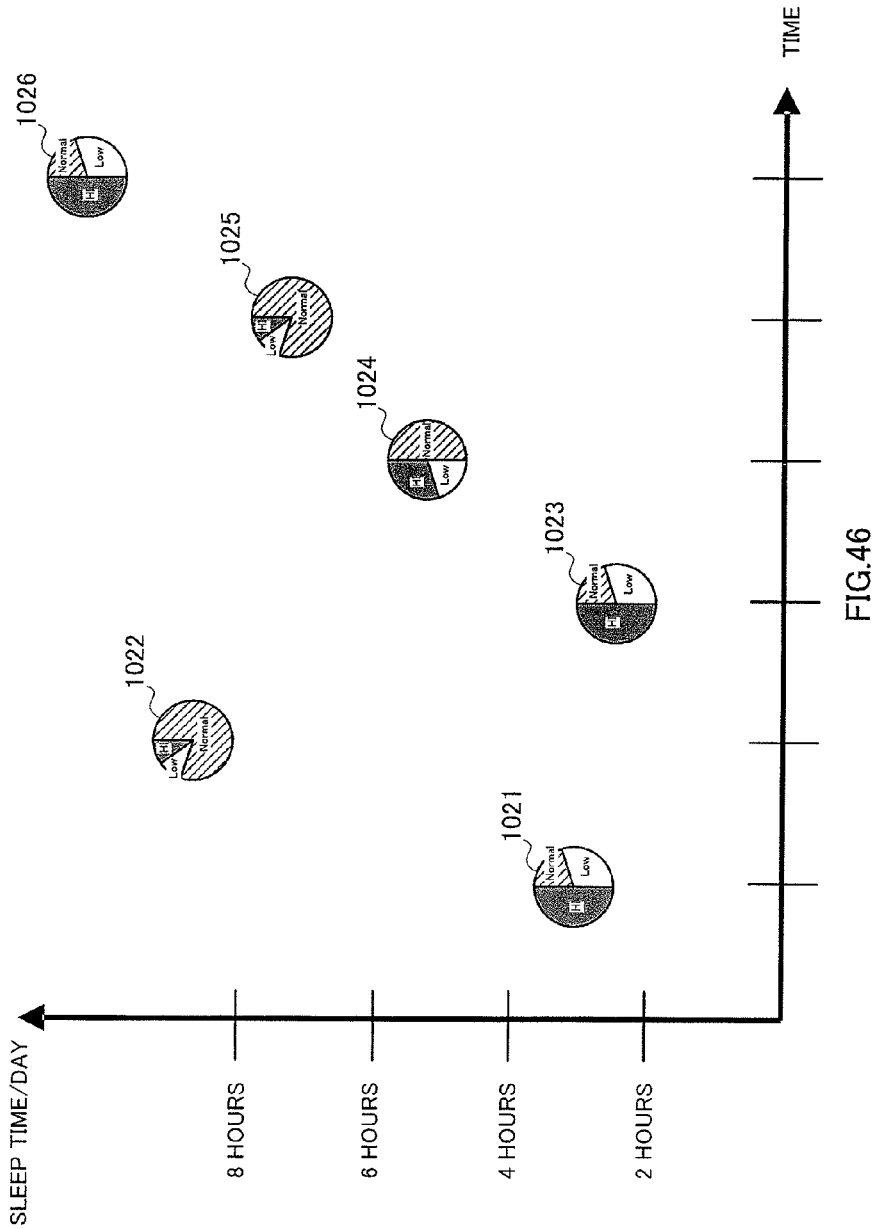
FIG. 46 illustrates an example of displaying changes over time in daily sleep duration and blood glucose level or CGM value on a blood glucose measuring system according to Embodiment 11.

FIG. 46 illustrates an example of displaying changes over time in daily sleep duration and blood glucose level or CGM value, where the horizontal axis is time which is graduated in days, and the vertical axis is daily sleep duration.

As illustrated in FIG. 46, each day's blood glucose level, coupled with daily sleep duration, is plotted on a graph. Blood glucose levels 1021 to 1026 are each displayed as a pie chart in which blood glucose levels measured in the week are classified into low, normal and high groups. Normal group is indicated by hatch lines, low group is indicated by a blank, and high group (abbreviated as "HI" in the chart) is indicated by a shaded area. These groups may be distinguished by different colors.

In the chart, "Normal" means standard blood glucose level, e.g., 70-180 mg/dl, "Low" means low blood glucose level, which is 70 mg/dl or less, and "High" means high blood glucose level, which is 180 mg/dl or higher.

In this way, blood glucose levels 1021 to 1026 are expressed as pie charts consisting of Normal, Low and High sections while being correlated with the corresponding daily sleep durations.

This graph allows for daily monitoring of changes in sleep duration and blood glucose level. Referring blood glucose 1021 of FIG. 46 where daily sleep duration is 3 hours, it can be seen at a glance that "High" accounted for approximately half of the total, with "Low" and "Normal" accounting for approximately ⅓ and less than ¼, respectively.

Blood glucose level 1022 is one in which daily sleep duration was over 8 hours. It can be seen at a glance that "Normal" accounted for approximately ¾ of the total, and "High" and "Low" account for approximately less than ¼ in total.

Blood glucose level 1023 is one in which daily sleep duration was about 2 hours. It can be seen at a glance that "High" accounted for approximately half of the total, whereas "Low" accounted for approximately ⅓ and "Normal" accounted for approximately less than ¼, as in the case of blood glucose level 1021.

Blood glucose level 1024 is one in which daily sleep duration was about 5 hours. It can be seen at a glance that "Normal" accounted for approximately half of the total, whereas "High" accounted for approximately ⅓ and "Low" accounted for approximately less than ¼.

Blood glucose level 1025 is one in which daily sleep duration was about 7 hours. It can be seen at a glance that "Normal" accounted for approximately ¾ of the total, and "High" and "Low" account for approximately less than ¼ in total, as in the case of blood glucose level 1022.

Blood glucose level 1026 is one in which daily sleep duration was over 9 hours. It can be seen at a glance that "High" accounted for approximately half of the total, whereas "Low" accounted for approximately ⅓ and "Normal" accounted for approximately less than ¼.

Figure 47:
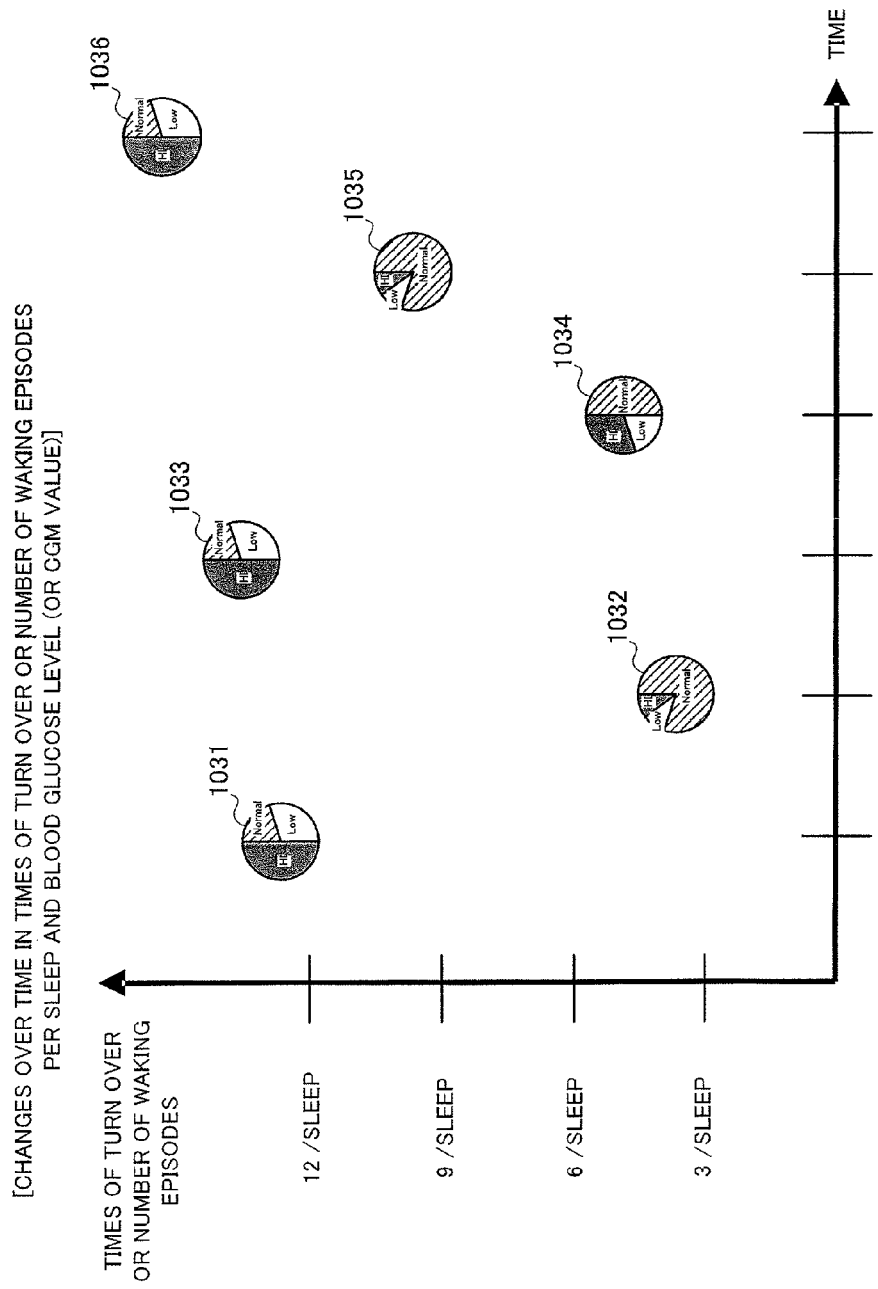
FIG. 47 illustrates an example of display of changes over time in the times of turn over or the number of waking episodes per sleep as well as in blood glucose level or CGM value on a blood glucose measuring system according to Embodiment 11.

By observing the changes in daily sleep duration and blood glucose level, it was established that the subject shows elevated blood glucose levels when daily sleep duration is shortened, as demonstrated by blood glucose levels 1021 and 1033 where daily sleep duration is shorter than 3 hours (see FIG. 47). It has thus been established that having appropriate sleep hours is preferable for the normalization of blood glucose level.

Normal blood glucose level accounted for approximately over half of the total both in blood glucose levels 1022 and 1024 where daily sleep duration is within 5 to 8 hours. It has been established that sleeping for 5 to 8 hours per day by itself makes it possible to normalize blood glucose levels even when other conditions (e.g., exercise amount and meal time) are identical.

In the case of blood glucose level 1026 where daily sleep duration is over 9 hours, "Normal" dropped to approximately less than ¼ of the total, suggesting that sleep quality is responsible for the normalization of blood glucose level in addition to length of sleep duration.

The display example of daily sleep durations and blood glucose levels shown in FIG. 46 provided a finding that sleeping for 5 to 8 hours a day results in normalization of blood glucose levels. Subjects can realize the effectiveness of keeping appropriate sleep hours, by displaying the correlation between daily sleep duration and blood glucose level on the display. Keeping appropriate sleep hours can normalize blood glucose levels without having to heavily rely on medications or other therapies.

In this way, according to this embodiment, it is possible to display novel display data regarding changes over time in daily sleep duration and blood glucose level, which information leads to improved daily habits.

FIG. 47 illustrates a display example of how the times of turn over or the number of waking episodes per sleep and blood glucose level or CGM value changes over time. In the graph the horizontal axis is time which is graduated in days, and the vertical axis is the times of turn over or the number of waking episodes per night.

Detection of turning over in bed during sleep has been described in Embodiment 7 with reference to FIG. 35. Counting the times of turn over or the number of waking episodes during sleep is one embodiment of [B. living activity measurement control], an embodiment realized for the first time in the present invention by correlating activity events such as meal and sleep with measurement data such as blood glucose level in real time. Note that turning over in bed during sleep is substantially equivalent to waking episode. The following embodiment counts the times of turn over during sleep by way of example.

As illustrated in FIG. 47, each day's blood glucose level, coupled with the times of turn over per night, is plotted on a graph. Blood glucose levels 1031 to 1036 are each displayed as a pie chart in which blood glucose readings in the day are classified into low, normal and high groups. Normal group is indicated by hatch lines, low group is indicated by a blank, and high group (abbreviated as "HI" in the chart) is indicated by a shaded area. These groups may be distinguished by different colors.

In the pie chart, "Normal" means standard blood glucose level, e.g., 70-180 mg/dl, "Low" means low blood glucose level, which is 70 mg/dl or less, and "High" means high blood glucose level, which is 180 mg/dl or higher.

In this way, blood glucose levels 1031 to 1036 are expressed as pie charts consisting of Normal, Low and High sections while being correlated with the corresponding the times of turn over per night.

Diabetes is also known to cause a sleep disorder, which can be characterized by the times of turn over or the number of waking episodes during sleep.

This graph allows for daily monitoring of changes over time in the degree of sleep disorder and blood glucose level. Referring blood glucose level 1031 of FIG. 47, it can be seen at a glance that when the times of turn over per night exceeds 12, "High" accounted for approximately half of the total, with "Low" and "Normal" accounting for approximately ⅓ and less than ¼, respectively.

Blood glucose level 1032 is one in which the times of turn over was 4 during sleep. It can be seen that "Normal" accounted for approximately ¾ of the total and "High" and "Low" accounted for approximately less than ¼ in total, suggesting that the subject attained quality sleep.

Blood glucose level 1033 is one in which the times of turn over was 13 during sleep. It can be seen at a glance that "High" accounted for approximately half of the total, whereas "Low" and "Normal" accounted for approximately ⅓ and less than ¼, respectively.

Blood glucose level 1034 is one in which the times of turn over was 5 during sleep. It can be seen that "Normal" accounted for approximately half of the total, whereas "High" and "Low" accounted for approximately ⅓ and less than ¼, respectively.

Blood glucose level 1035 is one in which the times of turn over was 9 during sleep. It can be seen that "Normal" accounted for approximately ¾ of the total and "High" and "Low" accounted for approximately less than ¼ in total, as in the case of blood glucose level 1032, Blood glucose level 1036 is one in which the times of turn over was 14 during sleep. It can be seen at a glance that "High" accounted for approximately half of the total, whereas "Low" and "Normal" accounted for approximately ⅓ and less than ¼, respectively.

By observing the changes in the times of turn over and blood glucose level, it was established that reducing the number of times the subject turned over in bed per night to 9 or less as in the case of blood glucose levels 1032 to 1035 by itself makes it possible to normalize blood glucose levels even when other conditions (e.g., exercise amount and meal time) are identical. On the other hand, when the number of times the subject turned over in bed per night exceeds 12 as in the case of blood glucose levels 1031, 1033 and 1036, it resulted in elevated blood glucose levels. Such a high frequency of turn over causes concern of possible sleep disorder in diabetic patients.

The display example of the times of turn over per night and blood glucose levels shown in FIG. 47 provided a finding that reducing the times of turn over to 9 or less per night results in normalization of blood glucose levels. By displaying the correlation between the times of turn over and blood glucose level, subjects can realize the effectiveness of improving their quality of sleep.

However, unlike exercise and meal time, it would be difficult for patients to voluntarily reduce the times of turn over during sleep. There have been no available methods of monitoring sleep quality based on the times of turn over, even though doctors are anxious about whether or not their patients are sleeping well. This embodiment allows doctors to take proper actions for patients suspected of having sleep disorder, such as changing prescription medications or introducing the patient to another specialist.

According to this embodiment, it is possible to display novel display data with regard to changes over time in the times of turn over per night and blood glucose level. The data can be used for improving daily habits.

It should be noted that although changes over time in living activity level and blood glucose level have been described by way of example, CGM value may be measured instead of blood glucose level. It should be also noted that since the blood glucose level varies at different times of the day, typically whether measured preprandially or postprandially, it is preferable to previously select either of preprandial blood glucose level or postprandial blood glucose level. Preprandial blood glucose measurement reveals the exact efficacy of medication administered, whereas postprandial blood glucose measurement makes it easy to identify postprandial high blood glucose levels.

Embodiment 12

Doctors monitor their patients' blood glucose by relying on self-reports of blood glucose values, and judge whether the current courses of treatment (e.g., lifestyle improvement therapy based on exercise therapy and dietary therapy, oral antidiabetic drug therapy, incretin therapy, or insulin therapy) should be continued or need to be changed.

In the case where a diabetic patient uses a blood glucose meter capable of monitoring of living activity level, the patient's doctor confirms blood glucose levels as well as lifestyle in terms of living activity level, step count, calories consumed, meal time, sleep duration and the like, through the data displayed either on the blood glucose meter's screen or on the screen of a computer to which the data has been downloaded, and judges whether the current courses of treatment (e.g., lifestyle improvement therapy based on exercise therapy and dietary therapy, oral antidiabetic drug therapy, incretin therapy, or insulin therapy) should be continued or need to be changed. This information is essential when deciding the treatment strategy of diabetes, a chronic adult disease, since judgment can be made based not only on the blood glucose level—mere fragmentary information that reflects the patient's physical condition—but also on information that allows the doctor to grasp the patient's overall lifestyle.

In Embodiment 12, novel information is displayed or recorded with regard to changes over time in living activity level and blood glucose level, which is one embodiment of [C. Detailed analysis control].

Figure 48:
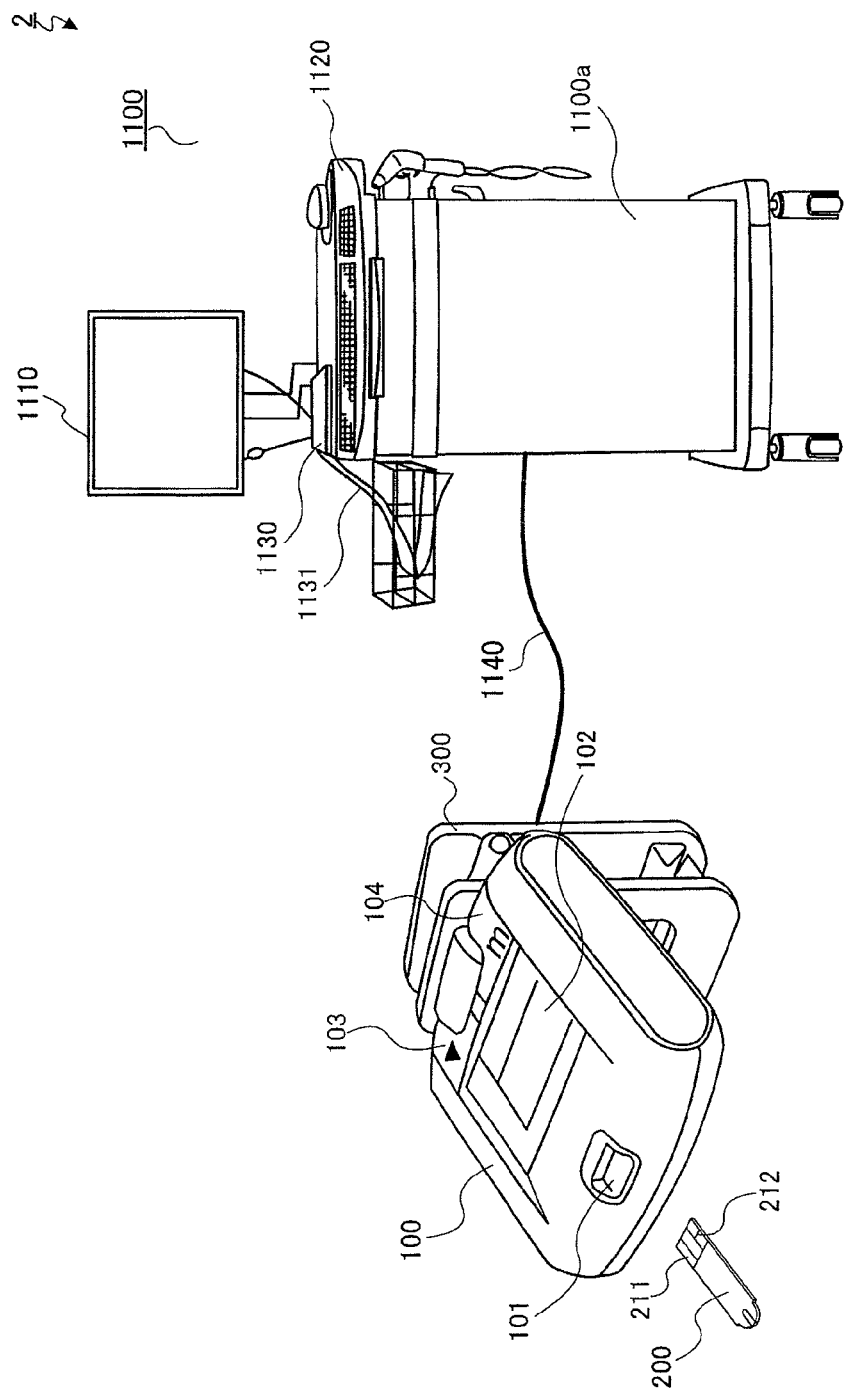
FIG. 48 is an overview illustration of a blood glucose measuring system according to Embodiment 12.

FIG. 48 is an overview illustration of a blood glucose measuring system according to Embodiment 12. Like components are denoted by the same numerals as those in FIGS. 1 and 2 and will not be explained.

As illustrated in FIG. 48, blood glucose measuring system 2 includes blood glucose measuring device 100 and blood glucose analyzing device 1100, which are coupled together by USB cable 1140. Instead of USB cable 1140, a dedicate cable may be used.

Blood glucose analyzing device 1100 includes main body 1100a, display 1110 which is a LCD, operation section 1120 composed of a keyboard, a mouse and the like, and printer 1130.

Display 1110 displays thereon two- or three-dimensional data of combinations of parameters such as living activity level, blood glucose level or CGM value, and insulin dose.

Using the keyboard, mouse and the like of operation section 1120, doctors or other operators, for example, select parameters and select mode such as [blood glucose level change display control mode] or [detailed analysis control mode].

Printer 1130 outputs as report 1131 the data displayed on display 1110, which data is the combination of parameters such as living activity level, blood glucose level or CGM value, and insulin dose.

Report 1131, which includes the above display data as well as additional information such as clinical findings and comments to the subject, can be printed on a display side (recordable side) of a single sheet of paper.

Blood glucose analyzing device 1100 is a terminal personal computer (PC), typically a general-purpose computer such as a desktop PC.

USB cable 1140 is used to connect the interface (not illustrated) of main body 1100a to computer interface 116 (FIG. 2) of blood glucose measuring device 100. Instead of USB cable 1140, a dedicate cable may be used. Alternatively, the devices may be connected wireless via specified near-field wireless communication, Bluetooth®, RF communication, or infrared communication such as infrared data association (IrDA) standard communication.

Figure 49:
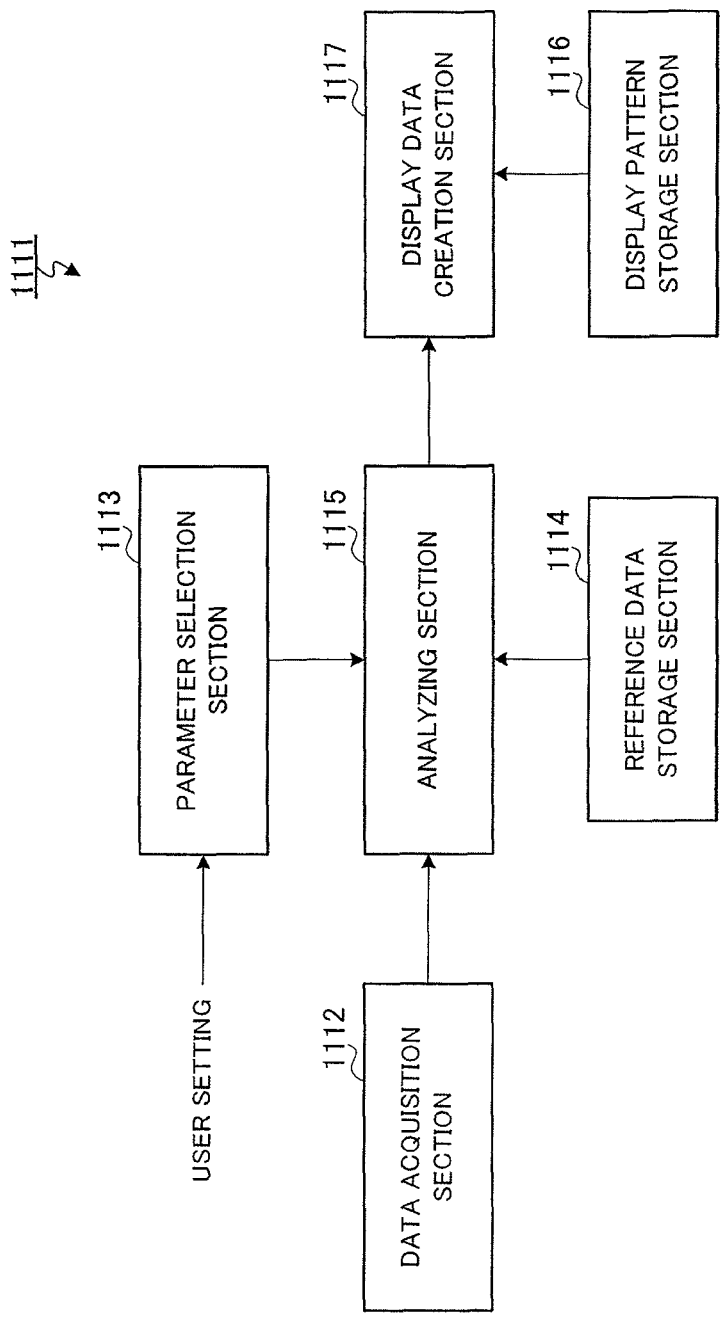
FIG. 49 is a block diagram of a control section which controls a detailed analysis process of a blood glucose analyzing device of a blood glucose measuring system according to Embodiment 12.

FIG. 49 is a block diagram of control section 1111 which controls a detailed analysis process of blood glucose analyzing device 1100.

As illustrated in FIG. 49, control section 1111 includes data acquisition section 1112, parameter selection section 1113, reference data storage section 1114, analysis section 1115, display pattern storage section 1116, and display data creation section 1117.

Data acquisition section 1112 acquires blood glucose data associated with living activity levels and stored in recording section 111 of blood glucose measuring device 100 (FIG. 2).

Parameter selection section 1113 selects any desired combination of the following first to sixth parameters according to the user setting or default setting.
First parameter: living activity level
Second parameter: blood glucose level or CGM value
Third parameter: insulin dose
Fourth parameter: meal time or meal count
Fifth parameter: sleep duration
Sixth parameter: times of turn over or number of waking episodes
The living activity level and times of turn over or number of waking episodes are both detected by motion measurement section (acceleration sensor) 112 (FIG. 2). These parameters may be plotted against time.

In this example parameter selection section 1113 combines two or more of the first to sixth parameters; for example, when two of them are combined, it selects, for example, living activity level (first parameter) and blood glucose level (second parameter), in response to the user's instruction.

When three of the parameters are combined, parameter selection section 1113 selects, for example, living activity level (first parameter), CGM value (second parameter), and insulin dose (third parameter). Moreover, parameter selection section 1113 can select parameters other than living activity level; for example, it selects blood glucose level (second parameter), sleep duration (fifth parameter), and times of turn over (sixth parameter).

Herein, each of the first to sixth parameters is normalized based on, for example, blood glucose level so that no significant difference occurs between any combinations of the parameters. Parameter selection section 1113 selects, for example, living activity level (first parameter) and blood glucose level (second parameter), in response to the user instruction.

Parameter selection section 1113 makes a desired combination of the parameters and outputs it to analysis section 1115.

Reference data storage section 1114 stores reference data corresponding to the first to sixth parameters. For example, in the case of blood glucose level, it stores a reference value of 70-180 mg/dl.

Analysis section 1115 performs a detailed analysis based on the data transmitted from data acquisition section 1112 and on the combined parameters selected and combined by parameter selection section 1113, with reference to the reference data stored in reference data storage section 1114. Detailed analysis involves displaying the respective parameters as variables on in 2D or 3D graphics.

Display pattern storage section 1116 stores therein display patterns used to display data in 2D or 3D.

Display data creation section 1117 creates, with reference to the display pattern stored in display pattern storage section 1116, display data that shows the analysis result provided by analysis section 1115 in 2D or 3D. Display data creation section 1117 may create any desired display data as long as the data shows the analysis of the combination of two or more of the first to sixth parameters.

Let us take a case in which analysis section 1115 analyzes in detail the first parameter living activity level and the second parameter blood glucose level and outputs the analysis result to display data creation section 1117, for example. Display data creation section 1117 can also create display data that shows simple plots of living activity level and blood glucose level.

As shown in FIG. 44, display data creation section 1117 preferably creates a plot of living activity level vs. time in association with detailed information of blood glucose level, showing the distribution of blood glucose level values with pie charts.

Figure 50:
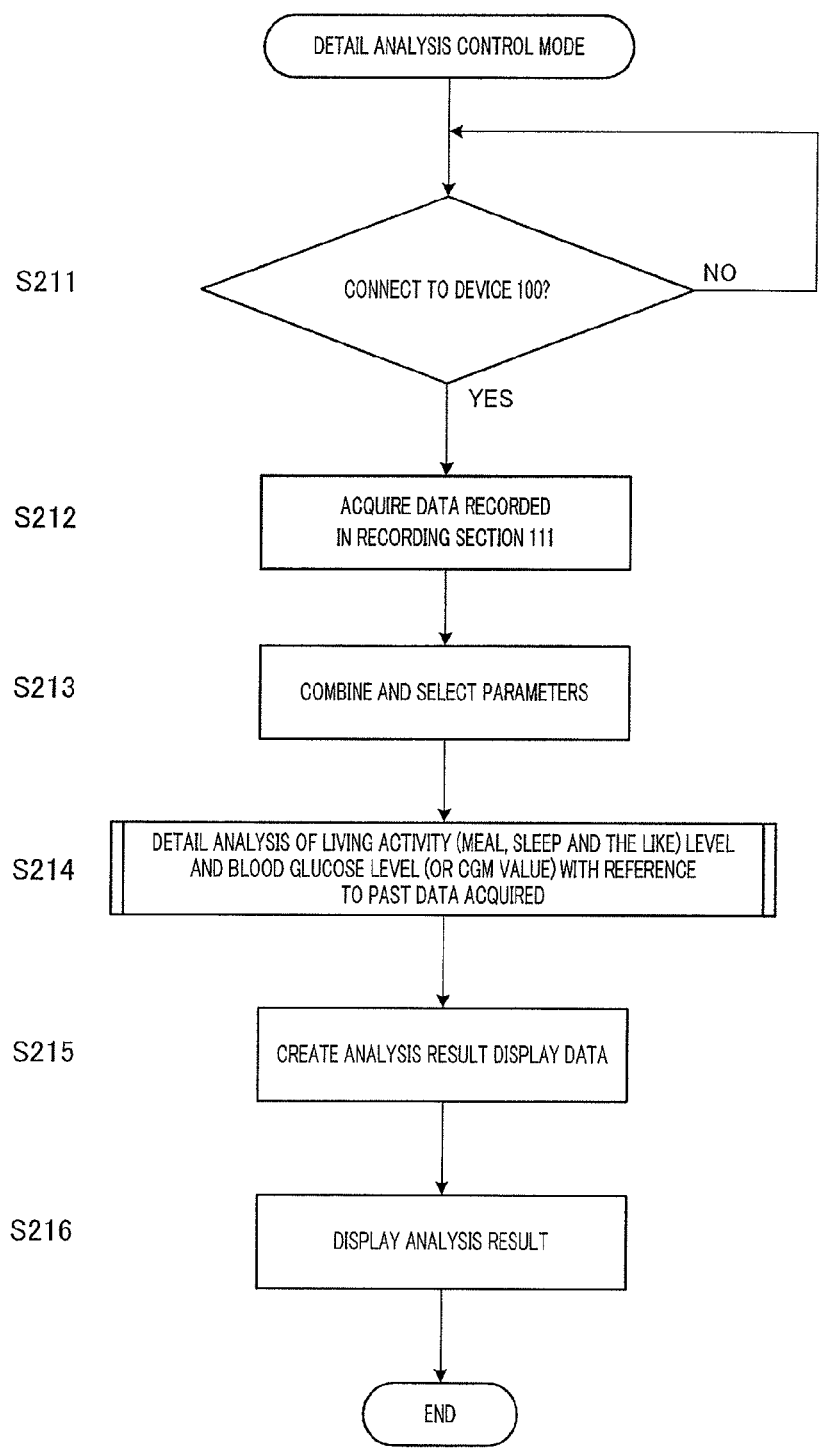
FIG. 50 is a flowchart of detailed analysis control mode in a blood glucose analyzing device of a blood glucose measuring system according to Embodiment 12.

FIG. 50 is a flowchart of detailed analysis control mode in blood glucose analyzing device 1100.

When detailed analysis control mode is activated, in step S211, blood glucose analyzing device 1100 determines whether or not it has been connected with blood glucose measuring device 100.

When blood glucose analyzing device 1100 is connected with blood glucose measuring device 100, in step S212, data acquisition section 1112 acquires blood glucose data associated with living activity level, which is stored in recording section 111 of blood glucose measuring device 100 (FIG. 2).

As has been described in the above-described embodiments, daily living activities includes meal (meal time and meal time zone) and sleep (sleep duration and sleep time zone, or times of turn over or the number of waking episodes). These events are detected by motion measurement section (acceleration sensor) 112, are combined with blood glucose data sent from blood glucose sensor 200, and are stored in recording section 111 (FIG. 2).

Recording methods have been described in detail in Embodiment 1 (FIGS. 8, 10 and 12), Embodiments 2 to 4 (FIGS. 16 to 22), Embodiment 10 (FIG. 42), and so forth. Other than blood glucose level, living activity level can be combined with CGM value or insulin dose, as has been described in detail for example in Embodiment 8 (FIG. 37). Needless to say, these parameters can be combined in various ways to provide different types of novel information.

Referring back to the flow of FIG. 50, in step S213, parameter selection section 1113 combines two or more of the above first to sixth parameters according to the user setting or default setting.

In step S214, analysis section 1115 performs a detailed analysis based on the data transmitted from data acquisition section 1112 and on the combined parameters selected and combined by parameter selection section 1113, with reference to the reference data stored in reference data storage section 1114. Specifically, analysis section 1115 analyzes in detail the living activity level (e.g., meal and sleep) and blood glucose level or CGM value with reference to the past values acquired from recording section 111 of blood glucose measuring device 100.

In step S215, display data creation section 1117 creates, with reference to the display pattern stored in display pattern storage section 1116, display data that shows the analysis result provided by analysis section 1115 in 2D or 3D. For example, display data creation section 1117 creates novel display data by combining measured values of living activity level and blood glucose level (CGM value or insulin dose).

In step S216 blood glucose analyzing device 1100 displays the created data on display 1110, causes printer 1130 to print out a report, and terminates the flow.

Figure 51:
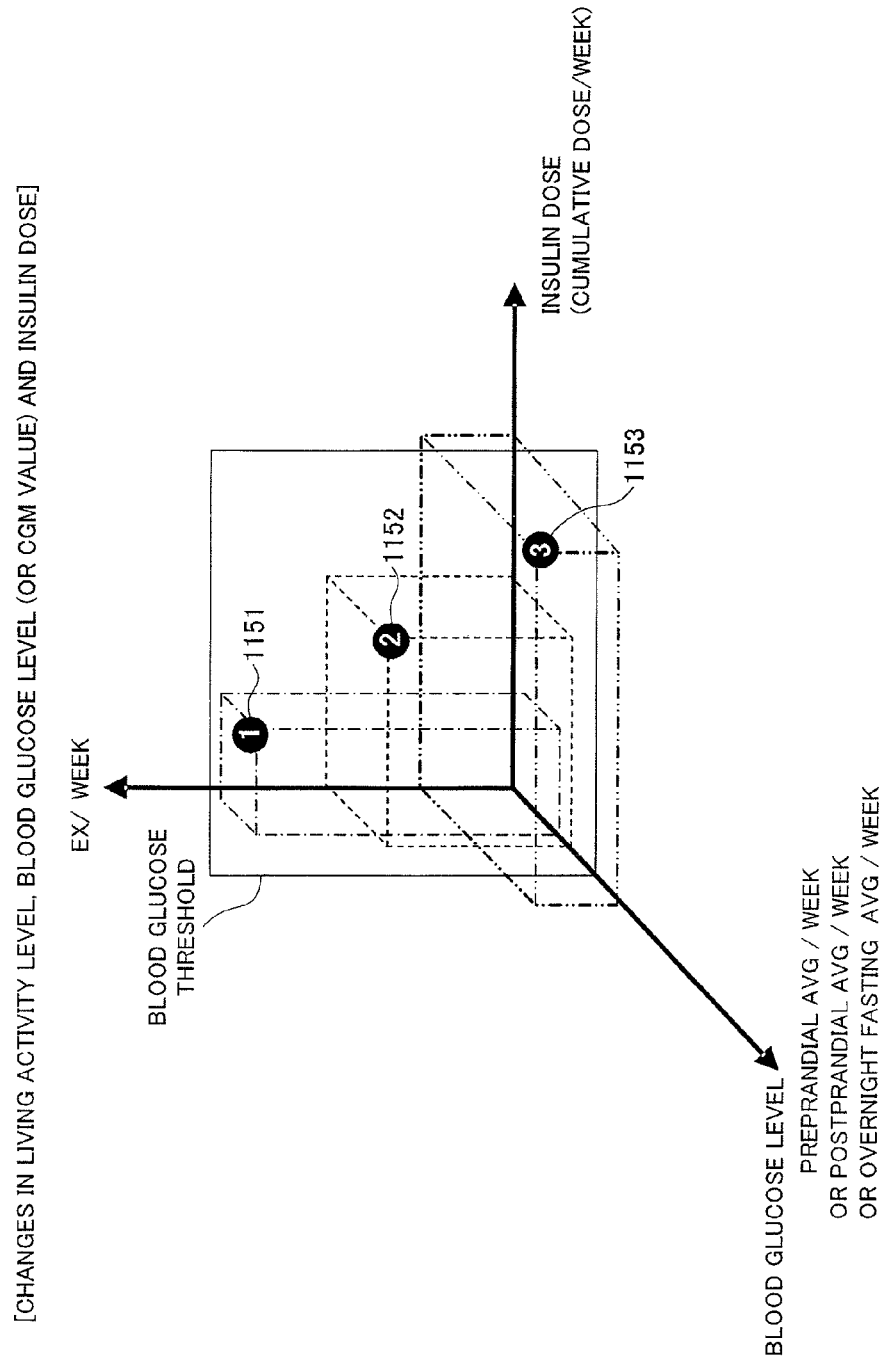
FIG. 51 shows changes in living activity level, blood glucose level or CGM value and insulin dose, measured with a blood glucose measuring system according to Embodiment 12.
Figure 52:
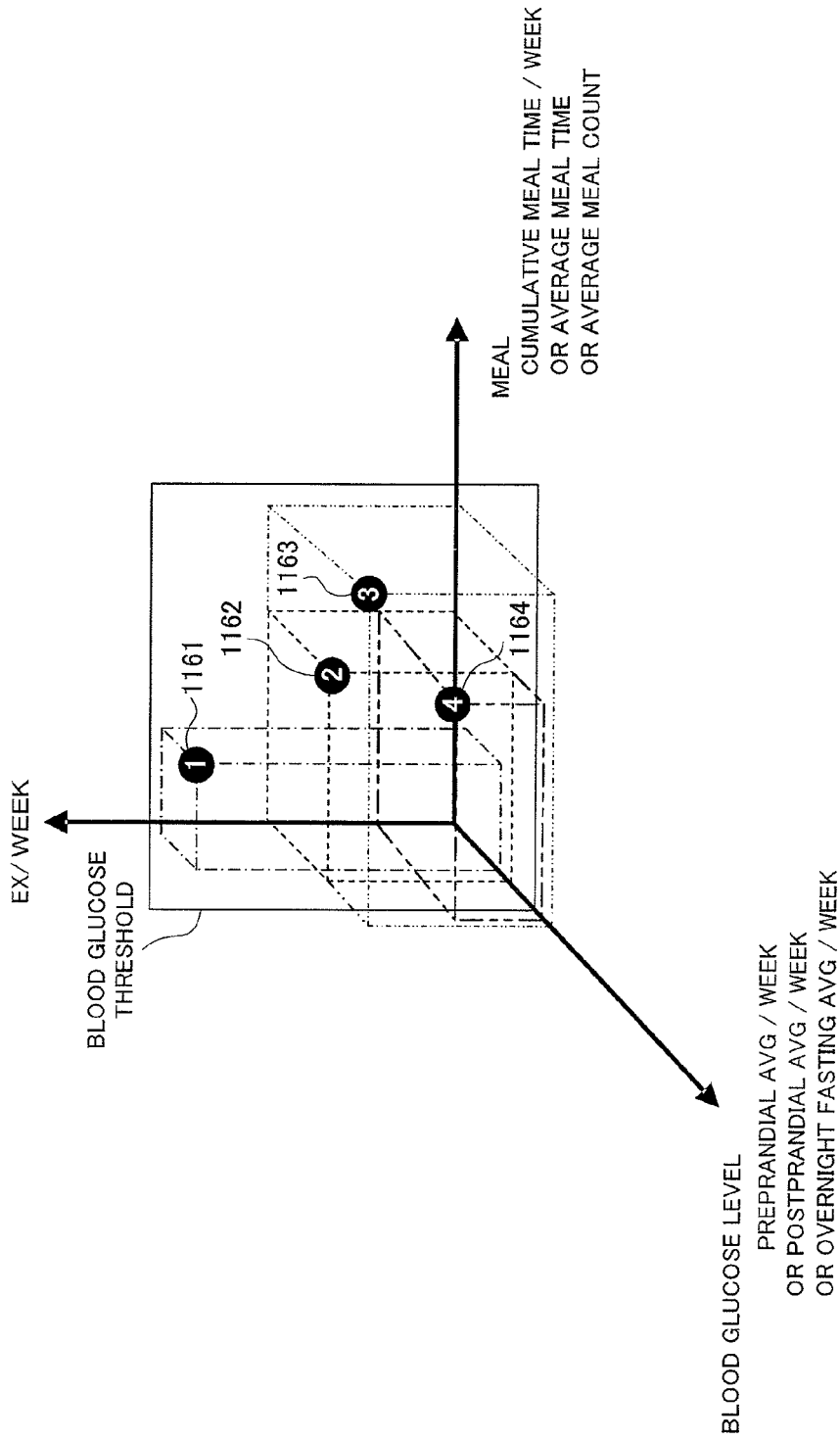
FIG. 52 shows changes in blood glucose level or CGM value and lifestyle, measured with a blood glucose measuring system according to Embodiment 12.
Figure 53:
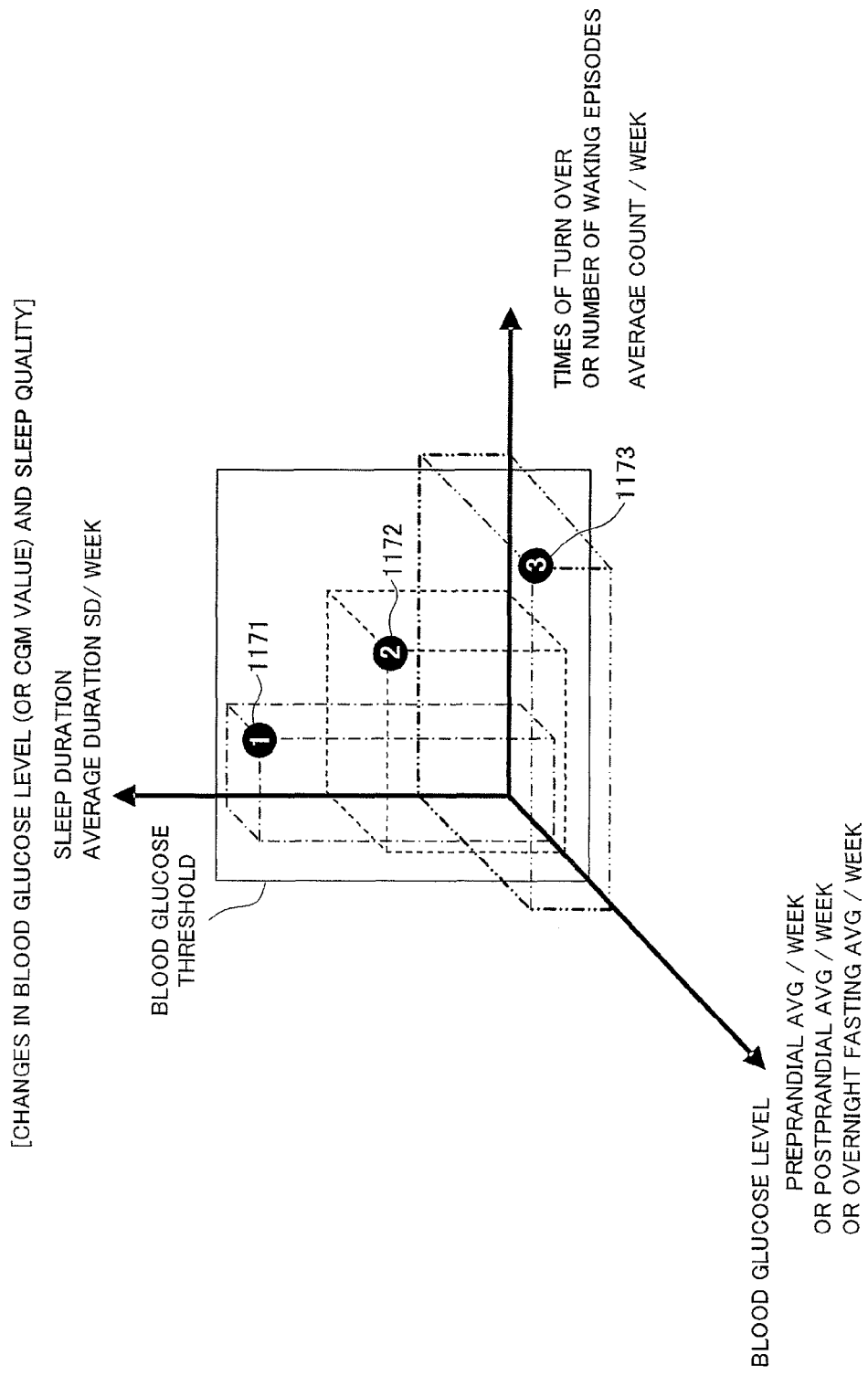
FIG. 53 shows changes in blood glucose level or CGM value and sleep quality, measured with a blood glucose measuring system according to Embodiment 12.

FIGS. 51 to 53 show a display example of novel display data created and displayed by executing the above flow.

FIG. 51 shows changes in living activity level, blood glucose level or CGM value, and insulin dose, wherein x axis is insulin dose (cumulative dose/week), y axis is blood glucose level, and z axis is exercise amount. A threshold value of blood glucose is also indicated. Note that the blood glucose level is a weekly average of any one of preprandial blood glucose levels, postprandial blood glucose levels, and overnight fasting blood glucose levels.

As shown in FIG. 51, data of living activity level, blood glucose level and insulin dose over 3 weeks are plotted in a three dimensional coordinate system. These plotted data are respectively termed plotted points 1151, 1152 and 1153, each of which is denoted by the black dot with a white number. In FIG. 51, broken lines are auxiliary lines for plotted points 1151 to 1153. Plotted points 1151 to 1153 may be distinguished by different colors.

This graph allows users to monitor changes in living activity level, blood glucose level and insulin dose on a weekly basis.

Referring to plotted point 1151, exercise amount is large whereas blood glucose level and insulin dose are low, showing that effective exercise reduced the blood glucose level and insulin dose and therefore the subject was in good condition during the week.

Plotted point 1152 corresponds to the following week's data where the exercise amount dropped.

As the exercise amount of plotted point 1152 decreased to below that of plotted point 1151 (i.e., the previous week's exercise amount), the blood glucose level and insulin dose both increased. Nevertheless, the blood glucose level is still below the threshold value on Y axis.

Plotted point 1153 corresponds to the following week's data where the exercise amount further dropped.

As the exercise amount of plotted point 1153 decreased to far below that of plotted point 1152, blood glucose level and insulin dose both remarkably increased, with blood glucose level exceeding the threshold value. This may correspond to a case where a diabetic patient did little effective exercise during the week.

In this way it can be understood at a glance that the performance of exercise contributes to changes in blood glucose level and insulin dose.

As described above, living activity level and blood glucose level are closely correlated with each other, and it is known that exercise in itself improve blood glucose levels.

No specific indicators have been available in the art for exercise amount (living activity level), blood glucose level and insulin dose. According to this embodiment, it is possible to quantitatively notify how blood glucose level and insulin dose change depending on the exercise amount (living activity level).

It is the present invention that first discloses creating such novel display data.

In particular, in this embodiment, blood glucose measuring device 10 is connected with blood glucose analyzing device 1100 (FIG. 48) with, for example, USB cable 1140. Medical practitioners such as doctors use blood glucose analyzing device 1100. Blood glucose analyzing device 1100 executes detailed analysis control mode of FIG. 50, thereby performing a detailed analysis with reference to the measured values (past values) associated with living activity level, which are stored in recording section 111 of blood glucose measuring system 100 (FIG. 2).

By executing detailed analysis control mode of FIG. 48, blood glucose analyzing device 1100 displays novel information like those shown in FIG. 51 and later-referenced FIGS. 52 and 53. By watching a display such as that shown in FIG. 51, doctors quantitatively monitor changes in their patients' exercise amount, blood glucose level and insulin dose over time, whereby they can customize an exercise menu or reduce the administration dose or frequency of medication according the effectiveness of exercise to the patient.

This embodiment is not intended to merely compare and display exercise amount (living activity level) and blood glucose level; rather, the feature is that living activity levels are organically coupled with other parameters (herein, blood glucose level and insulin dose) on the display.

For example, when specifically focusing on blood glucose levels of plotted points 1151 and 1152 in FIG. 51, both fall within the threshold. Blood glucose levels are normal at plotted points 1151 and 1152, but the exercise amount in fact dropped in the second week.

Suppose the patient was receiving a medication during the period, it can be conjectured that he/she did little exercise during the second week, relying on medication to maintain normal blood glucose levels. Moreover, the doctor can estimate the efficacy of the medication for the patient, which is useful for diagnosis and treatment.

On the other hand, suppose the patient was not receiving any medication during the period, the doctor can estimate how much exercise (living activity) is needed for the patient to maintain normal blood glucose levels, by comparing plotted point 1151 and plotted point 1152 in terms of z axis.

Representing changes over time in exercise amount (living activity level) and blood glucose level, coupled with insulin dose, in a three dimensional coordinate system provides more clear diagnostic criteria. Referring to FIG. 51, by comparing plotted point 1151 and plotted point 1152 in terms of x axis, it can be learned that the patient was receiving a medication throughout the period as the cumulative insulin dose shows a regular increase, whereby mutual relationship among changes in living activity level, blood glucose level and insulin dose can be understood at a glance. The doctor can also estimate the efficacy of insulin medication, which is useful for diagnosis and treatment.

For example, referring to plotted point 1153, the patient's blood glucose level exceeds the normal range (threshold) despite increased insulin dose. In this case, the doctor concludes that mere insulin administration is insufficient for the normalization of blood glucose levels, and therefore can explain to the patient that exercise is indispensable. The doctor can also make a most effective exercise menu for the patient while minimizing loads.

According to this embodiment, by organically coupling exercise amount (living activity level) with other parameters (blood glucose level and insulin dose) for analysis and by displaying the results in a three dimensional coordinate system, it is possible to provide novel display data which has not been achieved in that. This is expected to break new ground in the field of blood glucose diagnosis.

Here, as to changes in exercise amount and blood glucose level, FIG. 44 of Embodiment 1 is also effective.

Although the subject' condition was monitored over three weeks in this embodiment, the monitoring period is not specifically limited; it may be four weeks, several hours, etc.

Further, the transition of plotted point may be indicated by arrows. For example, when plotted points 1151 to 1153 correspond to the first to third weeks, respectively, the transition can be more easily tracked by connecting them with arrows as follows: 1151→1152→1153.

FIG. 52 shows changes in blood glucose level or CGM value and lifestyle. In this example changes in lifestyle are expressed in terms of living activity level and meal. In the graph x axis is meal parameter (cumulative meal time/week), y axis is blood glucose level, and z axis is exercise amount. Note that the meal parameter on x axis is any one of weekly cumulative meal time, weekly average meal time, and weekly meal count. The blood glucose level on y axis is a weekly average of any one of preprandial blood glucose levels, postprandial blood glucose levels, and overnight fasting blood glucose levels.

Although the following description employs average meal time as a parameter on x axis, cumulative meal time and average meal count provide substantially the same result as average meal time. Note that average meal time increases toward negative direction of x axis.

As shown in FIG. 52, data of living activity level, blood glucose level and average meal time over 4 weeks are plotted in a three dimensional coordinate system. These plotted data are respectively termed plotted points 1161, 1162, 1163 and 1164, each of which is denoted by the black dot with a white number. In FIG. 52, broken and chain lines are auxiliary lines for plotted points 1161 to 1164. Plotted points 1161 to 1164 may be distinguished by different colors.

This graph allows users to monitor changes in blood glucose level and lifestyle (living activity and meal) on a weekly basis.

Referring to plotted point 1161, the exercise amount is large, the blood glucose level is low, and the average meal time is long, showing that the subject was in good condition with normal blood glucose levels during the week as a result of performing a high level of exercise and taking a sufficient time to eat meals on average.

Plotted points 1162 to 1164 are cases where the exercise amount is low. There is a tendency that blood glucose levels increase with decreasing exercise amount.

Referring to plotted point 1162, the blood glucose level increased due to the decreased exercise amount and short average meal time compared to plotted point 1161 (i.e., previous week). Nevertheless, the blood glucose level is still below the threshold value on Y axis.

Referring to plotted point 1163, even though this week's exercise amount is comparable to that of plotted point 1162, the blood glucose level increased to an extent that exceeds the threshold value on y axis due to the short average meal time compared to plotted point 1162.

Plotted point 1163 corresponds to a week where the exercise amount is reduced to far below that of plotted point 1162. However, the average meal time is comparable to that of plotted point 1162.

Referring to plotted point 1164, even though this week's average meal time is comparable to that of plotted point 1162, the blood glucose level is far above that of plotted point 1163 due to the decreased exercise amount compared to plotted point 1162.

These results establish that as the exercise mount decreases, meal time/meal count more significantly affects blood glucose level. Namely, the blood glucose level and meal time/meal count increase with decreasing exercise amount. Thus, slight changes in the meal time/meal count affect blood glucose level.

In this way it can be understood at a glance that the performance of exercise contribute changes in blood glucose level and lifestyle (living activity and meal).

According to this embodiment, it is possible to quantitatively inform how exercise amount (living activity level) alters the blood glucose level and insulin dose. In particular, in situations where adequate exercise amount is ensured, meal time/meal count only indirectly affects blood glucose level. It was thus established that as the exercise mount decreases, meal time/meal count more significantly affects blood glucose level.

Detailed analysis of plotted points 1162 and 1163, where the exercise amount is moderate, revealed that leading a life while caring for the meal time/meal count results in normalization of blood glucose levels. In addition, a doctor can quantitatively confirm this on the display monitor. Meanwhile, with reference to plotted point 1164 where the exercise amount is yet reduced, the doctor can quantitatively confirm that merely caring for the meal time or meal count will fail to normalize blood glucose levels. This is novel information not achieved in the art and is expected to break new ground in the field of blood glucose diagnosis.

FIG. 53 shows changes in blood glucose level or CGM value and sleep quality, excluding living activity level as a parameter. In the graph, x axis is the times of turn over or the number of waking episodes (average count/week), y axis is blood glucose level, and z axis is sleep duration (average time/week). A threshold value of blood glucose level is indicated on y axis. Note that the meal parameter on x axis is any one of weekly cumulative meal time, weekly average meal time, and weekly meal count.

The blood glucose level on y axis is a weekly average of any one of preprandial blood glucose levels, postprandial blood glucose levels, and overnight fasting blood glucose levels.

As shown in FIG. 53, data of blood glucose level, times of turn over and sleep duration over 3 weeks are plotted in a three dimensional coordinate system. These plotted data are respectively termed plotted points 1171, 1172 and 1173, each of which is denoted by the black dot with a white number. In FIG. 53, broken and chain lines are auxiliary lines for plotted points 1171 to 1173. Plotted points 1171 to 1173 may be distinguished by different colors.

This graph allows users to monitor changes in blood glucose level and sleep quality on a weekly basis.

Referring to plotted point 1171, sleep duration is long and the times of turn over is small, suggesting that high sleep quality resulted in normalization of blood glucose levels.

Plotted points 1172 and 1173 correspond to cases where sleep quality was reduced. Blood glucose level increases with decreasing sleep quality which is expressed in terms of sleep duration and the times of turn over during sleep.

Referring to plotted point 1172, the sleep duration and times of turn over decreased compared to plotted point 1171. Nevertheless, the blood glucose level is still below the threshold value on Y axis.

Referring to plotted point 1173, the sleep duration and times of turn over further decreased compared to plotted point 1172. However, the blood glucose level increased to an extent that exceeds the threshold value on y axis.

From the graph it can be understood both blood glucose level and sleep quality (sleep duration and times of turn over) at a glance.

According to this embodiment, it is possible to quantitatively inform how blood glucose level changes depending on sleep quality.

In this embodiment an example where blood glucose analyzing device 1100 executes the above described [C. Detailed analysis control], but it may be executed by blood glucose measuring device 100.

Embodiment 13

Embodiment 13 describes an impact detection control operation in blood glucose measuring device 100.

In the U.S. all hospitals must keep at least two years of records for quality certificates in the hospital, patients' blood glucose levels, information of patients and operators, etc., as required by the Joint Commission on Accreditation of Healthcare Organization (JCAHO).

Hand-written records, however, include errors such as missing parts. To avoid this problem a consortium including the Clinical and Laboratory Standards Institute (CLSI) developed "POCT1-A"—communication standards for POCT equipment.

POCT devices have a POCT1-A compliant communication system that enables them to communicate with an in-hospital database either wirelessly or via cable, allowing records to be readily computerized and stored in the database. In this way all of the blood glucose meters used in the hospitals across the U.S. have a communication system. However, these devices are in fact more sophisticated and expensive than personal blood glucose meters.

Moreover, even though these POCT blood glucose meters used in the U.S. hospitals are expensive devices, they often need replacing due to defects, which are most frequently caused by falling. In a bustling hospital, falling of device on the floor or the like inevitably occurs. For this reason, blood glucose meters designed for U.S. hospitals are not suitable in bustling hospitals.

If a blood glucose meter become completely inoperable due to falling, possible recording of wrong values due to defects can be avoided. On the other hand, if the device is still operable while having some glitch, it may record wrong blood glucose values or record values of the wrong patient.

Moreover, when the device is broken due to falling, the related medical practitioner at least must contact the manufacture's customer support center or other staff in charge, which rids them of the time for nursing or medical treatment.

Figure 54:
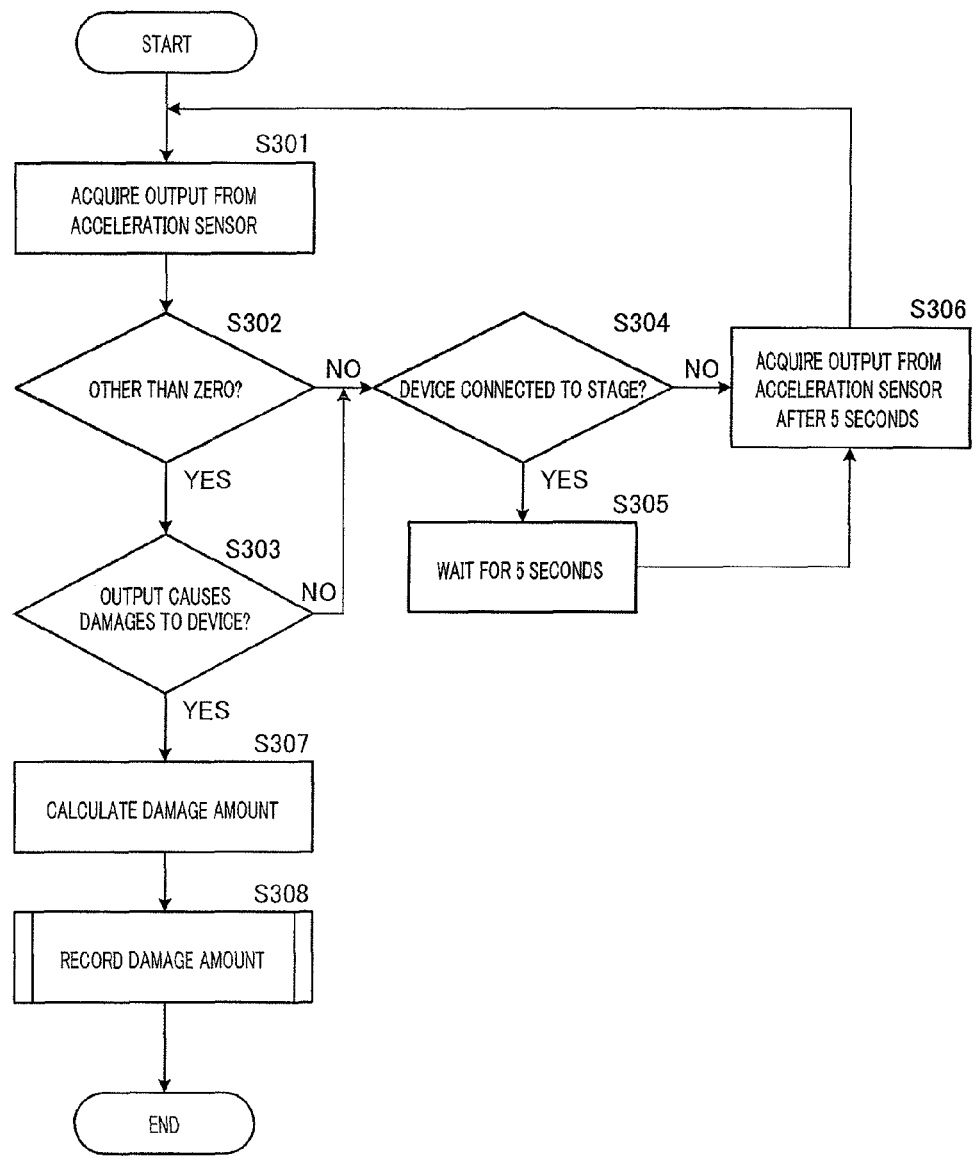
FIG. 54 is a flowchart of impact detection control in a blood glucose measuring device according to Embodiment 13.

FIG. 54 is a flowchart of impact detection control in a blood glucose measuring device according to Embodiment 13. This flow is repeatedly executed by CPU 110 (see FIG. 2; it also serves as damage monitoring means in this embodiment) at predetermined timings.

The hardware configuration of the blood glucose measuring system according to Embodiment 13 is identical to that illustrated in FIGS. 1 and 2. CPU 110 has a function of judging means that judges the amount of damage to the device body based on motion information, and a function of control means that records in recording section 111 (FIG. 2) the judged damage amount and the number of times the device has been damaged, and notifies the same to the user.

By way of example, acceleration sensor 112 is shown as the motion measurement section in FIGS. 1 and 2. It may be replaced with an angular speed sensor, a vibration sensor or the like.

First, in step S301, CPU 110 acquires output from acceleration sensor 112.

In step S302, CPU 110 determines whether or not the output is other than zero.

When it has been determined that the output is other than zero, that is, when acceleration sensor has detected any motion, the process proceeds to step S303. On the other hand, when the output is not other than zero, the process proceeds to step S304.

In step S303, CPU 110 determines, based on the output from acceleration sensor 112, whether or not the measured value of acceleration sensor 112 was such a level that damaged blood glucose measuring device 100.

For example, based on the magnitude of the measured value of acceleration sensor 112, CPU 110 ranks the magnitude of damage as "high", "mediate" or "low", with "high" indicating that an impact damaging the device has been applied, and "mediate" and "low" indicating that an impact not damaging the device has been applied.

In cases where the impact was not so large as to damage blood glucose measuring device 100 or where the output from acceleration sensor 112 was determined to be zero in step S302, in step S304, CPU 110 determines whether or not blood glucose measuring device 100 is placed on a certain stage. A state where blood glucose measuring device 100 is placed on a stage can be confirmed by the fact that blood glucose measuring device 100 has a corresponding cable connected to computer interface 116 (FIG. 2). For example, when a USB cable is employed, the connection can be detected when it is attached to or detached from the device.

When blood glucose measuring device 100 is placed on a certain stage, in step S305, CPU 110 waits for a predetermined time (e.g., 5 seconds) followed by proceeding to step S306. When blood glucose measuring device 100 is not placed on a certain stage, on the other hand, the process directly proceeds to step S306.

In step S306, CPU 110 waits for a predetermined time (e.g., 5 seconds) and then acquires an output from acceleration sensor 112. The process then returns to step S301.

When the impact was so large as to damage blood glucose measuring device 100, in step S307, CPU 110 calculates the amount of damage based on the output from acceleration sensor 112.

In step S308, CPU 110 records the calculated damage amount in recording section 111 (FIG. 2) and terminates the flow. Magnitude of damage may be recorded instead of damage amount.

Through the above process the amount of damage to the device due to falling and the number of times the device fell are recorded in recording section 111 of blood glucose measuring device 100.

Upon recording of damage amount in recording section 111, CPU 110 preferably informs the user of the fact that blood glucose measuring device received an impact, by displaying a message or the like on display section 102 or by voice.

Alternatively, CPU 110 may warn the user of possible recording of wrong readings as soon as it recorded the damage amount that may cause such recording. Further, blood glucose measuring device 100 may be so designed to activate by itself a device checking program at any desired time, e.g., upon power on. According to the results of the device operation check executed by the program, blood glucose measuring device 100 can implement a variety of countermeasures, including switching off the system, activating a stop program that disables the system's function to prevent user's manipulation, etc. With this, it is made possible to implement highly reliable blood glucose measurements without bothering medical practitioners while ensuring clinical safety.

Moreover, this embodiment and the control process of any of the above-described can be organically combined: For example, when CPU 110 has recorded damage amount in recording section 111, it sets up a flat that indicates that status, and then when execution of the control process of the above-described embodiment, such as [living activity measurement mode], [sleep processing mode], [living activity measurement mode] or [detailed analysis control mode], is instructed, CPU 110 checks the flag and, prior to execution of the control process, informs the user of the fact that blood glucose measuring device 100 received an impact.

This configuration allows the user to know in advance that blood glucose measuring device 100 received an impact, precluding the possibility of recording wrong blood glucose levels. It is difficult for users to judge whether blood glucose measuring device 100 received an impact by the device's appearance. According to this embodiment, it is possible to inform the user of receipt of impact to blood glucose measuring device 100 without having to activate a device checking program, thus providing reliable data all the time.

As damage amount is notified, the user can use blood glucose measuring device 100 while considering the degree of damage to the device. Damage amount is displayed in conjunction with information as to whether the device is operable or inoperable.

The amount of damage to blood glucose measuring device 100 is recorded in recording section 111 and can be output to the outside via computer interface 116 (FIG. 2). The status of damage can then be circulated among individuals concerned via Internet 905 or the like without bothering medical practitioners, as illustrated in FIG. 40, for example. Further, the manufacturer can analyze the status of damage so as to instruct replacing of a meter or offer maintenance.

The above preferable embodiments are for example purposes only, and shall not be construed as limiting the scope of the invention thereto.

For example, the embodiments may be directed to a system that monitors and provides human biochemical information, human living activity level information and dosage of medication to the human body, wherein a device to be placed on the human body transmits (a) at least one detected data regarding human biochemical parameter, (b) at least one directly detected data regarding human living activity level, and (c) data regarding the dosage of any desired medication to the human body, to any desired nearby computer with a communication function, and wherein the computer calculates status information regarding reciprocal influences to the respective data.

The biochemical information may be glucose level, and the dosage of medication may be insulin dosage.

CPU 110 of FIG. 2 determines whether living activity level is 1.5 to 13 METs. CPU 110 also classifies living activity levels according to MET. Note that "MET" is employed as one of preferable embodiments herein; living activity level may be expressed in terms of another figure or indicator.

Living activity level information preferably includes information of daily activities including up-down, right-left, and back-forth movements.

The systems according to Embodiments 1 to 9 may be so configured that all or some of blood glucose sensor 200, CGM sensor 600, acceleration sensor 112 and continuous subcutaneous insulin infusion pump can be detached from the main body.

The system may also be so configured that CGM sensor unit 500, insulin pump unit 700 or CGM insulin pump unit 800 is coupled to the measuring device (e.g., blood glucose measuring device 100) either wirelessly or via cable (preferably with a low-power near-field bilateral wireless communication system) and transmits detected data to the measuring device continuously or intermittently.

The measuring device may be so configured that it transmits data to another wiredly or wirelessly coupled management device continuously or intermittently. In particular, allowing a patient (e.g., diabetic patient) to carry any of the above sensor units while being set apart from the measuring device reduces the load on the patient.

In the above embodiments, the terms "blood glucose measuring system", "blood glucose measuring device", "CGM sensor unit", "insulin pump unit" and "CGM insulin pump unit" have been used for reasons of convenience; it should be noted however that the device names may be "blood glucose controlling device", "diabetes self-controlling device", "insulin infusion device" and the like. The blood glucose measuring method may also be called "blood glucose controlling method" or the like.

The devices may also be named after their function disclosed in the respective embodiments, such as blood glucose analysis controlling device, diabetes controlling device, device for counting the times of turn over, priming controlling device, and the like. The same holds for the method. The devices may be called blood glucose measuring device, CGM device, insulin pump device and the like by focusing on the type of the biosensor or the type of insulin delivery scheme.

There are no particular limitations to the type, number, connection method, etc., of the members (e.g., display section) of the blood glucose measuring device. For the motion measurement section, any sensor can be employed that detects motions of human activity; not only acceleration sensors, but angular speed sensors and vibration sensors may be employed. The acceleration sensor, angular speed sensor or the like used as the motion measurement section may be called an activity meter.

The blood glucose measuring method, CGM controlling method, insulin pump controlling method described above can also be implemented by a program that causes them to function. The program is stored in a computer-readable recording medium.

The disclosure of Japanese Patent Application No. 2008-283784, filed on Nov. 4, 2008, including the specification, drawings and abstract, is incorporated herein by reference in its entirety.

INDUSTRIAL APPLICABILITY

A measurement device, insulin infusion device, measurement method, method of controlling insulin infusion device, and program according to the present invention are capable of measurement of blood glucose level and living activity level with a single device. The devices and methods allow a diabetic patient to live a more healthy life, as well as allow medical practitioners to easily keep track of the patient's living activity levels and blood glucose levels. Thus, clinical activities become more beneficial to diabetic patients.

REFERENCE SIGNS LIST 1, 2, 401: blood glucose measuring system
100, 402: blood glucose measuring device
101: sensor attachment section
102, 406: display section
103: operation key
104: memory & decision key
110: CPU
111: recording section
112: motion measurement section
113: blood glucose measuring circuit section
114, 115: connection section
116: computer interface
117, 550, 780: temperature measurement section
200: blood glucose sensor
300: attachment section
500: CGM sensor unit
510: CGM sensor unit circuit section
520, 720: living activity measurement section
530, 730: communication section
540, 740: power supply
600: CGM sensor
600A: CGM sensor connector
700: insulin pump unit
710: insulin pump unit circuit section
750: insulin infusion unit
751: opening
752: communication channel
753: cannula connector
760: pump section
770: cannula
800: CGM insulin pump unit
810: CGM insulin pump unit circuit section
1100: blood glucose analyzing device
1100a: blood glucose analyzing device's main body
1100: display
1111: control section
1112: data acquisition section
1113: parameter selection section
1114: reference data storage section
1115: analysis section
1116: display pattern storage section
1117: display data creation section
1120: operation section
1130: printer
1131: report
1140: USB cable

What is claimed is:

1. A measurement device comprising:
 a housing that has an attached biosensor that includes a reagent selectively responding to a specific analyte in a biological fluid, and is configured so as to be carried by a user;
 an analyte measurer that measures a concentration of the specific analyte with a biosensor;
 a motion measurer that measures a motion level of the housing based on vibration applied to the housing, wherein the motion measurer determines an orientation of the housing with respect to a horizontal and, based upon the determined orientation, measures the vibration applied to the housing after a predetermined time period;

a living activity level calculator that calculates a living activity level of the user in terms of intensity of motion by a living activity of the user, based on the motion level of the housing measured by the motion measurer;

a recorder that records the living activity level calculated by the living activity level calculator; and a controller that is programmed to detect a plurality of living activity levels recorded in the recorder greater than a first threshold, used to identify a moving activity in daily life to identify an interval between two of the moving activities and the length of the interval to identify a non-moving activity, to determine a meal event if the interval is longer than a predetermined time to identify meal time, to determine whether a time of the measurement of the concentration of the specific analyte performed by the analyte measurer is before the meal event or after the meal event, and to record the concentration of the specific analyte measured by the analyte measurer before the meal event and the concentration of the specific analyte measured by the analyte measurer after the meal event in a distinguishable state in the recorder.

2. The measurement device according to claim 1, further comprising a time counter, wherein the controller uses timing information output from the time counter when determining the meal event.

3. The measurement device according to claim 1, further comprising a transmitter that transmits the concentration of the specific analyte measured by the analyte measurer before the meal event and the concentration of the specific analyte measured by the analyte measurer after the meal event in the distinguishable state, to an external equipment.

4. The measurement device according to claim 1, further comprising a display that displays the concentration of the specific analyte measured by the analyte measurer before the meal event and the concentration of the specific analyte measured by the analyte measurer after the meal event in the distinguishable state.

5. The measurement device according to claim 1, wherein the biosensor is a disposable glucose sensor to adhere a user's blood.

6. The measurement device according to claim 1, wherein the biosensor is a continuous glucose monitoring sensor to be inserted under skin of the user.

7. The measurement device according to claim 1, wherein the controller estimates a meal event based upon living activity during a preceding predetermined time period and, based upon whether a predetermined number of living activities of a predetermined level occurred during the predetermined time period.

* * * * *